United States Patent [19]
Ikeda

[11] Patent Number: 5,385,834
[45] Date of Patent: Jan. 31, 1995

[54] MUTANT T7 RNA POLYMERASE GP1(LYS222) EXHIBITING ALTERED PROMOTER RECOGNITION

[75] Inventor: Richard A. Ikeda, Atlanta, Ga.

[73] Assignee: Georgia Tech Research Corporation, Atlanta, Ga.

[21] Appl. No.: 106,433

[22] Filed: Aug. 13, 1993

[51] Int. Cl.$^6$ .................. C07H 21/00; C12N 9/12; C12N 15/54

[52] U.S. Cl. .................. 435/172.3; 435/194; 536/23.2; 935/31; 935/41

[58] Field of Search .................. 435/69.1, 172.3, 320.1, 435/194, 252.33; 536/23.2; 935/31, 29, 41

[56] References Cited

PUBLICATIONS

Basu, S., & Maitra, U.(1986) *J. Mol. Biol.* 190, 425–437.
Bautz, E. K. F. (1976) in *RNA Polymerase* (Losick, R., & Chamberlin, M., eds.), pp. 273–284, Cold Spring Harbor Laboratory, Cold Spring Harbor, N.Y.
Brosius, J., & Holy, A. (1984) *Proc. Natl. Acad. Sci. USA* 81, 6929–6933.
Brosius, J., & Lupski, J. R. (1987) *Methods in Enzymology* 153, 54–68.
Chamberlin, M., McGrath, J., & Waskell, L. (1970) *Nature* 228, 227–231.
Chamberlin, M., & Ring. J. (1973a) *J. Biol. Chem.* 248, 2235–2244.
Chamberlin, M., & Ring, J. (1973b) *J. Biol. Chem.* 248, 2245–2250.
Chamberlin, M., & Ryan, T. (1982) in *The Enzymes* (Boyer, P. D., ed.), vol. 15, pp. 87–108, Academic Press, New York.
Chang, A. C. Y., & Cohen, S. N. (1978) *J. Bacteriol.* 134, 1141–1156.
Chapman, K. A., & Burgess, R. R. (1987) *Nucl. Acids. Res.* 15, 5413–5432.
Chapman, K. A., Gunderson, S. I., Anello, M., Wells, R. D., & Burgess, R. R. (1988) *Nucl. Acids Res.* 16, 4511–4524.
Davanloo, P., Rosenberg, A. H., Dunn, J. J., & Studier, F. W. (1984) *Proc. Natl. Acad. Sci. USA* 81, 2035–2039.

deBoer, H. A., Comstock, L. J., & Vasser, M. (1983) *Proc. Natl. Acad. Sci. USA* 80, 21–25.
deBoer, H. A., Comstock, L. J., Yansura, D. G., & Heynecker, H. L. (1982) in *Promoters, Structure and Function* (Rodriguez, R. L., & Chamberlin, M. J., Eds.) pp. 462–481, Praeger, N.Y.
Gross, L., Chen, W–J., & McAllister, W. T. (1992) *J. Mol. Biol.* 228, 488–505.
Gunderson, S. I., Chapman, K. A., & Burgess, R. R. (1987) *Biochemistry* 26, 1539–1546.
Ikeda, R. A. (1992) *J. Biol. Chem.* 267, 11322–11328.
Ikeda, R. A., Warshamana, G. S., & Chang, L. L. (1992a) *Biochemistry* 31, 9073–9080.
Ikeda, R. A., Ligman, C. M., & Warshamana, S. (1992b) *Nucl. Acids. Res.* 20, 2517–2524.
Ikeda, R. A., Lin, A. C., & Clarke, J. (1992c) *J. Biol. Chem.* 267, 2640–2649.
Ikeda, R. A., & Richardson, C. C. (1987) *J. Biol. Chem.* 262, 3790–3799.

(List continued on next page.)

Primary Examiner—Keith Baker
Assistant Examiner—Dian C. Jacobson
Attorney, Agent, or Firm—Deveau, Colton & Marquis

[57] ABSTRACT

*E. coli* harboring the mutant plasmid pKGP-HA1mut4 and an inactive pCM-X# are chloramphenicol resistant and that the mutation responsible for the expression of CAT from the inactive pCM-X# plasmid is a G to A transition at nucleotide 664 of T7 gene 1 that converts glutamic acid (222) to lysine. This mutation expands the range of T7 promoter sequences that can be utilized by the enzyme. The mutant T7 RNA polymerase, GP1(lys222), utilizes inactive T7 promoter point mutants more efficiently than wild-type T7 RNA polymerase both in vivo and in vitro. Furthermore, the correlation of in vivo and in vitro promoter utilization suggests that the restoration of chloramphenicol resistance in the cotransformed *E. coli* results from the ability of GP1(lys222) to initiate transcription from T7 promoter point mutants that are normally inactive.

4 Claims, 8 Drawing Sheets

PUBLICATIONS

Ikeda, R. A., & Richardson, C. C. (1986) *Proc. Natl. Acad. Sci. USA* 83, 3614–3618.

Joho, K. E., Gross, L. B., McGraw, N. J., Raskin, C., & McAllister, W. T. (1990) *J. Mol. Biol.* 215, 31–39.

Klement, J. F., Moorefield, M. B., Jorgensen, E., Brown, J. E., Risman, S., & McAllister, W. T. (1990) *J. Mol. Biol.* 215, 21–29.

Martin, C. T., & Coleman, J. E. (1987) *Biochemistry* 26, 2690–2696.

Moffatt, B. A., Dunn, J. J., & Studier, F. W. (1984) *J. Mol. Biol.* 173, 265–269.

Muller, D. K., Martin, C. T., & Coleman, J. E. (1989) *Biochemistry* 28, 3306–3313.

Muller, D. K., Martin, C. T., & Coleman, J. E. (1988) *Biochemistry* 27, 5763–5771.

Patra, D., Lafer, E. M., & Sousa, R. (1992) *J. Mol. Biol.* 224, 307–318.

Raskin, C. A., Diaz, G., Joho, K., & McAllister, W. T. (1992) *J. Mol. Biol.*, 228, 506–515.

Sambrook, J., Fritsch, E. F., & Maniatis, T. (1989) in *Molecular Cloning: A Laboratory Manual*, 2 ed., Cold Spring Harbor Laboratory Press, Cold Spring Harbor.

Smeekens, S. P., & Romano, L. J. (1986) *Nucl. Acids Res.* 14, 2811–2827.

Shi, Y., Gamper, H., & Hearst, J. E. (1988) *J. Biol. Chem.* 263, 527–534.

Studier, F. W., & Dunn, J. J. (1982) *Cold Spring Harbor Symp. Quant. Biol.* 47, 999–1007.

Tabor, S., & Richardson, C. C. (1985) *Proc. Natl. Acad. Sci USA* 82, 1074–1078.

Oakley, J. L., et al., T7 RNA Polymerase: Conformation, Functional Groups, and Promoter Binding, Biochemistry, vol. 14, No. 21, pp. 4684–4691 (1975).

Rose, R. E., The Nucleotide Sequence of pACYC177, Nucleic Acids Research vol. 16, No. 1, p. 356 (1988).

Schneider, T. D. et al., Information Content of Binding Sites on Nucleotide Sequences, J. Mol. Bio., vol. 188, pp.: 415–431 (1986).

Jones, R. N. et al., In Vitro Evaluation of CENTA, a New Beta–Lactamase–Susceptible Chromogenic Cephalosporin Reagen, J. Clin. Microbio., vol. 15, No. 5, pp. 954–958 (1982).

Shaw, W. V., Chloramphenicol Acetyltransferase from Chloramphenicol–Resistant Bacteria, Antibiotic Inactivation and Modification, p. 737–775.

Oakley, J. L., et al. T7 RNA Polymerase Promoter Structure and Polymerase Binding, Biochem., vol. 18, No. 3, pp. 528–537 (1979).

Dunn, J. J. et al., Complete Nucleotide Sequence of Bacteriophage T7 DNA and the Locations of T7 Genetic Elements, J. Mol. Biol., vol. 166, pp. 477–535 (1983).

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 2652 Base pairs
        ( B ) TYPE: Nucleic Acid
        ( C ) STRANDEDNESS: Double
        ( D ) TOPOLOGY: Linear ( i i ) MOLECULE TYPE: Other nucleic acid
        ( A ) DESCRIPTION:Molecule sequenced is a clone of the T7
            genomic DNA that spans T7 RNA polymerase ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Bacteriophage T7
        ( B ) STRAIN: Wild-type
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pKGP-HA1mut4

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: T7 RNA Polymerase GP1(lys222)
        ( B ) LOCATION: 1 to 2652
        ( C ) IDENTIFICATION METHOD: By expressing and characterizing
            the protein encoded by the gene.
        ( D ) OTHER INFORMATION: The glu to lys substitution at
            residue 222 alters promoter recognition by the
            T7 RNA polymerase ( x ) PUBLICATION INFORMATION:
        ( A ) AUTHORS: Ikeda, R.A., Chang, L.L., and Warshamana, G.S.
        ( B ) TITLE: Selection and Characterization of a Mutant T7
            RNA Polymerase that Recognizes an Expanded Range
            of T7-like Promoters
        ( C ) JOURNAL: Biochemistry
        ( D ) VOLUME: 32
        ( E ) ISSUE: 35
        ( F ) PAGES: 9115-9124
        ( G ) DATE: Sept. 7, 1993
        ( H ) DOCUMENT NUMBER:
        ( I ) FILING DATE:
        ( J ) PUBLICATION DATE:
        ( K ) RELEVANT RESIDUES IN SEQ ID NO: Nucleotides 1 to
            2652 encode the entire T7 RNA polymerase
            GP1(lys222); however, the difference between
            GP1(lys222) and wild-type T7 RNA polymerase is a
            G to A substitution at nucleotide 664

( i x ) SEQUENCE DESCRIPTION: SEQ ID NO:1:

```
ATG  AAC  ACG  ATT  AAC  ATC  GCT  AAG  AAC  GAC  TTC  TCT  GAC  ATC  GAA  CTG      48
Met  Asn  Thr  Ile  Asn  Ile  Ala  Lys  Asn  Asp  Phe  Ser  Asp  Ile  Glu  Leu
                         5                        10                       15

GCT  GCT  ATC  CCG  TTC  AAC  ACT  CTG  GCT  GAC  CAT  TAC  GGT  GAG  CGT  TTA      96
Ala  Ala  Ile  Pro  Phe  Asn  Thr  Leu  Ala  Asp  His  Tyr  Gly  Glu  Arg  Leu
                        20                        25                       30
```

-continued

| | | | | | | | | | | | | | | | | |
|---|---|---|---|---|---|---|---|---|---|---|---|---|---|---|---|---|
| GCT | CGC | GAA | CAG | TTG | GCC | CTT | GAG | CAT | GAG | TCT | TAC | GAG | ATG | GGT | GAA | 144 |
| Ala | Arg | Glu | Gln | Leu | Ala | Leu | Glu | His | Glu | Ser | Tyr | Glu | Met | Gly | Glu | |
| | | 35 | | | | | 40 | | | | | 45 | | | | |
| GCA | CGC | TTC | CGC | AAG | ATG | TTT | GAG | CGT | CAA | CTT | AAA | GCT | GGT | GAG | GTT | 192 |
| Ala | Arg | Phe | Arg | Lys | Met | Phe | Glu | Arg | Gln | Leu | Lys | Ala | Gly | Glu | Val | |
| | 50 | | | | 55 | | | | | 60 | | | | | | |
| GCG | GAT | AAC | GCT | GCC | GCC | AAG | CCT | CTC | ATC | ACT | ACC | CTA | CTC | CCT | AAG | 240 |
| Ala | Asp | Asn | Ala | Ala | Ala | Lys | Pro | Leu | Ile | Thr | Thr | Leu | Leu | Pro | Lys | |
| 65 | | | | 70 | | | | 75 | | | | | 80 | | | |
| ATG | ATT | GCA | CGC | ATC | AAC | GAC | TGG | TTT | GAG | GAA | GTG | AAA | GCT | AAG | CGC | 288 |
| Met | Ile | Ala | Arg | Ile | Asn | Asp | Trp | Phe | Glu | Glu | Val | Lys | Ala | Lys | Arg | |
| | | | | 85 | | | | | 90 | | | | | 95 | | |
| GGC | AAG | CGC | CCG | ACA | GCC | TTC | CAG | TTC | CTG | CAA | GAA | ATC | AAG | CCG | GAA | 336 |
| Gly | Lys | Arg | Pro | Thr | Ala | Phe | Gln | Phe | Leu | Gln | Glu | Ile | Lys | Pro | Glu | |
| | | | 100 | | | | | 105 | | | | | 110 | | | |
| GCC | GTA | GCG | TAC | ATC | ACC | ATT | AAG | ACC | ACT | CTG | GCT | TGC | CTA | ACC | AGT | 384 |
| Ala | Val | Ala | Tyr | Ile | Thr | Ile | Lys | Thr | Thr | Leu | Ala | Cys | Leu | Thr | Ser | |
| | | | 115 | | | | 120 | | | | | 125 | | | | |
| GCT | GAC | AAT | ACA | ACC | GTT | CAG | GCT | GTA | GCA | AGC | GCA | ATC | GGT | CGG | GCC | 432 |
| Ala | Asp | Asn | Thr | Thr | Val | Gln | Ala | Val | Ala | Ser | Ala | Ile | Gly | Arg | Ala | |
| | | 130 | | | | | 135 | | | | | 140 | | | | |
| ATT | GAG | GAC | GAG | GCT | CGC | TTC | GGT | CGT | ATC | CGT | GAC | CTT | GAA | GCT | AAG | 480 |
| Ile | Glu | Asp | Glu | Ala | Arg | Phe | Gly | Arg | Ile | Arg | Asp | Leu | Glu | Ala | Lys | |
| 145 | | | | | 150 | | | | | 155 | | | | | 160 | |
| CAC | TTC | AAG | AAA | AAC | GTT | GAG | GAA | CAA | CTC | AAC | AAG | CGC | GTA | GGG | CAC | 528 |
| His | Phe | Lys | Lys | Asn | Val | Glu | Glu | Gln | Leu | Asn | Lys | Arg | Val | Gly | His | |
| | | | | 165 | | | | | 170 | | | | | 175 | | |
| GTC | TAC | AAG | AAA | GCA | TTT | ATG | CAA | GTT | GTC | GAG | GCT | GAC | ATG | CTC | TCT | 576 |
| Val | Tyr | Lys | Lys | Ala | Phe | Met | Gln | Val | Val | Glu | Ala | Asp | Met | Leu | Ser | |
| | | | 180 | | | | | 185 | | | | | 190 | | | |
| AAG | GGT | CTA | CTC | GGT | GGC | GAG | GCG | TGG | TCT | TCG | TGG | CAT | AAG | GAA | GAC | 624 |
| Lys | Gly | Leu | Leu | Gly | Gly | Glu | Ala | Trp | Ser | Ser | Trp | His | Lys | Glu | Asp | |
| | | 195 | | | | | 200 | | | | | 205 | | | | |
| TCT | ATT | CAT | GTA | GGA | GTA | CGC | TGC | ATC | GAG | ATG | CTC | ATT | AAG | TCA | ACC | 672 |
| Ser | Ile | His | Val | Gly | Val | Arg | Cys | Ile | Glu | Met | Leu | Ile | Lys | Ser | Thr | |
| | | 210 | | | | 215 | | | | | 220 | | | | | |
| GGA | ATG | GTT | AGC | TTA | CAC | CGC | CAA | AAT | GCT | GGC | GTA | GTA | GGT | CAA | GAC | 720 |
| Gly | Met | Val | Ser | Leu | His | Arg | Gln | Asn | Ala | Gly | Val | Val | Gly | Gln | Asp | |
| 225 | | | | | 230 | | | | | 235 | | | | | 240 | |
| TCT | GAG | ACT | ATC | GAA | CTC | GCA | CCT | GAA | TAC | GCT | GAG | GCT | ATC | GCA | ACC | 768 |
| Ser | Glu | Thr | Ile | Glu | Leu | Ala | Pro | Glu | Tyr | Ala | Glu | Ala | Ile | Ala | Thr | |
| | | | | 245 | | | | | 250 | | | | | 255 | | |
| CGT | GCA | GGT | GCG | CTG | GCT | GGC | ATC | TCT | CCG | ATG | TTC | CAA | CCT | TGC | GTA | 816 |
| Arg | Ala | Gly | Ala | Leu | Ala | Gly | Ile | Ser | Pro | Met | Phe | Gln | Pro | Cys | Val | |
| | | | 260 | | | | | 265 | | | | | 270 | | | |
| GTT | CCT | CCT | AAG | CCG | TGG | ACT | GGC | ATT | ACT | GGT | GGT | GGC | TAT | TGG | GCT | 864 |
| Val | Pro | Pro | Lys | Pro | Trp | Thr | Gly | Ile | Thr | Gly | Gly | Gly | Tyr | Trp | Ala | |
| | | 275 | | | | | 280 | | | | | 285 | | | | |
| AAC | GGT | CGT | CGT | CCT | CTG | GCG | CTG | GTG | CGT | ACT | CAC | AGT | AAG | AAA | GCA | 912 |
| Asn | Gly | Arg | Arg | Pro | Leu | Ala | Leu | Val | Arg | Thr | His | Ser | Lys | Lys | Ala | |
| | 290 | | | | | 295 | | | | | 300 | | | | | |
| CTG | ATG | CGC | TAC | GAA | GAC | GTT | TAC | ATG | CCT | GAG | GTG | TAC | AAA | GCG | ATT | 960 |
| Leu | Met | Arg | Tyr | Glu | Asp | Val | Tyr | Met | Pro | Glu | Val | Tyr | Lys | Ala | Ile | |
| 305 | | | | 310 | | | | | 315 | | | | | 320 | | |
| AAC | ATT | GCG | CAA | AAC | ACC | GCA | TGG | AAA | ATC | AAC | AAG | AAA | GTC | CTA | GCG | 1008 |
| Asn | Ile | Ala | Gln | Asn | Thr | Ala | Trp | Lys | Ile | Asn | Lys | Lys | Val | Leu | Ala | |
| | | | | 325 | | | | | 330 | | | | | 335 | | |
| GTC | GCC | AAC | GTA | ATC | ACC | AAG | TGG | AAG | CAT | TGT | CCG | GTC | GAG | GAC | ATC | 1056 |
| Val | Ala | Asn | Val | Ile | Thr | Lys | Trp | Lys | His | Cys | Pro | Val | Glu | Asp | Ile | |
| | | | 340 | | | | | 345 | | | | | 350 | | | |
| CCT | GCG | ATT | GAG | CGT | GAA | GAA | CTC | CCG | ATG | AAA | CCG | GAA | GAC | ATC | GAC | 1104 |
| Pro | Ala | Ile | Glu | Arg | Glu | Glu | Leu | Pro | Met | Lys | Pro | Glu | Asp | Ile | Asp | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 355 |     |     |     |     | 360 |     |     |     |     | 365 |     |     |     |      |
| ATG | AAT | CCT | GAG | GCT | CTC | ACC | GCG | TGG | AAA | CGT | GCT | GCC | GCT | GCT | GTG | 1152 |
| Met | Asn | Pro | Glu | Ala | Leu | Thr | Ala | Trp | Lys | Arg | Ala | Ala | Ala | Ala | Val |      |
|     | 370 |     |     |     | 375 |     |     |     |     | 380 |     |     |     |     |     |      |
| TAC | CGC | AAG | GAC | AAG | GCT | CGC | AAG | TCT | CGC | CGT | ATC | AGC | CTT | GAG | TTC | 1200 |
| Tyr | Arg | Lys | Asp | Lys | Ala | Arg | Lys | Ser | Arg | Arg | Ile | Ser | Leu | Glu | Phe |      |
| 385 |     |     |     | 390 |     |     |     |     | 395 |     |     |     |     |     | 400 |      |
| ATG | CTT | GAG | CAA | GCC | AAT | AAG | TTT | GCT | AAC | CAT | AAG | GCC | ATC | TGG | TTC | 1248 |
| Met | Leu | Glu | Gln | Ala | Asn | Lys | Phe | Ala | Asn | His | Lys | Ala | Ile | Trp | Phe |      |
|     |     |     |     | 405 |     |     |     |     | 410 |     |     |     |     | 415 |     |      |
| CCT | TAC | AAC | ATG | GAC | TGG | CGC | GGT | CGT | GTT | TAC | GCT | GTG | TCA | ATG | TTC | 1296 |
| Pro | Tyr | Asn | Met | Asp | Trp | Arg | Gly | Arg | Val | Tyr | Ala | Val | Ser | Met | Phe |      |
|     |     |     | 420 |     |     |     |     | 425 |     |     |     |     | 430 |     |     |      |
| AAC | CCG | CAA | GGT | AAC | GAT | ATG | ACC | AAA | GGA | CTG | CTT | ACG | CTG | GCG | AAA | 1344 |
| Asn | Pro | Gln | Gly | Asn | Asp | Met | Thr | Lys | Gly | Leu | Leu | Thr | Leu | Ala | Lys |      |
|     |     | 435 |     |     |     |     | 440 |     |     |     |     | 445 |     |     |     |      |
| GGT | AAA | CCA | ATC | GGT | AAG | GAA | GGT | TAC | TAC | TGG | CTG | AAA | ATC | CAC | GGT | 1392 |
| Gly | Lys | Pro | Ile | Gly | Lys | Glu | Gly | Tyr | Tyr | Trp | Leu | Lys | Ile | His | Gly |      |
|     | 450 |     |     |     | 455 |     |     |     |     | 460 |     |     |     |     |     |      |
| GCA | AAC | TGT | GCG | GGT | GTC | GAT | AAG | GTT | CCG | TTC | CCT | GAG | CGC | ATC | AAG | 1440 |
| Ala | Asn | Cys | Ala | Gly | Val | Asp | Lys | Val | Pro | Phe | Pro | Glu | Arg | Ile | Lys |      |
| 465 |     |     |     | 470 |     |     |     |     | 475 |     |     |     |     |     | 480 |      |
| TTC | ATT | GAG | GAA | AAC | CAC | GAG | AAC | ATC | ATG | GCT | TGC | GCT | AAG | TCT | CCA | 1488 |
| Phe | Ile | Glu | Glu | Asn | His | Glu | Asn | Ile | Met | Ala | Cys | Ala | Lys | Ser | Pro |      |
|     |     |     |     | 485 |     |     |     |     | 490 |     |     |     |     | 495 |     |      |
| CTG | GAG | AAC | ACT | TGG | TGG | GCT | GAG | CAA | GAT | TCT | CCG | TTC | TGC | TTC | CTT | 1536 |
| Leu | Glu | Asn | Thr | Trp | Trp | Ala | Glu | Gln | Asp | Ser | Pro | Phe | Cys | Phe | Leu |      |
|     |     |     | 500 |     |     |     |     | 505 |     |     |     |     | 510 |     |     |      |
| GCG | TTC | TGC | TTT | GAG | TAC | GCT | GGG | GTA | CAG | CAC | CAC | GGC | CTG | AGC | TAT | 1584 |
| Ala | Phe | Cys | Phe | Glu | Tyr | Ala | Gly | Val | Gln | His | His | Gly | Leu | Ser | Tyr |      |
|     |     | 515 |     |     |     |     | 520 |     |     |     |     | 525 |     |     |     |      |
| AAC | TGC | TCC | CTT | CCG | CTG | GCG | TTT | GAC | GGG | TCT | TGC | TCT | GGC | ATC | CAG | 1632 |
| Asn | Cys | Ser | Leu | Pro | Leu | Ala | Phe | Asp | Gly | Ser | Cys | Ser | Gly | Ile | Gln |      |
|     |     | 530 |     |     |     |     | 535 |     |     |     |     | 540 |     |     |     |      |
| CAC | TTC | TCC | GCG | ATG | CTC | CGA | GAT | GAG | GTA | GGT | GGT | CGC | GCG | GTT | AAC | 1680 |
| His | Phe | Ser | Ala | Met | Leu | Arg | Asp | Glu | Val | Gly | Gly | Arg | Ala | Val | Asn |      |
| 545 |     |     |     |     | 550 |     |     |     |     | 555 |     |     |     |     | 560 |      |
| TTG | CTT | CCT | AGT | GAA | ACC | GTT | CAG | GAC | ATC | TAC | GGG | ATT | GTT | GCT | AAG | 1728 |
| Leu | Leu | Pro | Ser | Glu | Thr | Val | Gln | Asp | Ile | Tyr | Gly | Ile | Val | Ala | Lys |      |
|     |     |     |     | 565 |     |     |     |     | 570 |     |     |     |     | 575 |     |      |
| AAA | GTC | AAC | GAG | ATT | CTA | CAA | GCA | GAC | GCA | ATC | AAT | GGG | ACC | GAT | AAC | 1776 |
| Lys | Val | Asn | Glu | Ile | Leu | Gln | Ala | Asp | Ala | Ile | Asn | Gly | Thr | Asp | Asn |      |
|     |     |     | 580 |     |     |     |     | 585 |     |     |     |     | 590 |     |     |      |
| GAA | GTA | GTT | ACC | GTG | ACC | GAT | GAG | AAC | ACT | GGT | GAA | ATC | TCT | GAG | AAA | 1824 |
| Glu | Val | Val | Thr | Val | Thr | Asp | Glu | Asn | Thr | Gly | Glu | Ile | Ser | Glu | Lys |      |
|     |     | 595 |     |     |     |     | 600 |     |     |     |     | 605 |     |     |     |      |
| GTC | AAG | CTG | GGC | ACT | AAG | GCA | CTG | GCT | GGT | CAA | TGG | CTG | GCT | TAC | GGT | 1872 |
| Val | Lys | Leu | Gly | Thr | Lys | Ala | Leu | Ala | Gly | Gln | Trp | Leu | Ala | Tyr | Gly |      |
|     | 610 |     |     |     | 615 |     |     |     |     | 620 |     |     |     |     |     |      |
| GTT | ACT | CGC | AGT | GTG | ACT | AAG | CGT | TCA | GTC | ATG | ACG | CTG | GCT | TAC | GGG | 1920 |
| Val | Thr | Arg | Ser | Val | Thr | Lys | Arg | Ser | Val | Met | Thr | Leu | Ala | Tyr | Gly |      |
| 625 |     |     |     | 630 |     |     |     |     | 635 |     |     |     |     |     | 640 |      |
| TCC | AAA | GAG | TTC | GGC | TTC | CGT | CAA | CAA | GTG | CTG | GAA | GAT | ACC | ATT | CAG | 1968 |
| Ser | Lys | Glu | Phe | Gly | Phe | Arg | Gln | Gln | Val | Leu | Glu | Asp | Thr | Ile | Gln |      |
|     |     |     |     | 645 |     |     |     |     | 650 |     |     |     |     | 655 |     |      |
| CCA | GCT | ATT | GAT | TCC | GGC | AAG | GGT | CTG | ATG | TTC | ACT | CAG | CCG | AAT | CAG | 2016 |
| Pro | Ala | Ile | Asp | Ser | Gly | Lys | Gly | Leu | Met | Phe | Thr | Gln | Pro | Asn | Gln |      |
|     |     |     | 660 |     |     |     |     | 665 |     |     |     |     | 670 |     |     |      |
| GCT | GCT | GGA | TAC | ATG | GCT | AAG | CTG | ATT | TGG | GAA | TCT | GTG | AGC | GTG | ACG | 2064 |
| Ala | Ala | Gly | Tyr | Met | Ala | Lys | Leu | Ile | Trp | Glu | Ser | Val | Ser | Val | Thr |      |
|     |     | 675 |     |     |     |     | 680 |     |     |     |     | 685 |     |     |     |      |

| | | | | | | | | | | | | | | | | |
|---|---|---|---|---|---|---|---|---|---|---|---|---|---|---|---|---|
| GTG | GTA | GCT | GCG | GTT | GAA | GCA | ATG | AAC | TGG | CTT | AAG | TCT | GCT | GCT | AAG | 2112 |
| Val | Val 690 | Ala | Ala | Val | Glu 695 | Ala | Met | Asn | Trp | Leu | Lys 700 | Ser | Ala | Ala | Lys | |
| CTG | CTG | GCT | GCT | GAG | GTC | AAA | GAT | AAG | AAG | ACT | GGA | GAG | ATT | CTT | CGC | 2160 |
| Leu 705 | Leu | Ala | Ala | Glu | Val 710 | Lys | Asp | Lys | Lys | Thr 715 | Gly | Glu | Ile | Leu | Arg 720 | |
| AAG | CGT | TGC | GCT | GTG | CAT | TGG | GTA | ACT | CCT | GAT | GGT | TTC | CCT | GTG | TGG | 2208 |
| Lys | Arg | Cys | Ala | Val 725 | His | Trp | Val | Thr | Pro 730 | Asp | Gly | Phe | Pro | Val 735 | Trp | |
| CAG | GAA | TAC | AAG | AAG | CCT | ATT | CAG | ACG | CGC | TTG | AAC | CTG | ATG | TTC | CTC | 2256 |
| Gln | Glu | Tyr | Lys 740 | Lys | Pro | Ile | Gln | Thr 745 | Arg | Leu | Asn | Leu | Met 750 | Phe | Leu | |
| GGT | CAG | TTC | CGC | TTA | CAG | CCT | ACC | ATT | AAC | ACC | AAC | AAA | GAT | AGC | GAG | 2304 |
| Gly | Gln | Phe 755 | Arg | Leu | Gln | Pro | Thr 760 | Ile | Asn | Thr | Asn | Lys 765 | Asp | Ser | Glu | |
| ATT | GAT | GCA | CAC | AAA | CAG | GAG | TCT | GGT | ATC | GCT | CCT | AAC | TTT | GTA | CAC | 2352 |
| Ile | Asp 770 | Ala | His | Lys | Gln | Glu 775 | Ser | Gly | Ile | Ala | Pro 780 | Asn | Phe | Val | His | |
| AGC | CAA | GAC | GGT | AGC | CAC | CTT | CGT | AAG | ACT | GTA | GTG | TGG | GCA | CAC | GAG | 2400 |
| Ser 785 | Gln | Asp | Gly | Ser | His 790 | Leu | Arg | Lys | Thr | Val 795 | Val | Trp | Ala | His | Glu 800 | |
| AAG | TAC | GGA | ATC | GAA | TCT | TTT | GCA | CTG | ATT | CAC | GAC | TCC | TTC | GGT | ACC | 2448 |
| Lys | Tyr | Gly | Ile | Glu 805 | Ser | Phe | Ala | Leu | Ile 810 | His | Asp | Ser | Phe | Gly 815 | Thr | |
| ATT | CCG | GCT | GAC | GCT | GCG | AAC | CTG | TTC | AAA | GCA | GTG | CGC | GAA | ACT | ATG | 2496 |
| Ile | Pro | Ala | Asp 820 | Ala | Ala | Asn | Leu | Phe 825 | Lys | Ala | Val | Arg 830 | Glu | Thr | Met | |
| GTT | GAC | ACA | TAT | GAG | TCT | TGT | GAT | GTA | CTG | GCT | GAT | TTC | TAC | GAC | CAG | 2544 |
| Val | Asp | Thr 835 | Tyr | Glu | Ser | Cys | Asp 840 | Val | Leu | Ala | Asp | Phe 845 | Tyr | Asp | Gln | |
| TTC | GCT | GAC | CAG | TTG | CAC | GAG | TCT | CAA | TTG | GAC | AAA | ATG | CCA | GCA | CTT | 2592 |
| Phe | Ala 850 | Asp | Gln | Leu | His | Glu 855 | Ser | Gln | Leu | Asp | Lys 860 | Met | Pro | Ala | Leu | |
| CCG | GCT | AAA | GGT | AAC | TTG | AAC | CTC | CGT | GAC | ATC | TTA | GAG | TCG | GAC | TTC | 2640 |
| Pro 865 | Ala | Lys | Gly | Asn | Leu 870 | Asn | Leu | Arg | Asp | Ile 875 | Leu | Glu | Ser | Asp | Phe 880 | |
| GCG | TTC | GCG | TAA | 2652 | | | | | | | | | | | | |
| Ala | Phe | Ala 883 | *** | | | | | | | | | | | | | |

( 2 ) INFORMATION FOR SEQ ID NO:2:

( i ) SEQUENCE CHARACTERISTICS:
        ( A ) LENGTH: 883 Amino Acids
        ( B ) TYPE: Amino Acids
        ( C ) STRANDEDNESS: Not Applicable
        ( D ) TOPOLOGY: Not Applicable ( i i ) MOLECULE TYPE: protein ( i i i ) HYPOTHETICAL: No ( i v ) ANTI-SENSE: No ( v ) FRAGMENT TYPE: Entire protein ( v i ) ORIGINAL SOURCE:
        ( A ) ORGANISM: Bacteriophage T7
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pKGP-HA1mut4

(viii) POSITION IN GENOME:
  (A) CHROMOSOME/SEGMENT: Not applicable
  (B) MAP POSITION: Not applicable
  (C) UNITS: Not applicable (ix) FEATURE:
  (A) NAME/KEY: T7 RNA Polymerase GP1(lys222)
  (B) LOCATION: 1 to 883
  (C) IDENTIFICATION METHOD: By expressing and characterizing
      the protein encoded by the gene.
  (D) OTHER INFORMATION: The glu to lys substitution at
      residue 222 alters promoter recognition by the
      T7 RNA polymerase (x) PUBLICATION INFORMATION:
  (A) AUTHORS: Ikeda, R.A., Chang, L.L., and Warshamana, G.S.
  (B) TITLE: Selection and Characterization of a Mutant T7
      RNA Polymerase that Recognizes an Expanded Range
      of T7-like Promoters
  (C) JOURNAL: Biochemistry
  (D) VOLUME: 32
  (E) ISSUE: 35
  (F) PAGES: 9115-9124
  (G) DATE: Sept. 7, 1993
  (H) DOCUMENT NUMBER:
  (I) FILING DATE:
  (J) PUBLICATION DATE:
  (K) RELEVANT RESIDUES IN SEQ ID NO: Amino Acids 1 to
      883 encode the entire T7 RNA polymerase
      GP1(lys222); however, the difference between
      GP1(lys222) and wild-type T7 RNA polymerase is a
      Glu to Lys substitution at residue 222.

(ix) SEQUENCE DESCRIPTION: SEQ ID NO:2:

| Met | Asn | Thr | Ile | Asn | Ile | Ala | Lys | Asn | Asp | Phe | Ser | Asp | Ile | Glu | Leu |
|     |     |     |     | 5   |     |     |     |     | 10  |     |     |     |     | 15  |     |
| Ala | Ala | Ile | Pro | Phe | Asn | Thr | Leu | Ala | Asp | His | Tyr | Gly | Glu | Arg | Leu |
|     |     |     | 20  |     |     |     |     | 25  |     |     |     |     | 30  |     |     |
| Ala | Arg | Glu | Gln | Leu | Ala | Leu | Glu | His | Ser | Tyr | Glu | Met | Gly | Glu |     |
|     |     | 35  |     |     |     |     | 40  |     |     |     | 45  |     |     |     |     |
| Ala | Arg | Phe | Arg | Lys | Met | Phe | Glu | Arg | Gln | Leu | Lys | Ala | Gly | Glu | Val |
|     | 50  |     |     |     |     | 55  |     |     |     |     | 60  |     |     |     |     |
| Ala | Asp | Asn | Ala | Ala | Ala | Lys | Pro | Leu | Ile | Thr | Thr | Leu | Leu | Pro | Lys |
| 65  |     |     |     |     | 70  |     |     |     |     | 75  |     |     |     |     | 80  |
| Met | Ile | Ala | Arg | Ile | Asn | Asp | Trp | Phe | Glu | Glu | Val | Lys | Ala | Lys | Arg |
|     |     |     |     | 85  |     |     |     |     | 90  |     |     |     |     | 95  |     |
| Gly | Lys | Arg | Pro | Thr | Ala | Phe | Gln | Phe | Leu | Gln | Glu | Ile | Lys | Pro | Glu |
|     |     |     | 100 |     |     |     |     | 105 |     |     |     |     | 110 |     |     |
| Ala | Val | Ala | Tyr | Ile | Thr | Ile | Lys | Thr | Thr | Leu | Ala | Cys | Leu | Thr | Ser |
|     |     | 115 |     |     |     |     | 120 |     |     |     |     | 125 |     |     |     |
| Ala | Asp | Asn | Thr | Thr | Val | Gln | Ala | Val | Ala | Ser | Ala | Ile | Gly | Arg | Ala |
|     | 130 |     |     |     |     | 135 |     |     |     |     | 140 |     |     |     |     |
| Ile | Glu | Asp | Glu | Ala | Arg | Phe | Gly | Arg | Ile | Arg | Asp | Leu | Glu | Ala | Lys |
| 145 |     |     |     |     | 150 |     |     |     |     | 155 |     |     |     |     | 160 |
| His | Phe | Lys | Lys | Asn | Val | Glu | Glu | Gln | Leu | Asn | Lys | Arg | Val | Gly | His |
|     |     |     |     | 165 |     |     |     |     | 170 |     |     |     |     | 175 |     |
| Val | Tyr | Lys | Lys | Ala | Phe | Met | Gln | Val | Val | Glu | Ala | Asp | Met | Leu | Ser |
|     |     |     | 180 |     |     |     |     | 185 |     |     |     |     | 190 |     |     |
| Lys | Gly | Leu | Leu | Gly | Gly | Glu | Ala | Trp | Ser | Ser | Trp | His | Lys | Glu | Asp |
|     |     | 195 |     |     |     |     | 200 |     |     |     |     | 205 |     |     |     |
| Ser | Ile | His | Val | Gly | Val | Arg | Cys | Ile | Glu | Met | Leu | Ile | Lys | Ser | Thr |
|     | 210 |     |     |     |     | 215 |     |     |     |     | 220 |     |     |     |     |
| Gly | Met | Val | Ser | Leu | His | Arg | Gln | Asn | Ala | Gly | Val | Val | Gly | Gln | Asp |
| 225 |     |     |     |     | 230 |     |     |     |     | 235 |     |     |     |     | 240 |
| Ser | Glu | Thr | Ile | Glu | Leu | Ala | Pro | Glu | Tyr | Ala | Glu | Ala | Ile | Ala | Thr |

|     | 245 |     |     |     |     |     | 250 |     |     |     |     |     | 255 |     |     |
| --- | --- | --- | --- | --- | --- | --- | --- | --- | --- | --- | --- | --- | --- | --- | --- |

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

```
Val  Val  Ala  Ala  Val  Glu  Ala  Met  Asn  Trp  Leu  Lys  Ser  Ala  Ala  Lys
     690            695                      700

Leu  Leu  Ala  Ala  Glu  Val  Lys  Asp  Lys  Thr  Gly  Glu  Ile  Leu  Arg
705                 710                 715                           720

Lys  Arg  Cys  Ala  Val  His  Trp  Val  Thr  Pro  Asp  Gly  Phe  Pro  Val  Trp
               725                      730                      735

Gln  Glu  Tyr  Lys  Lys  Pro  Ile  Gln  Thr  Arg  Leu  Asn  Leu  Met  Phe  Leu
               740                 745                      750

Gly  Gln  Phe  Arg  Leu  Gln  Pro  Thr  Ile  Asn  Thr  Asn  Lys  Asp  Ser  Glu
          755                      760                 765

Ile  Asp  Ala  His  Lys  Gln  Glu  Ser  Gly  Ile  Ala  Pro  Asn  Phe  Val  His
          770                 775                 780

Ser  Gln  Asp  Gly  Ser  His  Leu  Arg  Lys  Thr  Val  Val  Trp  Ala  His  Glu
785                      790                      795                      800

Lys  Tyr  Gly  Ile  Glu  Ser  Phe  Ala  Leu  Ile  His  Asp  Ser  Phe  Gly  Thr
               805                      810                      815

Ile  Pro  Ala  Asp  Ala  Ala  Asn  Leu  Phe  Lys  Ala  Val  Arg  Glu  Thr  Met
          820                 825                      830

Val  Asp  Thr  Tyr  Glu  Ser  Cys  Asp  Val  Leu  Ala  Asp  Phe  Tyr  Asp  Gln
          835                 840                      845

Phe  Ala  Asp  Gln  Leu  His  Glu  Ser  Gln  Leu  Asp  Lys  Met  Pro  Ala  Leu
     850                      855                 860

Pro  Ala  Lys  Gly  Asn  Leu  Asn  Leu  Arg  Asp  Ile  Leu  Glu  Ser  Asp  Phe
865                      870                 875                           880

Ala  Phe  Ala  ***
          883
```

( 2 ) INFORMATION FOR SEQ ID NO:3:

( i ) SEQUENCE CHARACTERISTICS:
        ( A ) LENGTH: 5096 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pKK232-8

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: Cloning polylinker located between
            nucleotides 177 and 212 and in front of a
            promoterless chloramphicol acetyl transferase
        ( C A T ) gene.
        ( B ) LOCATION: 177 to 212

(C) IDENTIFICATION METHOD: The sequence was provided by
Pharmacia Biotech, Oct. 1989
(D) OTHER INFORMATION:

(x) PUBLICATION INFORMATION:
(A) AUTHORS: Brosius, J. and Lupski, J. R.
(B) TITLE:
(C) JOURNAL: Methods in Enzymology
(D) VOLUME: 153
(E) ISSUE:
(F) PAGES: 54-68
(G) DATE: 1987
(H) DOCUMENT NUMBER:
(I) FILING DATE:
(J) PUBLICATION DATE:
(K) RELEVANT RESIDUES IN SEQ ID NO: 1 to 5096

(ix) SEQUENCE DESCRIPTION: SEQ ID NO:3:

```
TTCCCAGGCA TCAAATAAAA CGAAAGGCTC AGTCGAAAGA CTGGGCCTTT   50
CGTTTTATCT GTTGTTTGTC GGTGAACGCT CTCCTGAGTA GGACAAATCC  100
GCCGGGAGCG GATTTGAACG TTGCGAAGCA ACGGCCCGGA GGGTGGCGGG  150
CAGGACGCCC GCCATAAACT GCCAGGGAAT TCCCGGGGAT CCGTCGACCT  200
GCAGCCAAGC TTGAGTAGGA CAAATCCGCC GAGCTTCGAC GAGATTTTCA  250
GGAGCTAAGG AAGCTAAAAT GGAGAAAAAA ATCACTGGAT ATACCACCGT  300
TGATATATCC CAATCGCATC GTAAAGAACA TTTTGAGGCA TTTCAGTCAG  350
TTGCTCAATG TACCTATAAC CAGACCGTTC AGCTGGATAT TACGGCCTTT  400
TTAAAGACCG TAAAGAAAAA TAAGCACAAG TTTTATCCGG CCTTTATTCA  450
CATTCTTGCC CGCCTGATGA ATGCTCATCC GGAATTCCGT ATGGCAATGA  500
AAGACGGTGA GCTGGTGATA TGGGATAGTG TTCACCCTTG TTACACCGTT  550
TTCCATGAGC AAACTGAAAC GTTTTCATCG CTCTGGAGTG AATACCACGA  600
CGATTTCCGG CAGTTTCTAC ACATATATTC GCAAGATGTG GCGTGTTACG  650
GTGAAAACCT GGCCTATTTC CCTAAAGGGT TTATTGAGAA TATGTTTTTC  700
GTCTCAGCCA ATCCCTGGGT GAGTTTCACC AGTTTTGATT TAAACGTGGC  750
CAATATGGAC AACTTCTTCG CCCCCGTTTT CACCATGGGC AAATATTATA  800
CGCAAGGCGA CAAGGTGCTG ATGCCGCTGG CGATTCAGGT TCATCATGCC  850
GTCTGTGATG GCTTCCATGT CGGCAGAATG CTTAATGAAT TACAACAGTA  900
CTGCGATGAG TGGCAGGGCG GGGCGTAATT TTTTTAAGGC AGTTATTGGT  950
GCCCTTAAAC GCCTGGTGCT ACGCCTGAAT AAGTGATAAT AAGCGGATGA 1000
ATGGCAGAAA TTCGTCGAGG CGGCACCTCG CTAACGGATT CACCACTCCA 1050
AGAATTGGAG CCAATCAATT CTTGCGGAGA ACTGTGAATG CGCAAACCAA 1100
CCCTTGGCAG AACATATCCA TCGCGTCCGC CATCTCCAGC AGCCGCACGC 1150
GGCGCATCTC GGCTGTTTTG GCGGATGAGA GAAGATTTTC AGCCTGATAC 1200
AGATTAAATC AGAACGCAGA AGCGGTCTGA TAAAACAGAA TTTGCCTGGC 1250
GGCAGTAGCG CGGTGGTCCC ACCTGACCCC ATGCCGAACT CAGAAGTGAA 1300
ACGCCGTAGC GCCGATGGTA GTGTGGGGTC TCCCCATGCG AGAGTAGGGA 1350
ACTGCCAGGC ATCAAATAAA ACGAAAGGCT CAGTCGAAAG ACTGGGCCTT 1400
TCGTTTTATC TGTTGTTTGT CGGTGAACGC TCTCCTGAGT AGGACAAATC 1450
CGCCGGGAGC GGATTTGAAC GTTGCGAAGC AACGGCCCGG AGGGTGGCGG 1500
GCAGGACGCC CGCCATAAAC TGCCAGGCAT CAAATTAAGC AGAAGGCCAT 1550
CCTGACGGAT GGCCTTTTTG CGTTTCTACA AACTCTTCCT GTCGTCATAT 1600
```

```
CTACAAGCCA  TCCCCCCACA  GATACGGTAA  ACTAGCCTCG  TTTTTGCATC  1650
AGGAAAGCAG  CTGTTTTGGC  GGATGAGAGA  AGATTTTCAG  CCTGATACAG  1700
ATTAAATCAG  AACGCAGAAG  CGGTCTGATA  AAACAGAATT  TGCCTGGCGG  1750
CAGTAGCGCG  GTGGTCCCAC  CTGACCCCAT  GCCGAACTCA  GAAGTGAAAC  1800
GCCGTAGCGC  CGATGGTAGT  GTGGGGTCTC  CCCATGCGAG  AGTAGGGAAC  1850
TGCCAGGCAT  CAAATAAAAC  GAAAGGCTCA  GTCGAAAGAC  TGGGCCTTTC  1900
GTTTTATCTG  TTGTTTGTCG  GTGAACGCTC  TCCTGAGTAG  GACAAATCCG  1950
CCGGGAGCGG  ATTTGAACGT  TGCGAAGCAA  CGGCCCGGAG  GGTGGCGGGC  2000
AGGACGCCCG  CCATAAACTG  CCAGGCATCA  AATTAAGCAG  AAGGCCATCC  2050
TGACGGATGG  CCTTTTTGCG  TTTCTACAAA  CTCTTCCTGT  CGTCATATCT  2100
ACAAGCCATC  CCCCCACAGA  TACGGTAAAC  TAGCCTCGTT  TTTGCATCAG  2150
GAAAGCAGTC  GGGCAGCGTT  GGGTCCTGGC  CACGGGTGCG  CATGATCGTG  2200
CTCCTGTCGT  TGAGGACCCG  GCTAGGCTGG  CGGGGTTGCC  TTACTGGTTA  2250
GCAGAATGAA  TCACCGATAC  GCGAGCGAAC  GTGAAGCGAC  TGCTGCTGCA  2300
AAACGTCTGC  GACCTGAGCA  ACAACATGAA  TGGTCTTCGG  TTTCCGTGTT  2350
TCGTAAAGTC  TGGAAACGCG  GAAGTCAGCG  CCCTGCACCA  TTATGTTCCG  2400
GATCTGCATC  GCAGGATGCT  GCTGGCTACC  CTGTGGAACA  CCTACATCTG  2450
TATTAACGAA  GCGCTGGCAT  TGACCCTGAG  TGATTTTTCT  CTGGTCCCGC  2500
CGCATCCATA  CCGCCAGTTG  TTTACCCTCA  CAACGTTCCA  GTAACCGGGC  2550
ATGTTCATCA  TCAGTAACCC  GTATCGTGAG  CATCCTCTCT  CGTTTCATCG  2600
GTATCATTAC  CCCCATGAAC  AGAAATTCCC  CCTTACACGG  AGGCATCAAG  2650
TGACCAAACA  GGAAAAAACC  GCCCTTAACA  TGGCCCGCTT  TATCAGAAGC  2700
CAGACATTAA  CGCTTCTGGA  GAAACTCAAC  GAGCTGGACG  CGGATGAACA  2750
GGCAGACATC  TGTGAATCGC  TTCACGACCA  CGCTGATGAG  CTTTACCGCA  2800
GCTGCCTCGC  GCGTTTCGGT  GATGACGGTG  AAAACCTCTG  ACACATGCAG  2850
CTCCCGGAGA  CGGTCACAGC  TTGTCTGTAA  GCGGATGCCG  GGAGCAGACA  2900
AGCCCGTCAG  GGCGCGTCAG  CGGGTGTTGG  CGGGTGTCGG  GGCGCAGCCA  2950
TGACCCAGTC  ACGTAGCGAT  AGCGGAGTGT  ATACTGGCTT  AACTATGCGG  3000
CATCAGAGCA  GATTGTACTG  AGAGTGCACC  ATATGCGGTG  TGAAATACCG  3050
CACAGATGCG  TAAGGAGAAA  ATACCGCATC  AGGCGCTCTT  CCGCTTCCTC  3100
GCTCACTGAC  TCGCTGCGCT  CGGTCGTTCG  GCTGCGGCGA  GCGGTATCAG  3150
CTCACTCAAA  GGCGGTAATA  CGGTTATCCA  CAGAATCAGG  GGATAACGCA  3200
GGAAAGAACA  TGTGAGCAAA  AGGCCAGCAA  AAGGCCAGGA  ACCGTAAAAA  3250
GGCCGCGTTG  CTGGCGTTTT  TCCATAGGCT  CCGCCCCCCT  GACGAGCATC  3300
ACAAAAATCG  ACGCTCAAGT  CAGAGGTGGC  GAAACCCGAC  AGGACTATAA  3350
AGATACCAGG  CGTTTCCCCC  TGGAAGCTCC  CTCGTGCGCT  CTCCTGTTCC  3400
GACCCTGCCG  CTTACCGGAT  ACCTGTCCGC  CTTTCTCCCT  TCGGGAAGCG  3450
TGGCGCTTTC  TCAATGCTCA  CGCTGTAGGT  ATCTCAGTTC  GGTGTAGGTC  3500
GTTCGCTCCA  AGCTGGGCTG  TGTGCACGAA  CCCCCCGTTC  AGCCCGACCG  3550
CTGCGCCTTA  TCCGGTAACT  ATCGTCTTGA  GTCCAACCCG  GTAAGACACG  3600
ACTTATCGCC  ACTGGCAGCA  GCCACTGGTA  ACAGGATTAG  CAGAGCGAGG  3650
```

```
TATGTAGGCG GTGCTACAGA GTTCTTGAAG TGGTGGCCTA ACTACGGCTA    3700
CACTAGAAGG ACAGTATTTG GTATCTGCGC TCTGCTGAAG CCAGTTACCT    3750
TCGGAAAAAG AGTTGGTAGC TCTTGATCCG GCAAACAAAC CACCGCTGGT    3800
AGCGGTGGTT TTTTTGTTTG CAAGCAGCAG ATTACGCGCA GAAAAAAGG     3850
ATCTCAAGAA GATCCTTTGA TCTTTTCTAC GGGGTCTGAC GCTCAGTGGA    3900
ACGAAAACTC ACGTTAAGGG ATTTTGGTCA TGAGATTATC AAAAAGGATC    3950
TTCACCTAGA TCCTTTTAAA TTAAAAATGA AGTTTTAAAT CAATCTAAAG    4000
TATATATGAG TAAACTTGGT CTGACAGTTA CCAATGCTTA ATCAGTGAGG    4050
CACCTATCTC AGCGATCTGT CTATTTCGTT CATCCATAGT TGCCTGACTC    4100
CCCGTCGTGT AGATAACTAC GATACGGGAG GGCTTACCAT CTGGCCCCAG    4150
TGCTGCAATG ATACCGCGAG ACCCACGCTC ACCGGCTCCA GATTTATCAG    4200
CAATAAACCA GCCAGCCGGA AGGGCCGAGC GCAGAAGTGG TCCTGCAACT    4250
TTATCCGCCT CCATCCAGTC TATTAATTGT TGCCGGGAAG CTAGAGTAAG    4300
TAGTTCGCCA GTTAATAGTT TGCGCAACGT TGTTGCCATT GCTGCAGGCA    4350
TCGTGGTGTC ACGCTCGTCG TTTGGTATGG CTTCATTCAG CTCCGGTTCC    4400
CAACGATCAA GGCGAGTTAC ATGATCCCCC ATGTTGTGCA AAAAAGCGGT    4450
TAGCTCCTTC GGTCCTCCGA TCGTTGTCAG AAGTAAGTTG GCCGCAGTGT    4500
TATCACTCAT GGTTATGGCA GCACTGCATA ATTCTCTTAC TGTCATGCCA    4550
TCCGTAAGAT GCTTTTCTGT GACTGGTGAG TACTCAACCA AGTCATTCTG    4600
AGAATAGTGT ATGCGGCGAC CGAGTTGCTC TTGCCCGGCG TCAACACGGG    4650
ATAATACCGC GCCACATAGC AGAACTTTAA AAGTGCTCAT CATTGGAAAA    4700
CGTTCTTCGG GGCGAAAACT CTCAAGGATC TTACCGCTGT TGAGATCCAG    4750
TTCGATGTAA CCCACTCGTG CACCCAACTG ATCTTCAGCA TCTTTTACTT    4800
TCACCAGCGT TTCTGGGTGA GCAAAAACAG GAAGGCAAAA TGCCGCAAAA    4850
AAGGGAATAA GGGCGACACG GAAATGTTGA ATACTCATAC TCTTCCTTTT    4900
TCAATATTAT TGAAGCATTT ATCAGGGTTA TTGTCTCATG AGCGGATACA    4950
TATTTGAATG TATTTAGAAA AATAAACAAA TAGGGGTTCC GCGCACATTT    5000
CCCCGAAAAG TGCCACCTGA CGTCTAAGAA ACCATTATTA TCATGACATT    5050
AACCTATAAA AATAGGCGTA TCACGAGGCC CTTTCGTCTT CAAGAA        5096
```

( 2 ) INFORMATION FOR SEQ ID NO:4:

( i ) SEQUENCE CHARACTERISTICS:
    ( A ) LENGTH: 5110 base pairs
    ( B ) TYPE: nucleic acid
    ( C ) STRANDEDNESS: double
    ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
    ( A ) ORGANISM: Not applicable
    ( B ) STRAIN: Not applicable
    ( C ) INDIVIDUAL ISOLATE: Not applicable
    ( D ) DEVELOPMENTAL STAGE: Not applicable
    ( E ) HAPLOTYPE: Not applicable (F) TISSUE TYPE: Not applicable
(G) CELL TYPE: Not applicable
(H) ORGANELLE: Not applicable (vii) IMMEDIATE SOURCE:
(A) LIBRARY: Not applicable
(B) CLONE: pCM-X#(null)

(viii) POSITION IN GENOME:
(A) CHROMOSOME/SEGMENT: Not applicable
(B) MAP POSITION: Not applicable
(C) UNITS: Not applicable (ix) FEATURE:
(A) NAME/KEY: Potential T7 promoter located between
nucleotides 198 and 220 and in front of a
promoterless chloramphicol acetyl transferase
(CAT) gene.
(B) LOCATION: 198 to 220
(C) IDENTIFICATION METHOD: The general clone was constructed
from pKK232- 8 and randomly mutagenized oligos. The
potential promoters inserted were then sequenced, and
each plasmid was given a different CM-nmerical
assignment..
(D) OTHER INFORMATION: If the potential T7 promoter between
positions 198 and 220 is recognizable by T7 RNA
polymerase then CAT can be expressed from the plasmid.
The lower case bases between positions 198 and 220
indicate that there is a probablility that there is at
least one mutation in this generalized sequence. See the
definition of pCM-X#pyright (c) 1990, Microsoft Corp (x) PUBLICATION INFORMATION:
(A) AUTHORS: Ikeda, R.A., Chang, L.L., and Warshamana, G.S.
(B) TITLE: Selection and Characterization of a Mutant T7
RNA Polymerase that Recognizes an Expanded Range
of T7-like Promoters
(C) JOURNAL: Biochemistry
(D) VOLUME: 32
(E) ISSUE: 35
(F) PAGES: 9115-9124
(G) DATE: Sept. 7, 1993
(H) DOCUMENT NUMBER:
(I) FILING DATE:
(J) PUBLICATION DATE:
(H) DOCUMENT NUMBER:
(I) FILING DATE:
(J) PUBLICATION DATE:
(K) RELEVANT RESIDUES IN SEQ ID NO: 1 to 5110

(ix) SEQUENCE DESCRIPTION: SEQ ID NO:4:

```
TTCCCAGGCA  TCAAATAAAA  CGAAAGGCTC  AGTCGAAAGA  CTGGGCCTTT   50

CGTTTTATCT  GTTGTTTGTC  GGTGAACGCT  CTCCTGAGTA  GGACAAATCC  100

GCCGGGAGCG  GATTTGAACG  TTGCGAAGCA  ACGGCCCGGA  GGGTGGCGGG  150

CAGGACGCCC  GCCATAAACT  GCCAGGGAAT  TCCCCTRR W  W  YYGAAATtaa 200
                                    T7 Promoter Positions    *
                                                            -15 tacgactcac  tatagggaga  AAGCTTGAGT  AGGACAAATC  CGCCGAGCTT  250
    *           *    *
  -10  -5    +1  +5

CGACGAGATT  TTCAGGAGCT  AAGGAAGCTA  AAATGGAGAA  AAAAATCACT  300

GGATATACCA  CCGTTGATAT  ATCCCAATCG  CATCGTAAAG  AACATTTTGA  350

GGCATTTCAG  TCAGTTGCTC  AATGTACCTA  TAACCAGACC  GTTCAGCTGG  400

ATATTACGGC  CTTTTTAAAG  ACCGTAAAGA  AAAATAAGCA  CAAGTTTTAT  450

CCGGCCTTTA  TTCACATTCT  TGCCCGCCTG  ATGAATGCTC  ATCCGGAATT  500

CCGTATGGCA  ATGAAAGACG  GTGAGCTGGT  GATATGGGAT  AGTGTTCACC  550

CTTGTTACAC  CGTTTTCCAT  GAGCAAACTG  AAACGTTTTC  ATCGCTCTGG  600

AGTGAATACC  ACGACGATTT  CCGGCAGTTT  CTACACATAT  ATTCGCAAGA  650
```

-continued

| | | | | |
|---|---|---|---|---|
| TGTGGCGTGT | TACGGTGAAA | ACCTGGCCTA | TTTCCCTAAA | GGGTTTATTG 700 |
| AGAATATGTT | TTTCGTCTCA | GCCAATCCCT | GGGTGAGTTT | CACCAGTTTT 750 |
| GATTTAAACG | TGGCCAATAT | GGACAACTTC | TTCGCCCCCG | TTTTCACCAT 800 |
| GGGCAAATAT | TATACGCAAG | GCGACAAGGT | GCTGATGCCG | CTGGCGATTC 850 |
| AGGTTCATCA | TGCCGTCTGT | GATGGCTTCC | ATGTCGGCAG | AATGCTTAAT 900 |
| GAATTACAAC | AGTACTGCGA | TGAGTGGCAG | GGCGGGGCGT | AATTTTTTA 950 |
| AGGCAGTTAT | TGGTGCCCTT | AAACGCCTGG | TGCTACGCCT | GAATAAGTGA 1000 |
| TAATAAGCGG | ATGAATGGCA | GAAATTCGTC | GAGGCGGCAC | CTCGCTAACG 1050 |
| GATTCACCAC | TCCAAGAATT | GGAGCCAATC | AATTCTTGCG | GAGAACTGTG 1100 |
| AATGCGCAAA | CCAACCCTTG | GCAGAACATA | TCCATCGCGT | CCGCCATCTC 1150 |
| CAGCAGCCGC | ACGCGGCGCA | TCTCGGCTGT | TTTGGCGGAT | GAGAGAAGAT 1200 |
| TTTCAGCCTG | ATACAGATTA | AATCAGAACG | CAGAAGCGGT | CTGATAAAAC 1250 |
| AGAATTTGCC | TGGCGGCAGT | AGCGCGGTGG | TCCCACCTGA | CCCCATGCCG 1300 |
| AACTCAGAAG | TGAAACGCCG | TAGCGCCGAT | GGTAGTGTGG | GGTCTCCCCA 1350 |
| TGCGAGAGTA | GGGAACTGCC | AGGCATCAAA | TAAAACGAAA | GGCTCAGTCG 1400 |
| AAAGACTGGG | CCTTTCGTTT | TATCTGTTGT | TTGTCGGTGA | ACGCTCTCCT 1450 |
| GAGTAGGACA | AATCCGCCGG | GAGCGGATTT | GAACGTTGCG | AAGCAACGGC 1500 |
| CCGGAGGGTG | GCGGGCAGGA | CGCCCGCCAT | AAACTGCCAG | GCATCAAATT 1550 |
| AAGCAGAAGG | CCATCCTGAC | GGATGGCCTT | TTTGCGTTTC | TACAAACTCT 1600 |
| TCCTGTCGTC | ATATCTACAA | GCCATCCCCC | CACAGATACG | GTAAACTAGC 1650 |
| CTCGTTTTTG | CATCAGGAAA | GCAGCTGTTT | TGGCGGATGA | GAGAAGATTT 1700 |
| TCAGCCTGAT | ACAGATTAAA | TCAGAACGCA | GAAGCGGTCT | GATAAACAG 1750 |
| AATTTGCCTG | GCGGCAGTAG | CGCGGTGGTC | CCACCTGACC | CCATGCCGAA 1800 |
| CTCAGAAGTG | AAACGCCGTA | GCGCCGATGG | TAGTGTGGGG | TCTCCCCATG 1850 |
| CGAGAGTAGG | GAACTGCCAG | GCATCAAATA | AAACGAAAGG | CTCAGTCGAA 1900 |
| AGACTGGGCC | TTTCGTTTTA | TCTGTTGTTT | GTCGGTGAAC | GCTCTCCTGA 1950 |
| GTAGGACAAA | TCCGCCGGGA | GCGGATTTGA | ACGTTGCGAA | GCAACGGCCC 2000 |
| GGAGGGTGGC | GGGCAGGACG | CCCGCCATAA | ACTGCCAGGC | ATCAAATTAA 2050 |
| GCAGAAGGCC | ATCCTGACGG | ATGGCCTTTT | TGCGTTTCTA | CAAACTCTTC 2100 |
| CTGTCGTCAT | ATCTACAAGC | CATCCCCCCA | CAGATACGGT | AAACTAGCCT 2150 |
| CGTTTTGCA | TCAGGAAAGC | AGTCGGGCAG | CGTTGGGTCC | TGGCCACGGG 2200 |
| TGCGCATGAT | CGTGCTCCTG | TCGTTGAGGA | CCCGGCTAGG | CTGGCGGGGT 2250 |
| TGCCTTACTG | GTTAGCAGAA | TGAATCACCG | ATACGCGAGC | GAACGTGAAG 2300 |
| CGACTGCTGC | TGCAAAACGT | CTGCGACCTG | AGCAACAACA | TGAATGGTCT 2350 |
| TCGGTTTCCG | TGTTTCGTAA | AGTCTGGAAA | CGCGGAAGTC | AGCGCCCTGC 2400 |
| ACCATTATGT | TCCGGATCTG | CATCGCAGGA | TGCTGCTGGC | TACCCTGTGG 2450 |
| AACACCTACA | TCTGTATTAA | CGAAGCGCTG | GCATTGACCC | TGAGTGATTT 2500 |
| TTCTCTGGTC | CGCCGCATC | CATACCGCCA | GTTGTTTACC | CTCACAACGT 2550 |
| TCCAGTAACC | GGGCATGTTC | ATCATCAGTA | ACCCGTATCG | TGAGCATCCT 2600 |
| CTCTCGTTTC | ATCGGTATCA | TTACCCCCAT | GAACAGAAAT | TCCCCCTTAC 2650 |
| ACGGAGGCAT | CAAGTGACCA | AACAGGAAAA | AACCGCCCTT | AACATGGCCC 2700 |

```
GCTTTATCAG AAGCCAGACA TTAACGCTTC TGGAGAAACT CAACGAGCTG 2750

GACGCGGATG AACAGGCAGA CATCTGTGAA TCGCTTCACG ACCACGCTGA 2800

TGAGCTTTAC CGCAGCTGCC TCGCGCGTTT CGGTGATGAC GGTGAAAACC 2850

TCTGACACAT GCAGCTCCCG GAGACGGTCA CAGCTTGTCT GTAAGCGGAT 2900

GCCGGGAGCA GACAAGCCCG TCAGGGCGCG TCAGCGGGTG TTGGCGGGTG 2950

TCGGGGCGCA GCCATGACCC AGTCACGTAG CGATAGCGGA GTGTATACTG 3000

GCTTAACTAT GCGGCATCAG AGCAGATTGT ACTGAGAGTG CACCATATGC 3050

GGTGTGAAAT ACCGCACAGA TGCGTAAGGA GAAAATACCG CATCAGGCGC 3100

TCTTCCGCTT CCTCGCTCAC TGACTCGCTG CGCTCGGTCG TTCGGCTGCG 3150

GCGAGCGGTA TCAGCTCACT CAAAGGCGGT AATACGGTTA TCCACAGAAT 3200

CAGGGGATAA CGCAGGAAAG AACATGTGAG CAAAAGGCCA GCAAAAGGCC 3250

AGGAACCGTA AAAAGGCCGC GTTGCTGGCG TTTTTCCATA GGCTCCGCCC 3300

CCCTGACGAG CATCACAAAA ATCGACGCTC AAGTCAGAGG TGGCGAAACC 3350

CGACAGGACT ATAAAGATAC CAGGCGTTTC CCCCTGGAAG CTCCCTCGTG 3400

CGCTCTCCTG TTCCGACCCT GCCGCTTACC GGATACCTGT CCGCCTTTCT 3450

CCCTTCGGGA AGCGTGGCGC TTTCTCAATG CTCACGCTGT AGGTATCTCA 3500

GTTCGGTGTA GGTCGTTCGC TCCAAGCTGG GCTGTGTGCA CGAACCCCCC 3550

GTTCAGCCCG ACCGCTGCGC CTTATCCGGT AACTATCGTC TTGAGTCCAA 3600

CCCGGTAAGA CACGACTTAT CGCCACTGGC AGCAGCCACT GGTAACAGGA 3650

TTAGCAGAGC GAGGTATGTA GGCGGTGCTA CAGAGTTCTT GAAGTGGTGG 3700

CCTAACTACG GCTACACTAG AAGGACAGTA TTTGGTATCT GCGCTCTGCT 3750

GAAGCCAGTT ACCTTCGGAA AAAGAGTTGG TAGCTCTTGA TCCGGCAAAC 3800

AAACCACCGC TGGTAGCGGT GGTTTTTTTG TTTGCAAGCA GCAGATTACG 3850

CGCAGAAAAA AAGGATCTCA AGAAGATCCT TTGATCTTTT CTACGGGGTC 3900

TGACGCTCAG TGGAACGAAA ACTCACGTTA AGGGATTTTG GTCATGAGAT 3950

TATCAAAAAG GATCTTCACC TAGATCCTTT TAAATTAAAA ATGAAGTTTT 4000

AAATCAATCT AAAGTATATA TGAGTAAACT TGGTCTGACA GTTACCAATG 4050

CTTAATCAGT GAGGCACCTA TCTCAGCGAT CTGTCTATTT CGTTCATCCA 4100

TAGTTGCCTG ACTCCCCGTC GTGTAGATAA CTACGATACG GGAGGGCTTA 4150

CCATCTGGCC CCAGTGCTGC AATGATACCG CGAGACCCAC GCTCACCGGC 4200

TCCAGATTTA TCAGCAATAA ACCAGCCAGC CGGAAGGGCC GAGCGCAGAA 4250

GTGGTCCTGC AACTTTATCC GCCTCCATCC AGTCTATTAA TTGTTGCCGG 4300

GAAGCTAGAG TAAGTAGTTC GCCAGTTAAT AGTTTGCGCA ACGTTGTTGC 4350

CATTGCTGCA GGCATCGTGG TGTCACGCTC GTCGTTTGGT ATGGCTTCAT 4400

TCAGCTCCGG TTCCCAACGA TCAAGGCGAG TTACATGATC CCCCATGTTG 4450

TGCAAAAAAG CGGTTAGCTC CTTCGGTCCT CCGATCGTTG TCAGAAGTAA 4500

GTTGGCCGCA GTGTTATCAC TCATGGTTAT GGCAGCACTG CATAATTCTC 4550

TTACTGTCAT GCCATCCGTA AGATGCTTTT CTGTGACTGG TGAGTACTCA 4600

ACCAAGTCAT TCTGAGAATA GTGTATGCGG CGACCGAGTT GCTCTTGCCC 4650

GGCGTCAACA CGGGATAATA CCGCGCCACA TAGCAGAACT TTAAAAGTGC 4700

TCATCATTGG AAAACGTTCT TCGGGGCGAA AACTCTCAAG GATCTTACCG 4750
```

```
CTGTTGAGAT  CCAGTTCGAT  GTAACCCACT  CGTGCACCCA  ACTGATCTTC   4800

AGCATCTTTT  ACTTTCACCA  GCGTTTCTGG  GTGAGCAAAA  ACAGGAAGGC   4850

AAAATGCCGC  AAAAAGGGA   ATAAGGGCGA  CACGGAAATG  TTGAATACTC   4900

ATACTCTTCC  TTTTTCAATA  TTATTGAAGC  ATTTATCAGG  GTTATTGTCT   4950

CATGAGCGGA  TACATATTTG  AATGTATTTA  GAAAAATAAA  CAAATAGGGG   5000

TTCCGCGCAC  ATTTCCCCGA  AAAGTGCCAC  CTGACGTCTA  AGAAACCATT   5050

ATTATCATGA  CATTAACCTA  TAAAAATAGG  CGTATCACGA  GGCCCTTTCG   5100

TCTTCAAGAA  5110
```

( 2 ) INFORMATION FOR SEQ ID NO:5:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCAT10-1

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: T7 promoter φ10 located between nucleotides
            198 and 220 and in front of a promoterless
            chloramphicol acetyl transferase (CAT) gene.
        ( B ) LOCATION: 198 to 220
        ( C ) IDENTIFICATION METHOD: The clone was constructed from
            pKK232-8 and the inserted "promoter"was sequenced.
        ( D ) OTHER INFORMATION: The T7 promoter between positions 198
            and 220 is recognizable by T7 RNA polymerase;
            consequently, CAT can be expressed from the plasmid.

( x ) PUBLICATION INFORMATION:
        ( A ) AUTHORS: Ikeda, R.A., Chang, L.L., and Warshamana, G.S.
        ( B ) TITLE: Selection and Characterization of a Mutant T7
            RNA Polymerase that Recognizes an Expanded Range
            of T7-like Promoters
        ( C ) JOURNAL: Biochemistry
        ( D ) VOLUME: 32
        ( E ) ISSUE: 35
        ( F ) PAGES: 9115-9124
        ( G ) DATE: Sept. 7, 1993
        ( H ) DOCUMENT NUMBER:
        ( I ) FILING DATE:
        ( J ) PUBLICATION DATE:
        ( H ) DOCUMENT NUMBER:
        ( I ) FILING DATE:
        ( J ) PUBLICATION DATE:
        ( K ) RELEVANT RESIDUES IN SEQ ID NO: 1 to 5110

( i x ) SEQUENCE DESCRIPTION: SEQ ID NO:5:

```
TTCCCAGGCA  TCAAATAAAA  CGAAAGGCTC  AGTCGAAAGA  CTGGGCCTTT   50
CGTTTTATCT  GTTGTTTGTC  GGTGAACGCT  CTCCTGAGTA  GGACAAATCC  100
GCCGGGAGCG  GATTTGAACG  TTGCGAAGCA  ACGGCCCGGA  GGGTGGCGGG  150
CAGGACGCCC  GCCATAAACT  GCCAGGGAAT  TCCCCTGAAT  TCGAATTAA   200
                        T7 Promoter Positions          •
                                                       -15
TACGACTCAC  TATAGGGAGA  AAGCTTGAGT  AGGACAAATC  CGCCGAGCTT  250
    •    •     •      •
  -10   -5   +1     +5
CGACGAGATT  TTCAGGAGCT  AAGGAAGCTA  AATGGAGAA  AAAAATCACT  300
GGATATACCA  CCGTTGATAT  ATCCCAATCG  CATCGTAAAG  AACATTTTGA  350
GGCATTTCAG  TCAGTTGCTC  AATGTACCTA  TAACCAGACC  GTTCAGCTGG  400
ATATTACGGC  CTTTTTAAAG  ACCGTAAAGA  AAAATAAGCA  CAAGTTTTAT  450
CCGGCCTTTA  TTCACATTCT  TGCCCGCCTG  ATGAATGCTC  ATCCGGAATT  500
CCGTATGGCA  ATGAAAGACG  GTGAGCTGGT  GATATGGGAT  AGTGTTCACC  550
CTTGTTACAC  CGTTTTCCAT  GAGCAAACTG  AAACGTTTTC  ATCGCTCTGG  600
AGTGAATACC  ACGACGATTT  CCGGCAGTTT  CTACACATAT  ATTCGCAAGA  650
TGTGGCGTGT  TACGGTGAAA  ACCTGGCCTA  TTTCCCTAAA  GGGTTTATTG  700
AGAATATGTT  TTCGTCTCA  GCCAATCCCT  GGGTGAGTTT  CACCAGTTTT  750
GATTTAAACG  TGGCCAATAT  GGACAACTTC  TTCGCCCCCG  TTTTCACCAT  800
GGGCAAATAT  TATACGCAAG  GCGACAAGGT  GCTGATGCCG  CTGGCGATTC  850
AGGTTCATCA  TGCCGTCTGT  GATGGCTTCC  ATGTCGGCAG  AATGCTTAAT  900
GAATTACAAC  AGTACTGCGA  TGAGTGGCAG  GGCGGGGCGT  AATTTTTTA   950
AGGCAGTTAT  TGGTGCCCTT  AAACGCCTGG  TGCTACGCCT  GAATAAGTGA  1000
TAATAAGCGG  ATGAATGGCA  GAAATTCGTC  GAGGCGGCAC  CTCGCTAACG  1050
GATTCACCAC  TCCAAGAATT  GGAGCCAATC  AATTCTTGCG  GAGAACTGTG  1100
AATGCGCAAA  CCAACCCTTG  GCAGAACATA  TCCATCGCGT  CCGCCATCTC  1150
CAGCAGCCGC  ACGCGGCGCA  TCTCGGCTGT  TTTGGCGGAT  GAGAGAAGAT  1200
TTTCAGCCTG  ATACAGATTA  AATCAGAACG  CAGAAGCGGT  CTGATAAAAC  1250
AGAATTTGCC  TGGCGGCAGT  AGCGCGGTGG  TCCCACCTGA  CCCCATGCCG  1300
AACTCAGAAG  TGAAACGCCG  TAGCGCCGAT  GGTAGTGTGG  GGTCTCCCCA  1350
TGCGAGAGTA  GGGAACTGCC  AGGCATCAAA  TAAAACGAAA  GGCTCAGTCG  1400
AAAGACTGGG  CCTTTCGTTT  TATCTGTTGT  TTGTCGGTGA  ACGCTCTCCT  1450
GAGTAGGACA  AATCCGCCGG  GAGCGGATTT  GAACGTTGCG  AAGCAACGGC  1500
CCGGAGGGTG  GCGGGCAGGA  CGCCCGCCAT  AAACTGCCAG  GCATCAAATT  1550
AAGCAGAAGG  CCATCCTGAC  GGATGGCCTT  TTTGCGTTTC  TACAAACTCT  1600
TCCTGTCGTC  ATATCTACAA  GCCATCCCCC  CACAGATACG  GTAAACTAGC  1650
CTCGTTTTTG  CATCAGGAAA  GCAGCTGTTT  GGCGGATGA  GAGAAGATTT  1700
TCAGCCTGAT  ACAGATTAAA  TCAGAACGCA  GAAGCGGTCT  GATAAACAG   1750
AATTTGCCTG  GCGGCAGTAG  CGCGGTGGTC  CCACCTGACC  CCATGCCGAA  1800
CTCAGAAGTG  AAACGCCGTA  GCGCCGATGG  TAGTGTGGGG  TCTCCCCATG  1850
CGAGAGTAGG  GAACTGCCAG  GCATCAAATA  AAACGAAAGG  CTCAGTCGAA  1900
AGACTGGGCC  TTTCGTTTTA  TCTGTTGTTT  GTCGGTGAAC  GCTCTCCTGA  1950
```

```
GTAGGACAAA  TCCGCCGGGA  GCGGATTTGA  ACGTTGCGAA  GCAACGGCCC  2000

GGAGGGTGGC  GGGCAGGACG  CCCGCCATAA  ACTGCCAGGC  ATCAAATTAA  2050

GCAGAAGGCC  ATCCTGACGG  ATGGCCTTTT  TGCGTTTCTA  CAAACTCTTC  2100

CTGTCGTCAT  ATCTACAAGC  CATCCCCCCA  CAGATACGGT  AAACTAGCCT  2150

CGTTTTTGCA  TCAGGAAAGC  AGTCGGGCAG  CGTTGGGTCC  TGGCCACGGG  2200

TGCGCATGAT  CGTGCTCCTG  TCGTTGAGGA  CCCGGCTAGG  CTGGCGGGGT  2250

TGCCTTACTG  GTTAGCAGAA  TGAATCACCG  ATACGCGAGC  GAACGTGAAG  2300

CGACTGCTGC  TGCAAAACGT  CTGCGACCTG  AGCAACAACA  TGAATGGTCT  2350

TCGGTTTCCG  TGTTTCGTAA  AGTCTGGAAA  CGCGGAAGTC  AGCGCCCTGC  2400

ACCATTATGT  TCCGGATCTG  CATCGCAGGA  TGCTGCTGGC  TACCCTGTGG  2450

AACACCTACA  TCTGTATTAA  CGAAGCGCTG  GCATTGACCC  TGAGTGATTT  2500

TTCTCTGGTC  CCGCCGCATC  CATACCGCCA  GTTGTTTACC  CTCACAACGT  2550

TCCAGTAACC  GGGCATGTTC  ATCATCAGTA  ACCCGTATCG  TGAGCATCCT  2600

CTCTCGTTTC  ATCGGTATCA  TTACCCCCAT  GAACAGAAAT  TCCCCCTTAC  2650

ACGGAGGCAT  CAAGTGACCA  AACAGGAAAA  AACCGCCCTT  AACATGGCCC  2700

GCTTTATCAG  AAGCCAGACA  TTAACGCTTC  TGGAGAAACT  CAACGAGCTG  2750

GACGCGGATG  AACAGGCAGA  CATCTGTGAA  TCGCTTCACG  ACCACGCTGA  2800

TGAGCTTTAC  CGCAGCTGCC  TCGCGCGTTT  CGGTGATGAC  GGTGAAAACC  2850

TCTGACACAT  GCAGCTCCCG  GAGACGGTCA  CAGCTTGTCT  GTAAGCGGAT  2900

GCCGGGAGCA  GACAAGCCCG  TCAGGGCGCG  TCAGCGGGTG  TTGGCGGGTG  2950

TCGGGGCGCA  GCCATGACCC  AGTCACGTAG  CGATAGCGGA  GTGTATACTG  3000

GCTTAACTAT  GCGGCATCAG  AGCAGATTGT  ACTGAGAGTG  CACCATATGC  3050

GGTGTGAAAT  ACCGCACAGA  TGCGTAAGGA  GAAAATACCG  CATCAGGCGC  3100

TCTTCCGCTT  CCTCGCTCAC  TGACTCGCTG  CGCTCGGTCG  TTCGGCTGCG  3150

GCGAGCGGTA  TCAGCTCACT  CAAAGGCGGT  AATACGGTTA  TCCACAGAAT  3200

CAGGGGATAA  CGCAGGAAAG  AACATGTGAG  CAAAAGGCCA  GCAAAAGGCC  3250

AGGAACCGTA  AAAAGGCCGC  GTTGCTGGCG  TTTTTCCATA  GGCTCCGCCC  3300

CCCTGACGAG  CATCACAAAA  ATCGACGCTC  AAGTCAGAGG  TGGCGAAACC  3350

CGACAGGACT  ATAAAGATAC  CAGGCGTTTC  CCCCTGGAAG  CTCCCTCGTG  3400

CGCTCTCCTG  TTCCGACCCT  GCCGCTTACC  GGATACCTGT  CCGCCTTTCT  3450

CCCTTCGGGA  AGCGTGGCGC  TTTCTCAATG  CTCACGCTGT  AGGTATCTCA  3500

GTTCGGTGTA  GGTCGTTCGC  TCCAAGCTGG  GCTGTGTGCA  CGAACCCCCC  3550

GTTCAGCCCG  ACCGCTGCGC  CTTATCCGGT  AACTATCGTC  TTGAGTCCAA  3600

CCCGGTAAGA  CACGACTTAT  CGCCACTGGC  AGCAGCCACT  GGTAACAGGA  3650

TTAGCAGAGC  GAGGTATGTA  GGCGGTGCTA  CAGAGTTCTT  GAAGTGGTGG  3700

CCTAACTACG  GCTACACTAG  AAGGACAGTA  TTTGGTATCT  GCGCTCTGCT  3750

GAAGCCAGTT  ACCTTCGGAA  AAAGAGTTGG  TAGCTCTTGA  TCCGGCAAAC  3800

AAACCACCGC  TGGTAGCGGT  GGTTTTTTTG  TTTGCAAGCA  GCAGATTACG  3850

CGCAGAAAAA  AAGGATCTCA  AGAAGATCCT  TTGATCTTTT  CTACGGGGTC  3900

TGACGCTCAG  TGGAACGAAA  ACTCACGTTA  AGGGATTTTG  GTCATGAGAT  3950

TATCAAAAAG  GATCTTCACC  TAGATCCTTT  TAAATTAAAA  ATGAAGTTTT  4000
```

| | | | | | |
|---|---|---|---|---|---|
|AAATCAATCT|AAAGTATATA|TGAGTAAACT|TGGTCTGACA|GTTACCAATG|4050|
|CTTAATCAGT|GAGGCACCTA|TCTCAGCGAT|CTGTCTATTT|CGTTCATCCA|4100|
|TAGTTGCCTG|ACTCCCGTC|GTGTAGATAA|CTACGATACG|GGAGGGCTTA|4150|
|CCATCTGGCC|CCAGTGCTGC|AATGATACCG|CGAGACCCAC|GCTCACCGGC|4200|
|TCCAGATTTA|TCAGCAATAA|ACCAGCCAGC|CGGAAGGGCC|GAGCGCAGAA|4250|
|GTGGTCCTGC|AACTTATCC|GCCTCCATCC|AGTCTATTAA|TTGTTGCCGG|4300|
|GAAGCTAGAG|TAAGTAGTTC|GCCAGTTAAT|AGTTTGCGCA|ACGTTGTTGC|4350|
|CATTGCTGCA|GGCATCGTGG|TGTCACGCTC|GTCGTTTGGT|ATGGCTTCAT|4400|
|TCAGCTCCGG|TTCCCAACGA|TCAAGGCGAG|TTACATGATC|CCCCATGTTG|4450|
|TGCAAAAAAG|CGGTTAGCTC|CTTCGGTCCT|CCGATCGTTG|TCAGAAGTAA|4500|
|GTTGGCCGCA|GTGTTATCAC|TCATGGTTAT|GGCAGCACTG|CATAATTCTC|4550|
|TTACTGTCAT|GCCATCCGTA|AGATGCTTTT|CTGTGACTGG|TGAGTACTCA|4600|
|ACCAAGTCAT|TCTGAGAATA|GTGTATGCGG|CGACCGAGTT|GCTCTTGCCC|4650|
|GGCGTCAACA|CGGGATAATA|CCGCGCCACA|TAGCAGAACT|TTAAAAGTGC|4700|
|TCATCATTGG|AAAACGTTCT|TCGGGGCGAA|AACTCTCAAG|GATCTTACCG|4750|
|CTGTTGAGAT|CCAGTTCGAT|GTAACCCACT|CGTGCACCCA|ACTGATCTTC|4800|
|AGCATCTTTT|ACTTTCACCA|GCGTTTCTGG|GTGAGCAAAA|ACAGGAAGGC|4850|
|AAAATGCCGC|AAAAAAGGGA|ATAAGGGCGA|CACGGAAATG|TTGAATACTC|4900|
|ATACTCTTCC|TTTTTCAATA|TTATTGAAGC|ATTTATCAGG|GTTATTGTCT|4950|
|CATGAGCGGA|TACATATTTG|AATGTATTTA|GAAAAATAAA|CAAATAGGGG|5000|
|TTCCGCGCAC|ATTTCCCCGA|AAAGTGCCAC|CTGACGTCTA|AGAAACCATT|5050|
|ATTATCATGA|CATTAACCTA|TAAAAATAGG|CGTATCACGA|GGCCCTTTCG|5100|
|TCTTCAAGAA|5110| | | | |

( 2 ) INFORMATION FOR SEQ ID NO:6:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCM-T297

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
  ( A ) NAME/KEY: Inactive T7 φ10 promoter mutant (-11G to T)
    located between nucleotides 198 and 220 and in front of
    a promoterless chloramphicol acetyl transferase (CAT)
    gene.
  ( B ) LOCATION: 198 to 220
  ( C ) IDENTIFICATION METHOD: The clone was constructed from
    pKK232-8 and the inserted "promoter" was sequenced.
  ( D ) OTHER INFORMATION: If the mutant T7 promoter between
    positions 198 and 220 is recognizable by T7 RNA
    polymerase or a mutant T7 RNA polymerase, CAT can be
    expressed from the plasmid.

( x ) PUBLICATION INFORMATION:
  ( A ) AUTHORS: Ikeda, R.A., Chang, L.L., and Warshamana, G.S.
  ( B ) TITLE: Selection and Characterization of a Mutant T7
    RNA Polymerase that Recognizes an Expanded Range
    of T7-like Promoters
  ( C ) JOURNAL: Biochemistry
  ( D ) VOLUME: 32
  ( E ) ISSUE: 35
  ( F ) PAGES: 9115-9124
  ( G ) DATE: Sept. 7, 1993
  ( H ) DOCUMENT NUMBER:
  ( I ) FILING DATE:
  ( J ) PUBLICATION DATE:
  ( H ) DOCUMENT NUMBER:
  ( I ) FILING DATE:
  ( J ) PUBLICATION DATE:
  ( K ) RELEVANT RESIDUES IN SEQ ID NO: 1 to 5110

( i x ) SEQUENCE DESCRIPTION: SEQ ID NO:6:

```
TTCCCAGGCA  TCAAATAAAA  CGAAAGGCTC  AGTCGAAAGA  CTGGGCCTTT   50

CGTTTTATCT  GTTGTTTGTC  GGTGAACGCT  CTCCTGAGTA  GGACAAATCC  100

GCCGGGAGCG  GATTTGAACG  TTGCGAAGCA  ACGGCCCGGA  GGGTGGCGGG  150

CAGGACGCCC  GCCATAAACT  GCCAGGGAAT  TCCCCTAGTA  CTGAAATTAA  200
                                T7 Promoter Positions      *
                                                          -15

TACTACTCAC  TATAGGGAGA  AAGCTTGAGT  AGGACAAATC  CGCCGAGCTT  250
    *         *    *
   -10       -5   +1  +5

CGACGAGATT  TTCAGGAGCT  AAGGAAGCTA  AAATGGAGAA  AAAAATCACT  300

GGATATACCA  CCGTTGATAT  ATCCCAATCG  CATCGTAAAG  AACATTTTGA  350

GGCATTTCAG  TCAGTTGCTC  AATGTACCTA  TAACCAGACC  GTTCAGCTGG  400

ATATTACGGC  CTTTTAAAG  ACCGTAAAGA  AAAATAAGCA  CAAGTTTTAT  450

CCGGCCTTTA  TTCACATTCT  TGCCCGCCTG  ATGAATGCTC  ATCCGGAATT  500

CCGTATGGCA  ATGAAAGACG  GTGAGCTGGT  GATATGGGAT  AGTGTTCACC  550

CTTGTTACAC  CGTTTTCCAT  GAGCAAACTG  AAACGTTTTC  ATCGCTCTGG  600

AGTGAATACC  ACGACGATTT  CCGGCAGTTT  CTACACATAT  ATTCGCAAGA  650

TGTGGCGTGT  TACGGTGAAA  ACCTGGCCTA  TTTCCCTAAA  GGGTTTATTG  700

AGAATATGTT  TTTCGTCTCA  GCCAATCCCT  GGGTGAGTTT  CACCAGTTTT  750

GATTTAAACG  TGGCCAATAT  GGACAACTTC  TTCGCCCCCG  TTTTCACCAT  800

GGGCAAATAT  TATACGCAAG  GCGACAAGGT  GCTGATGCCG  CTGGCGATTC  850

AGGTTCATCA  TGCCGTCTGT  GATGGCTTCC  ATGTCGGCAG  AATGCTTAAT  900

GAATTACAAC  AGTACTGCGA  TGAGTGGCAG  GGCGGGGCGT  AATTTTTTA  950

AGGCAGTTAT  TGGTGCCCTT  AAACGCCTGG  TGCTACGCCT  GAATAAGTGA 1000

TAATAAGCGG  ATGAATGGCA  GAAATTCGTC  GAGGCGGCAC  CTCGCTAACG 1050

GATTCACCAC  TCCAAGAATT  GGAGCCAATC  AATTCTTGCG  GAGAACTGTG 1100
```

| | | | | |
|---|---|---|---|---|
| AATGCGCAAA | CCAACCCTTG | GCAGAACATA | TCCATCGCGT | CCGCCATCTC 1150 |
| CAGCAGCCGC | ACGCGGCGCA | TCTCGGCTGT | TTTGGCGGAT | GAGAGAAGAT 1200 |
| TTTCAGCCTG | ATACAGATTA | AATCAGAACG | CAGAAGCGGT | CTGATAAAAC 1250 |
| AGAATTTGCC | TGGCGGCAGT | AGCGCGGTGG | TCCCACCTGA | CCCCATGCCG 1300 |
| AACTCAGAAG | TGAAACGCCG | TAGCGCCGAT | GGTAGTGTGG | GGTCTCCCCA 1350 |
| TGCGAGAGTA | GGGAACTGCC | AGGCATCAAA | TAAAACGAAA | GGCTCAGTCG 1400 |
| AAAGACTGGG | CCTTTCGTTT | TATCTGTTGT | TTGTCGGTGA | ACGCTCTCCT 1450 |
| GAGTAGGACA | AATCCGCCGG | GAGCGGATTT | GAACGTTGCG | AAGCAACGGC 1500 |
| CCGGAGGGTG | GCGGGCAGGA | CGCCCGCCAT | AAACTGCCAG | GCATCAAATT 1550 |
| AAGCAGAAGG | CCATCCTGAC | GGATGGCCTT | TTTGCGTTTC | TACAAACTCT 1600 |
| TCCTGTCGTC | ATATCTACAA | GCCATCCCCC | CACAGATACG | GTAAACTAGC 1650 |
| CTCGTTTTTG | CATCAGGAAA | GCAGCTGTTT | GGCGGATGA | GAAGATTT 1700 |
| TCAGCCTGAT | ACAGATTAAA | TCAGAACGCA | GAAGCGGTCT | GATAAACAG 1750 |
| AATTTGCCTG | GCGGCAGTAG | CGCGGTGGTC | CCACCTGACC | CCATGCCGAA 1800 |
| CTCAGAAGTG | AAACGCCGTA | GCGCCGATGG | TAGTGTGGGG | TCTCCCCATG 1850 |
| CGAGAGTAGG | GAACTGCCAG | GCATCAAATA | AAACGAAAGG | CTCAGTCGAA 1900 |
| AGACTGGGCC | TTTCGTTTTA | TCTGTTGTTT | GTCGGTGAAC | GCTCTCCTGA 1950 |
| GTAGGACAAA | TCCGCCGGGA | GCGGATTTGA | ACGTTGCGAA | GCAACGGCCC 2000 |
| GGAGGGTGGC | GGGCAGGACG | CCCGCCATAA | ACTGCCAGGC | ATCAAATTAA 2050 |
| GCAGAAGGCC | ATCCTGACGG | ATGGCCTTTT | TGCGTTTCTA | CAAACTCTTC 2100 |
| CTGTCGTCAT | ATCTACAAGC | CATCCCCCCA | CAGATACGGT | AAACTAGCCT 2150 |
| CGTTTTTGCA | TCAGGAAAGC | AGTCGGGCAG | CGTTGGGTCC | TGGCCACGGG 2200 |
| TGCGCATGAT | CGTGCTCCTG | TCGTTGAGGA | CCCGGCTAGG | CTGGCGGGGT 2250 |
| TGCCTTACTG | GTTAGCAGAA | TGAATCACCG | ATACGCGAGC | GAACGTGAAG 2300 |
| CGACTGCTGC | TGCAAAACGT | CTGCGACCTG | AGCAACAACA | TGAATGGTCT 2350 |
| TCGGTTTCCG | TGTTTCGTAA | AGTCTGGAAA | CGCGGAAGTC | AGCGCCCTGC 2400 |
| ACCATTATGT | TCCGGATCTG | CATCGCAGGA | TGCTGCTGGC | TACCCTGTGG 2450 |
| AACACCTACA | TCTGTATTAA | CGAAGCGCTG | GCATTGACCC | TGAGTGATTT 2500 |
| TTCTCTGGTC | CCGCCGCATC | CATACCGCCA | GTTGTTTACC | CTCACAACGT 2550 |
| TCCAGTAACC | GGGCATGTTC | ATCATCAGTA | ACCCGTATCG | TGAGCATCCT 2600 |
| CTCTCGTTTC | ATCGGTATCA | TTACCCCCAT | GAACAGAAAT | TCCCCCTTAC 2650 |
| ACGGAGGCAT | CAAGTGACCA | AACAGGAAAA | AACCGCCCTT | AACATGGCCC 2700 |
| GCTTTATCAG | AAGCCAGACA | TTAACGCTTC | TGGAGAAACT | CAACGAGCTG 2750 |
| GACGCGGATG | AACAGGCAGA | CATCTGTGAA | TCGCTTCACG | ACCACGCTGA 2800 |
| TGAGCTTTAC | CGCAGCTGCC | TCGCGCGTTT | CGGTGATGAC | GGTGAAAACC 2850 |
| TCTGACACAT | GCAGCTCCCG | GAGACGGTCA | CAGCTTGTCT | GTAAGCGGAT 2900 |
| GCCGGGAGCA | GACAAGCCCG | TCAGGGCGCG | TCAGCGGGTG | TTGGCGGGTG 2950 |
| TCGGGGCGCA | GCCATGACCC | AGTCACGTAG | CGATAGCGGA | GTGTATACTG 3000 |
| GCTTAACTAT | GCGGCATCAG | AGCAGATTGT | ACTGAGAGTG | CACCATATGC 3050 |
| GGTGTGAAAT | ACCGCACAGA | TGCGTAAGGA | GAAAATACCG | CATCAGGCGC 3100 |
| TCTTCCGCTT | CCTCGCTCAC | TGACTCGCTG | CGCTCGGTCG | TTCGGCTGCG 3150 |

```
GCGAGCGGTA TCAGCTCACT CAAAGGCGGT AATACGGTTA TCCACAGAAT  3200
CAGGGGATAA CGCAGGAAAG AACATGTGAG CAAAAGGCCA GCAAAAGGCC  3250
AGGAACCGTA AAAAGGCCGC GTTGCTGGCG TTTTTCCATA GGCTCCGCCC  3300
CCCTGACGAG CATCACAAAA ATCGACGCTC AAGTCAGAGG TGGCGAAACC  3350
CGACAGGACT ATAAAGATAC CAGGCGTTTC CCCTGGAAG CTCCCTCGTG   3400
CGCTCTCCTG TTCCGACCCT GCCGCTTACC GGATACCTGT CCGCCTTTCT  3450
CCCTTCGGGA AGCGTGGCGC TTTCTCAATG CTCACGCTGT AGGTATCTCA  3500
GTTCGGTGTA GGTCGTTCGC TCCAAGCTGG GCTGTGTGCA CGAACCCCCC  3550
GTTCAGCCCG ACCGCTGCGC CTTATCCGGT AACTATCGTC TTGAGTCCAA  3600
CCCGGTAAGA CACGACTTAT CGCCACTGGC AGCAGCCACT GGTAACAGGA  3650
TTAGCAGAGC GAGGTATGTA GGCGGTGCTA CAGAGTTCTT GAAGTGGTGG  3700
CCTAACTACG GCTACACTAG AAGGACAGTA TTTGGTATCT GCGCTCTGCT  3750
GAAGCCAGTT ACCTTCGGAA AAAGAGTTGG TAGCTCTTGA TCCGGCAAAC  3800
AAACCACCGC TGGTAGCGGT GGTTTTTTG TTTGCAAGCA GCAGATTACG   3850
CGCAGAAAAA AAGGATCTCA AGAAGATCCT TTGATCTTTT CTACGGGGTC  3900
TGACGCTCAG TGGAACGAAA ACTCACGTTA AGGGATTTTG GTCATGAGAT  3950
TATCAAAAAG GATCTTCACC TAGATCCTTT TAAATTAAAA ATGAAGTTTT  4000
AAATCAATCT AAAGTATATA TGAGTAAACT TGGTCTGACA GTTACCAATG  4050
CTTAATCAGT GAGGCACCTA TCTCAGCGAT CTGTCTATTT CGTTCATCCA  4100
TAGTTGCCTG ACTCCCCGTC GTGTAGATAA CTACGATACG GGAGGGCTTA  4150
CCATCTGGCC CCAGTGCTGC AATGATACCG CGAGACCCAC GCTCACCGGC  4200
TCCAGATTTA TCAGCAATAA ACCAGCCAGC CGGAAGGGCC GAGCGCAGAA  4250
GTGGTCCTGC AACTTTATCC GCCTCCATCC AGTCTATTAA TTGTTGCCGG  4300
GAAGCTAGAG TAAGTAGTTC GCCAGTTAAT AGTTTGCGCA ACGTTGTTGC  4350
CATTGCTGCA GGCATCGTGG TGTCACGCTC GTCGTTTGGT ATGGCTTCAT  4400
TCAGCTCCGG TTCCCAACGA TCAAGGCGAG TTACATGATC CCCCATGTTG  4450
TGCAAAAAAG CGGTTAGCTC CTTCGGTCCT CCGATCGTTG TCAGAAGTAA  4500
GTTGGCCGCA GTGTTATCAC TCATGGTTAT GGCAGCACTG CATAATTCTC  4550
TTACTGTCAT GCCATCCGTA AGATGCTTTT CTGTGACTGG TGAGTACTCA  4600
ACCAAGTCAT TCTGAGAATA GTGTATGCGG CGACCGAGTT GCTCTTGCCC  4650
GGCGTCAACA CGGGATAATA CCGCGCCACA TAGCAGAACT TTAAAAGTGC  4700
TCATCATTGG AAAACGTTCT TCGGGGCGAA AACTCTCAAG GATCTTACCG  4750
CTGTTGAGAT CCAGTTCGAT GTAACCCACT CGTGCACCCA ACTGATCTTC  4800
AGCATCTTTT ACTTTCACCA GCGTTTCTGG GTGAGCAAAA ACAGGAAGGC  4850
AAAATGCCGC AAAAAAGGGA ATAAGGGCGA CACGGAAATG TTGAATACTC  4900
ATACTCTTCC TTTTTCAATA TTATTGAAGC ATTTATCAGG GTTATTGTCT  4950
CATGAGCGGA TACATATTTG AATGTATTTA GAAAAATAAA CAAATAGGGG  5000
TTCCGCGCAC ATTTCCCCGA AAAGTGCCAC CTGACGTCTA AGAAACCATT  5050
ATTATCATGA CATTAACCTA TAAAAATAGG CGTATCACGA GGCCCTTTCG  5100
TCTTCAAGAA 5110
```

( 2 ) INFORMATION FOR SEQ ID NO:7:

(i) SEQUENCE CHARACTERISTICS:
     (A) LENGTH: 5110 base pairs
     (B) TYPE: nucleic acid
     (C) STRANDEDNESS: double
     (D) TOPOLOGY: circular (ii) MOLECULE TYPE: other nucleic acid (iii) HYPOTHETICAL: No (iv) ANTI-SENSE: No (v) FRAGMENT TYPE: Not applicable (vi) ORIGINAL SOURCE:
     (A) ORGANISM: Not applicable
     (B) STRAIN: Not applicable
     (C) INDIVIDUAL ISOLATE: Not applicable
     (D) DEVELOPMENTAL STAGE: Not applicable
     (E) HAPLOTYPE: Not applicable
     (F) TISSUE TYPE: Not applicable
     (G) CELL TYPE: Not applicable
     (H) ORGANELLE: Not applicable (vii) IMMEDIATE SOURCE:
     (A) LIBRARY: Not applicable
     (B) CLONE: pCM-P1160

(viii) POSITION IN GENOME:
     (A) CHROMOSOME/SEGMENT: Not applicable
     (B) MAP POSITION: Not applicable
     (C) UNITS: Not applicable (ix) FEATURE:
     (A) NAME/KEY: Inactive T7 φ10 promoter mutant (-9C to G)
          located between nucleotides 198 and 220 and in front of
          a promoterless chloramphicol acetyl transferase (CAT)
          gene.
     (B) LOCATION: 198 to 220
     (C) IDENTIFICATION METHOD: The clone was constructed from
          pKK232-8 and the inserted "promoter" was sequenced.
     (D) OTHER INFORMATION: If the mutant T7 promoter between
          positions 198 and 220 is recognizable by T7 RNA
          polymerase or a mutant T7 RNA polymerase, CAT can be
          expressed from the plasmid.

(x) PUBLICATION INFORMATION:
     (A) AUTHORS: Ikeda, R.A., Chang, L.L., and Warshamana, G.S.
     (B) TITLE: Selection and Characterization of a Mutant T7
          RNA Polymerase that Recognizes an Expanded Range
          of T7-like Promoters
     (C) JOURNAL: Biochemistry
     (D) VOLUME: 32
     (E) ISSUE: 35
     (F) PAGES: 9115-9124
     (G) DATE: Sept. 7, 1993
     (H) DOCUMENT NUMBER:
     (I) FILING DATE:
     (J) PUBLICATION DATE:
     (H) DOCUMENT NUMBER:
     (I) FILING DATE:
     (J) PUBLICATION DATE:
     (K) RELEVANT RESIDUES IN SEQ ID NO: 1 to 5110

(ix) SEQUENCE DESCRIPTION: SEQ ID NO:7:

```
TTCCCAGGCA  TCAAATAAAA  CGAAAGGCTC  AGTCGAAAGA  CTGGGCCTTT   50

CGTTTTATCT  GTTGTTTGTC  GGTGAACGCT  CTCCTGAGTA  GGACAAATCC  100

GCCGGGAGCG  GATTTGAACG  TTGCGAAGCA  ACGGCCCGGA  GGGTGGCGGG  150

CAGGACGCCC  GCCATAAACT  GCCAGGGAAT  TCCCCTAGTA  CTGAAATTAA  200
                                T7  Promoter  Positions      *
                                                            -15

TACGAGTCAC  TATAGGGAGA  AAGCTTGAGT  AGGACAAATC  CGCCGAGCTT  250
    *    *       *    *
  -10  -5      +1   +5

CGACGAGATT  TTCAGGAGCT  AAGGAAGCTA  AAATGGAGAA  AAAAATCACT  300
```

```
GGATATACCA CCGTTGATAT ATCCCAATCG CATCGTAAAG AACATTTTGA  350
GGCATTTCAG TCAGTTGCTC AATGTACCTA TAACCAGACC GTTCAGCTGG  400
ATATTACGGC CTTTTTAAAG ACCGTAAAGA AAAATAAGCA CAAGTTTTAT  450
CCGGCCTTTA TTCACATTCT TGCCCGCCTG ATGAATGCTC ATCCGGAATT  500
CCGTATGGCA ATGAAAGACG GTGAGCTGGT GATATGGGAT AGTGTTCACC  550
CTTGTTACAC CGTTTTCCAT GAGCAAACTG AAACGTTTTC ATCGCTCTGG  600
AGTGAATACC ACGACGATTT CCGGCAGTTT CTACACATAT ATTCGCAAGA  650
TGTGGCGTGT TACGGTGAAA ACCTGGCCTA TTTCCCTAAA GGGTTTATTG  700
AGAATATGTT TTTCGTCTCA GCCAATCCCT GGGTGAGTTT CACCAGTTTT  750
GATTTAAACG TGGCCAATAT GGACAACTTC TTCGCCCCCG TTTTCACCAT  800
GGGCAAATAT TATACGCAAG CGACAAGGT GCTGATGCCG CTGGCGATTC  850
AGGTTCATCA TGCCGTCTGT GATGGCTTCC ATGTCGGCAG AATGCTTAAT  900
GAATTACAAC AGTACTGCGA TGAGTGGCAG GGCGGGGCGT AATTTTTTA  950
AGGCAGTTAT TGGTGCCCTT AAACGCCTGG TGCTACGCCT GAATAAGTGA 1000
TAATAAGCGG ATGAATGGCA GAAATTCGTC GAGGCGGCAC CTCGCTAACG 1050
GATTCACCAC TCCAAGAATT GGAGCCAATC AATTCTTGCG GAGAACTGTG 1100
AATGCGCAAA CCAACCCTTG GCAGAACATA TCCATCGCGT CCGCCATCTC 1150
CAGCAGCCGC ACGCGGCGCA TCTCGGCTGT TTTGGCGGAT GAGAGAAGAT 1200
TTTCAGCCTG ATACAGATTA AATCAGAACG CAGAAGCGG CTGATAAAAC 1250
AGAATTTGCC TGGCGGCAGT AGCGCGGTGG TCCCACCTGA CCCCATGCCG 1300
AACTCAGAAG TGAAACGCCG TAGCGCCGAT GGTAGTGTGG GGTCTCCCCA 1350
TGCGAGAGTA GGGAACTGCC AGGCATCAAA TAAAACGAAA GGCTCAGTCG 1400
AAAGACTGGG CCTTTCGTTT TATCTGTTGT TTGTCGGTGA ACGCTCTCCT 1450
GAGTAGGACA AATCCGCCGG GAGCGGATTT GAACGTTGCG AAGCAACGGC 1500
CCGGAGGGTG GCGGGCAGGA CGCCCGCCAT AAACTGCCAG GCATCAAATT 1550
AAGCAGAAGG CCATCCTGAC GGATGGCCTT TTTGCGTTTC TACAAACTCT 1600
TCCTGTCGTC ATATCTACAA GCCATCCCCC CACAGATACG GTAAACTAGC 1650
CTCGTTTTTG CATCAGGAAA GCAGCTGTTT GGCGGATGA GAGAAGATTT 1700
TCAGCCTGAT ACAGATTAAA TCAGAACGCA GAAGCGGTCT GATAAAACAG 1750
AATTTGCCTG GCGGCAGTAG CGCGGTGGTC CCACCTGACC CCATGCCGAA 1800
CTCAGAAGTG AAACGCCGTA GCGCCGATGG TAGTGTGGG TCTCCCCATG 1850
CGAGAGTAGG GAACTGCCAG GCATCAAATA AAACGAAAGG CTCAGTCGAA 1900
AGACTGGGCC TTTCGTTTTA TCTGTTGTTT GTCGGTGAAC GCTCTCCTGA 1950
GTAGGACAAA TCCGCCGGGA GCGGATTTGA ACGTTGCGAA GCAACGGCCC 2000
GGAGGGTGGC GGGCAGGACG CCCGCCATAA ACTGCCAGGC ATCAAATTAA 2050
GCAGAAGGCC ATCCTGACGG ATGGCCTTTT TGCGTTTCTA CAAACTCTTC 2100
CTGTCGTCAT ATCTACAAGC CATCCCCCCA CAGATACGGT AAACTAGCCT 2150
CGTTTTTGCA TCAGGAAAGC AGTCGGGCAG CGTTGGGTCC TGGCCACGGG 2200
TGCGCATGAT CGTGCTCCTG TCGTTGAGGA CCCGGCTAGG CTGGCGGGGT 2250
TGCCTTACTG GTTAGCAGAA TGAATCACCG ATACGCGAGC GAACGTGAAG 2300
CGACTGCTGC TGCAAAACGT CTGCGACCTG AGCAACAACA TGAATGGTCT 2350
```

```
TCGGTTTCCG TGTTTCGTAA AGTCTGGAAA CGCGGAAGTC AGCGCCCTGC 2400
ACCATTATGT TCCGGATCTG CATCGCAGGA TGCTGCTGGC TACCCTGTGG 2450
AACACCTACA TCTGTATTAA CGAAGCGCTG GCATTGACCC TGAGTGATTT 2500
TTCTCTGGTC CCGCCGCATC CATACCGCCA GTTGTTTACC CTCACAACGT 2550
TCCAGTAACC GGGCATGTTC ATCATCAGTA ACCCGTATCG TGAGCATCCT 2600
CTCTCGTTTC ATCGGTATCA TTACCCCAT GAACAGAAAT TCCCCCTTAC 2650
ACGGAGGCAT CAAGTGACCA AACAGGAAAA AACCGCCCTT AACATGGCCC 2700
GCTTTATCAG AAGCCAGACA TTAACGCTTC TGGAGAAACT CAACGAGCTG 2750
GACGCGGATG AACAGGCAGA CATCTGTGAA TCGCTTCACG ACCACGCTGA 2800
TGAGCTTTAC CGCAGCTGCC TCGCGCGTTT CGGTGATGAC GGTGAAAACC 2850
TCTGACACAT GCAGCTCCCG GAGACGGTCA CAGCTTGTCT GTAAGCGGAT 2900
GCCGGGAGCA GACAAGCCCG TCAGGGCGCG TCAGCGGGTG TTGCGGGTG 2950
TCGGGGCGCA GCCATGACCC AGTCACGTAG CGATAGCGGA GTGTATACTG 3000
GCTTAACTAT GCGGCATCAG AGCAGATTGT ACTGAGAGTG CACCATATGC 3050
GGTGTGAAAT ACCGCACAGA TGCGTAAGGA GAAAATACCG CATCAGGCGC 3100
TCTTCCGCTT CCTCGCTCAC TGACTCGCTG CGCTCGGTCG TTCGGCTGCG 3150
GCGAGCGGTA TCAGCTCACT CAAAGGCGGT AATACGGTTA TCCACAGAAT 3200
CAGGGGATAA CGCAGGAAAG AACATGTGAG CAAAAGGCCA GCAAAAGGCC 3250
AGGAACCGTA AAAAGGCCGC GTTGCTGGCG TTTTTCCATA GGCTCCGCCC 3300
CCCTGACGAG CATCACAAAA ATCGACGCTC AAGTCAGAGG TGGCGAAACC 3350
CGACAGGACT ATAAAGATAC CAGGCGTTTC CCCCTGGAAG CTCCCTCGTG 3400
CGCTCTCCTG TTCCGACCCT GCCGCTTACC GGATACCTGT CCGCCTTTCT 3450
CCCTTCGGGA AGCGTGGCGC TTTCTCAATG CTCACGCTGT AGGTATCTCA 3500
GTTCGGTGTA GGTCGTTCGC TCCAAGCTGG GCTGTGTGCA CGAACCCCCC 3550
GTTCAGCCCG ACCGCTGCGC CTTATCCGGT AACTATCGTC TTGAGTCCAA 3600
CCCGGTAAGA CACGACTTAT CGCCACTGGC AGCAGCCACT GGTAACAGGA 3650
TTAGCAGAGC GAGGTATGTA GGCGGTGCTA CAGAGTTCTT GAAGTGGTGG 3700
CCTAACTACG GCTACACTAG AAGGACAGTA TTTGGTATCT GCGCTCTGCT 3750
GAAGCCAGTT ACCTTCGGAA AAAGAGTTGG TAGCTCTTGA TCCGGCAAAC 3800
AAACCACCGC TGGTAGCGGT GGTTTTTTTG TTTGCAAGCA GCAGATTACG 3850
CGCAGAAAAA AAGGATCTCA AGAAGATCCT TTGATCTTTT CTACGGGGTC 3900
TGACGCTCAG TGGAACGAAA ACTCACGTTA AGGGATTTTG GTCATGAGAT 3950
TATCAAAAAG GATCTTCACC TAGATCCTTT TAAATTAAAA ATGAAGTTTT 4000
AAATCAATCT AAAGTATATA TGAGTAAACT TGGTCTGACA GTTACCAATG 4050
CTTAATCAGT GAGGCACCTA TCTCAGCGAT CTGTCTATTT CGTTCATCCA 4100
TAGTTGCCTG ACTCCCCGTC GTGTAGATAA CTACGATACG GGAGGGCTTA 4150
CCATCTGGCC CCAGTGCTGC AATGATACCG CGAGACCCAC GCTCACCGGC 4200
TCCAGATTTA TCAGCAATAA ACCAGCCAGC CGGAAGGGCC GAGCGCAGAA 4250
GTGGTCCTGC AACTTTATCC GCCTCCATCC AGTCTATTAA TTGTTGCCGG 4300
GAAGCTAGAG TAAGTAGTTC GCCAGTTAAT AGTTTGCGCA ACGTTGTTGC 4350
CATTGCTGCA GGCATCGTGG TGTCACGCTC GTCGTTTGGT ATGGCTTCAT 4400
```

```
TCAGCTCCGG TTCCCAACGA TCAAGGCGAG TTACATGATC CCCCATGTTG    4450

TGCAAAAAAG CGGTTAGCTC CTTCGGTCCT CCGATCGTTG TCAGAAGTAA    4500

GTTGGCCGCA GTGTTATCAC TCATGGTTAT GGCAGCACTG CATAATTCTC    4550

TTACTGTCAT GCCATCCGTA AGATGCTTTT CTGTGACTGG TGAGTACTCA    4600

ACCAAGTCAT TCTGAGAATA GTGTATGCGG CGACCGAGTT GCTCTTGCCC    4650

GGCGTCAACA CGGGATAATA CCGCGCCACA TAGCAGAACT TTAAAAGTGC    4700

TCATCATTGG AAAACGTTCT TCGGGGCGAA AACTCTCAAG GATCTTACCG    4750

CTGTTGAGAT CCAGTTCGAT GTAACCCACT CGTGCACCCA ACTGATCTTC    4800

AGCATCTTTT ACTTTCACCA GCGTTTCTGG GTGAGCAAAA ACAGGAAGGC    4850

AAAATGCCGC AAAAAAGGGA ATAAGGGCGA CACGGAAATG TTGAATACTC    4900

ATACTCTTCC TTTTTCAATA TTATTGAAGC ATTTATCAGG GTTATTGTCT    4950

CATGAGCGGA TACATATTTG AATGTATTTA GAAAAATAAA CAAATAGGGG    5000

TTCCGCGCAC ATTTCCCCGA AAAGTGCCAC CTGACGTCTA AGAAACCATT    5050

ATTATCATGA CATTAACCTA TAAAAATAGG CGTATCACGA GGCCCTTTCG    5100

TCTTCAAGAA    5110
```

( 2 ) INFORMATION FOR SEQ ID NO:8:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCM-T270

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: Inactive T7 φ10 promoter mutant (-9C to A)
            located between nucleotides 198 and 220 and in front of
            a promoterless chloramphicol acetyl transferase (CAT)
            gene.
        ( B ) LOCATION: 198 to 220
        ( C ) IDENTIFICATION METHOD: The clone was constructed from
            pKK232-8 and the inserted "promoter"was sequenced.
        ( D ) OTHER INFORMATION: If the mutant T7 promoter between
            positions 198 and 220 is recognizable by T7 RNA
            polymerase or a mutant T7 RNA polymerase, CAT can be
            expressed from the plasmid.

( x ) PUBLICATION INFORMATION:
        ( A ) AUTHORS: Ikeda, R.A., Chang, L.L., and Warshamana, G.S.

(B) TITLE: Selection and Characterization of a Mutant T7
    RNA Polymerase that Recognizes an Expanded Range
    of T7-like Promoters
(C) JOURNAL: Biochemistry
(D) VOLUME: 32
(E) ISSUE: 35
(F) PAGES: 9115-9124
(G) DATE: Sept. 7, 1993
(H) DOCUMENT NUMBER:
(I) FILING DATE:
(J) PUBLICATION DATE:
(H) DOCUMENT NUMBER:
(I) FILING DATE:
(J) PUBLICATION DATE:
(K) RELEVANT RESIDUES IN SEQ ID NO: 1 to 5110

(ix) SEQUENCE DESCRIPTION: SEQ ID NO:8:

```
TTCCCAGGCA  TCAAATAAAA  CGAAAGGCTC  AGTCGAAAGA  CTGGGCCTTT   50

CGTTTTATCT  GTTGTTTGTC  GGTGAACGCT  CTCCTGAGTA  GGACAAATCC  100

GCCGGGAGCG  GATTTGAACG  TTGCGAAGCA  ACGGCCCGGA  GGGTGGCGGG  150

CAGGACGCCC  GCCATAAACT  GCCAGGGAAT  TCCCTAGTA  CTGAAATTAA   200
                                 T7 Promoter Positions    *
                                                         -15

TACGAATCAC  TATAGGGAGA  AAGCTTGAGT  AGGACAAATC  CGCCGAGCTT  250
    *    *      *    *
   -10   -5    +1   +5

CGACGAGATT  TTCAGGAGCT  AAGGAAGCTA  AAATGGAGAA  AAAAATCACT  300

GGATATACCA  CCGTTGATAT  ATCCCAATCG  CATCGTAAAG  AACATTTTGA  350

GGCATTTCAG  TCAGTTGCTC  AATGTACCTA  TAACCAGACC  GTTCAGCTGG  400

ATATTACGGC  CTTTTTAAAG  ACCGTAAAGA  AAAATAAGCA  CAAGTTTTAT  450

CCGGCCTTTA  TTCACATTCT  TGCCCGCCTG  ATGAATGCTC  ATCCGGAATT  500

CCGTATGGCA  ATGAAAGACG  GTGAGCTGGT  GATATGGGAT  AGTGTTCACC  550

CTTGTTACAC  CGTTTTCCAT  GAGCAAACTG  AAACGTTTTC  ATCGCTCTGG  600

AGTGAATACC  ACGACGATTT  CCGGCAGTTT  CTACACATAT  ATTCGCAAGA  650

TGTGGCGTGT  TACGGTGAAA  ACCTGGCCTA  TTTCCCTAAA  GGGTTTATTG  700

AGAATATGTT  TTTCGTCTCA  GCCAATCCCT  GGGTGAGTTT  CACCAGTTTT  750

GATTTAAACG  TGGCCAATAT  GGACAACTTC  TTCGCCCCCG  TTTTCACCAT  800

GGGCAAATAT  TATACGCAAG  GCGACAAGGT  GCTGATGCCG  CTGGCGATTC  850

AGGTTCATCA  TGCCGTCTGT  GATGGCTTCC  ATGTCGGCAG  AATGCTTAAT  900

GAATTACAAC  AGTACTGCGA  TGAGTGGCAG  GGCGGGGCGT  AATTTTTTA   950

AGGCAGTTAT  TGGTGCCCTT  AAACGCCTGG  TGCTACGCCT  GAATAAGTGA  1000

TAATAAGCGG  ATGAATGGCA  GAAATTCGTC  GAGGCGGCAC  CTCGCTAACG  1050

GATTCACCAC  TCCAAGAATT  GGAGCCAATC  AATTCTTGCG  GAGAACTGTG  1100

AATGCGCAAA  CCAACCCTTG  GCAGAACATA  TCCATCGCGT  CCGCCATCTC  1150

CAGCAGCCGC  ACGCGGCGCA  TCTCGGCTGT  TTTGGCGGAT  GAGAGAAGAT  1200

TTTCAGCCTG  ATACAGATTA  AATCAGAACG  CAGAAGCGGT  CTGATAAAAC  1250

AGAATTTGCC  TGGCGGCAGT  AGCGCGGTGG  TCCCACCTGA  CCCCATGCCG  1300

AACTCAGAAG  TGAAACGCCG  TAGCGCCGAT  GGTAGTGTGG  GGTCTCCCCA  1350

TGCGAGAGTA  GGGAACTGCC  AGGCATCAAA  TAAAACGAAA  GGCTCAGTCG  1400

AAAGACTGGG  CCTTTCGTTT  TATCTGTTGT  TTGTCGGTGA  ACGCTCTCCT  1450

GAGTAGGACA  AATCCGCCGG  GAGCGGATTT  GAACGTTGCG  AAGCAACGGC  1500
```

| | | | | |
|---|---|---|---|---|
| CCGGAGGGTG | GCGGGCAGGA | CGCCCGCCAT | AAACTGCCAG | GCATCAAATT 1550 |
| AAGCAGAAGG | CCATCCTGAC | GGATGGCCTT | TTTGCGTTTC | TACAAACTCT 1600 |
| TCCTGTCGTC | ATATCTACAA | GCCATCCCCC | CACAGATACG | GTAAACTAGC 1650 |
| CTCGTTTTTG | CATCAGGAAA | GCAGCTGTTT | TGGCGGATGA | GAGAAGATTT 1700 |
| TCAGCCTGAT | ACAGATTAAA | TCAGAACGCA | GAAGCGGTCT | GATAAAACAG 1750 |
| AATTTGCCTG | GCGGCAGTAG | CGCGGTGGTC | CCACCTGACC | CCATGCCGAA 1800 |
| CTCAGAAGTG | AAACGCCGTA | GCGCCGATGG | TAGTGTGGGG | TCTCCCCATG 1850 |
| CGAGAGTAGG | GAACTGCCAG | GCATCAAATA | AAACGAAAGG | CTCAGTCGAA 1900 |
| AGACTGGGCC | TTTCGTTTTA | TCTGTTGTTT | GTCGGTGAAC | GCTCTCCTGA 1950 |
| GTAGGACAAA | TCCGCCGGGA | GCGGATTTGA | ACGTTGCGAA | GCAACGGCCC 2000 |
| GGAGGGTGGC | GGGCAGGACG | CCCGCCATAA | ACTGCCAGGC | ATCAAATTAA 2050 |
| GCAGAAGGCC | ATCCTGACGG | ATGGCCTTTT | TGCGTTTCTA | CAAACTCTTC 2100 |
| CTGTCGTCAT | ATCTACAAGC | CATCCCCCCA | CAGATACGGT | AAACTAGCCT 2150 |
| CGTTTTTGCA | TCAGGAAAGC | AGTCGGGCAG | CGTTGGGTCC | TGGCCACGGG 2200 |
| TGCGCATGAT | CGTGCTCCTG | TCGTTGAGGA | CCCGGCTAGG | CTGGCGGGGT 2250 |
| TGCCTTACTG | GTTAGCAGAA | TGAATCACCG | ATACGCGAGC | GAACGTGAAG 2300 |
| CGACTGCTGC | TGCAAAACGT | CTGCGACCTG | AGCAACAACA | TGAATGGTCT 2350 |
| TCGGTTTCCG | TGTTTCGTAA | AGTCTGGAAA | CGCGGAAGTC | AGCGCCCTGC 2400 |
| ACCATTATGT | TCCGGATCTG | CATCGCAGGA | TGCTGCTGGC | TACCCTGTGG 2450 |
| AACACCTACA | TCTGTATTAA | CGAAGCGCTG | GCATTGACCC | TGAGTGATTT 2500 |
| TTCTCTGGTC | CCGCCGCATC | CATACCGCCA | GTTGTTTACC | CTCACAACGT 2550 |
| TCCAGTAACC | GGGCATGTTC | ATCATCAGTA | ACCCGTATCG | TGAGCATCCT 2600 |
| CTCTCGTTTC | ATCGGTATCA | TTACCCCCAT | GAACAGAAAT | TCCCCCTTAC 2650 |
| ACGGAGGCAT | CAAGTGACCA | AACAGGAAAA | AACCGCCCTT | AACATGGCCC 2700 |
| GCTTTATCAG | AAGCCAGACA | TTAACGCTTC | TGGAGAAACT | CAACGAGCTG 2750 |
| GACGCGGATG | AACAGGCAGA | CATCTGTGAA | TCGCTTCACG | ACCACGCTGA 2800 |
| TGAGCTTTAC | CGCAGCTGCC | TCGCGCGTTT | CGGTGATGAC | GGTGAAAACC 2850 |
| TCTGACACAT | GCAGCTCCCG | GAGACGGTCA | CAGCTTGTCT | GTAAGCGGAT 2900 |
| GCCGGGAGCA | GACAAGCCCG | TCAGGGCGCG | TCAGCGGGTG | TTGGCGGGTG 2950 |
| TCGGGGCGCA | GCCATGACCC | AGTCACGTAG | CGATAGCGGA | GTGTATACTG 3000 |
| GCTTAACTAT | GCGGCATCAG | AGCAGATTGT | ACTGAGAGTG | CACCATATGC 3050 |
| GGTGTGAAAT | ACCGCACAGA | TGCGTAAGGA | GAAAATACCG | CATCAGGCGC 3100 |
| TCTTCCGCTT | CCTCGCTCAC | TGACTCGCTG | CGCTCGGTCG | TTCGGCTGCG 3150 |
| GCGAGCGGTA | TCAGCTCACT | CAAAGGCGGT | AATACGGTTA | TCCACAGAAT 3200 |
| CAGGGGATAA | CGCAGGAAAG | AACATGTGAG | CAAAAGGCCA | GCAAAAGGCC 3250 |
| AGGAACCGTA | AAAAGGCCGC | GTTGCTGGCG | TTTTTCCATA | GGCTCCGCCC 3300 |
| CCCTGACGAG | CATCACAAAA | ATCGACGCTC | AAGTCAGAGG | TGGCGAAACC 3350 |
| CGACAGGACT | ATAAAGATAC | CAGGCGTTTC | CCCCTGGAAG | CTCCCTCGTG 3400 |
| CGCTCTCCTG | TTCCGACCCT | GCCGCTTACC | GGATACCTGT | CCGCCTTTCT 3450 |
| CCCTTCGGGA | AGCGTGGCGC | TTTCTCAATG | CTCACGCTGT | AGGTATCTCA 3500 |
| GTTCGGTGTA | GGTCGTTCGC | TCCAAGCTGG | GCTGTGTGCA | CGAACCCCCC 3550 |

```
GTTCAGCCCG ACCGCTGCGC CTTATCCGGT AACTATCGTC TTGAGTCCAA  3600
CCCGGTAAGA CACGACTTAT CGCCACTGGC AGCAGCCACT GGTAACAGGA  3650
TTAGCAGAGC GAGGTATGTA GGCGGTGCTA CAGAGTTCTT GAAGTGGTGG  3700
CCTAACTACG GCTACACTAG AAGGACAGTA TTTGGTATCT GCGCTCTGCT  3750
GAAGCCAGTT ACCTTCGGAA AAAGAGTTGG TAGCTCTTGA TCCGGCAAAC  3800
AAACCACCGC TGGTAGCGGT GGTTTTTTTG TTTGCAAGCA GCAGATTACG  3850
CGCAGAAAAA AAGGATCTCA AGAAGATCCT TTGATCTTTT CTACGGGTC   3900
TGACGCTCAG TGGAACGAAA ACTCACGTTA AGGGATTTTG GTCATGAGAT  3950
TATCAAAAAG GATCTTCACC TAGATCCTTT TAAATTAAAA ATGAAGTTTT  4000
AAATCAATCT AAAGTATATA TGAGTAAACT TGGTCTGACA GTTACCAATG  4050
CTTAATCAGT GAGGCACCTA TCTCAGCGAT CTGTCTATTT CGTTCATCCA  4100
TAGTTGCCTG ACTCCCGTC GTGTAGATAA CTACGATACG GGAGGGCTTA   4150
CCATCTGGCC CCAGTGCTGC AATGATACCG CGAGACCCAC GCTCACCGGC  4200
TCCAGATTTA TCAGCAATAA ACCAGCCAGC CGGAAGGGCC GAGCGCAGAA  4250
GTGGTCCTGC AACTTTATCC GCCTCCATCC AGTCTATTAA TTGTTGCCGG  4300
GAAGCTAGAG TAAGTAGTTC GCCAGTTAAT AGTTTGCGCA ACGTTGTTGC  4350
CATTGCTGCA GGCATCGTGG TGTCACGCTC GTCGTTTGGT ATGGCTTCAT  4400
TCAGCTCCGG TTCCCAACGA TCAAGGCGAG TTACATGATC CCCCATGTTG  4450
TGCAAAAAAG CGGTTAGCTC CTTCGGTCCT CCGATCGTTG TCAGAAGTAA  4500
GTTGGCCGCA GTGTTATCAC TCATGGTTAT GGCAGCACTG CATAATTCTC  4550
TTACTGTCAT GCCATCCGTA AGATGCTTTT CTGTGACTGG TGAGTACTCA  4600
ACCAAGTCAT TCTGAGAATA GTGTATGCGG CGACCGAGTT GCTCTTGCCC  4650
GGCGTCAACA CGGGATAATA CCGCGCCACA TAGCAGAACT TTAAAAGTGC  4700
TCATCATTGG AAAACGTTCT TCGGGGCGAA AACTCTCAAG GATCTTACCG  4750
CTGTTGAGAT CCAGTTCGAT GTAACCCACT CGTGCACCCA ACTGATCTTC  4800
AGCATCTTTT ACTTTCACCA GCGTTTCTGG GTGAGCAAAA ACAGGAAGGC  4850
AAAATGCCGC AAAAAAGGGA ATAAGGGCGA CACGGAAATG TTGAATACTC  4900
ATACTCTTCC TTTTTCAATA TTATTGAAGC ATTTATCAGG GTTATTGTCT  4950
CATGAGCGGA TACATATTTG AATGTATTTA GAAAAATAAA CAAATAGGGG  5000
TTCCGCGCAC ATTTCCCCGA AAAGTGCCAC CTGACGTCTA AGAAACCATT  5050
ATTATCATGA CATTAACCTA TAAAAATAGG CGTATCACGA GGCCCTTTCG  5100
TCTTCAAGAA  5110
```

( 2 ) INFORMATION FOR SEQ ID NO:9:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:

(A) ORGANISM: Not applicable
(B) STRAIN: Not applicable
(C) INDIVIDUAL ISOLATE: Not applicable
(D) DEVELOPMENTAL STAGE: Not applicable
(E) HAPLOTYPE: Not applicable
(F) TISSUE TYPE: Not applicable
(G) CELL TYPE: Not applicable
(H) ORGANELLE: Not applicable (vii) IMMEDIATE SOURCE:
(A) LIBRARY: Not applicable
(B) CLONE: pCM-P1087

(viii) POSITION IN GENOME:
(A) CHROMOSOME/SEGMENT: Not applicable
(B) MAP POSITION: Not applicable
(C) UNITS: Not applicable (ix) FEATURE:
(A) NAME/KEY: Inactive T7 φ10 promoter mutant (-9C to T) located between nucleotides 198 and 220 and in front of a promoterless chloramphicol acetyl transferase (CAT) gene.
(B) LOCATION: 198 to 220
(C) IDENTIFICATION METHOD: The clone was constructed from pKK232-8 and the inserted "promoter" was sequenced.
(D) OTHER INFORMATION: If the mutant T7 promoter between positions 198 and 220 is recognizable by T7 RNA polymerase or a mutant T7 RNA polymerase, CAT can be expressed from the plasmid.

(x) PUBLICATION INFORMATION:
(A) AUTHORS: Ikeda, R.A., Chang, L.L., and Warshamana, G.S.
(B) TITLE: Selection and Characterization of a Mutant T7 RNA Polymerase that Recognizes an Expanded Range of T7-like Promoters
(C) JOURNAL: Biochemistry
(D) VOLUME: 32
(E) ISSUE: 35
(F) PAGES: 9115-9124
(G) DATE: Sept. 7, 1993
(H) DOCUMENT NUMBER:
(I) FILING DATE:
(J) PUBLICATION DATE:
(H) DOCUMENT NUMBER:
(I) FILING DATE:
(J) PUBLICATION DATE:
(K) RELEVANT RESIDUES IN SEQ ID NO: 1 to 5110

(ix) SEQUENCE DESCRIPTION: SEQ ID NO:9:

```
TTCCCAGGCA TCAAATAAAA CGAAAGGCTC AGTCGAAAGA CTGGGCCTTT  50

CGTTTTATCT GTTGTTTGTC GGTGAACGCT CTCCTGAGTA GGACAAATCC  100

GCCGGGAGCG GATTTGAACG TTGCGAAGCA ACGGCCCGGA GGGTGGCGGG  150

CAGGACGCCC GCCATAAACT GCCAGGGAAT TCCCTAGTA  CTGAAATTAA  200
                                 T7 Promoter Positions
                                                   -15

TACGATTCAC TATAGGGAGA AAGCTTGAGT AGGACAAATC CGCCGAGCTT  250
 -10   -5    +1   +5

CGACGAGATT TTCAGGAGCT AAGGAAGCTA AAATGGAGAA AAAAATCACT  300

GGATATACCA CCGTTGATAT ATCCCAATCG CATCGTAAAG AACATTTTGA  350

GGCATTTCAG TCAGTTGCTC AATGTACCTA TAACCAGACC GTTCAGCTGG  400

ATATTACGGC CTTTTTAAAG ACCGTAAAGA AAAATAAGCA CAAGTTTTAT  450

CCGGCCTTTA TTCACATTCT TGCCCGCCTG ATGAATGCTC ATCCGGAATT  500

CCGTATGGCA ATGAAAGACG GTGAGCTGGT GATATGGGAT AGTGTTCACC  550

CTTGTTACAC CGTTTTCCAT GAGCAAACTG AAACGTTTTC ATCGCTCTGG  600

AGTGAATACC ACGACGATTT CCGGCAGTTT CTACACATAT ATTCGCAAGA  650

TGTGGCGTGT TACGGTGAAA ACCTGGCCTA TTTCCCTAAA GGGTTTATTG  700
```

```
AGAATATGTT TTTCGTCTCA GCCAATCCCT GGGTGAGTTT CACCAGTTTT  750
GATTTAAACG TGGCCAATAT GGACAACTTC TTCGCCCCCG TTTTCACCAT  800
GGGCAAATAT TATACGCAAG GCGACAAGGT GCTGATGCCG CTGGCGATTC  850
AGGTTCATCA TGCCGTCTGT GATGGCTTCC ATGTCGGCAG AATGCTTAAT  900
GAATTACAAC AGTACTGCGA TGAGTGGCAG GGCGGGGCGT AATTTTTTA  950
AGGCAGTTAT TGGTGCCCTT AAACGCCTGG TGCTACGCCT GAATAAGTGA  1000
TAATAAGCGG ATGAATGGCA GAAATTCGTC GAGGCGGCAC CTCGCTAACG  1050
GATTCACCAC TCCAAGAATT GGAGCCAATC AATTCTTGCG GAGAACTGTG  1100
AATGCGCAAA CCAACCCTTG GCAGAACATA TCCATCGCGT CCGCCATCTC  1150
CAGCAGCCGC ACGCGGCGCA TCTCGGCTGT TTTGGCGGAT GAGAGAAGAT  1200
TTTCAGCCTG ATACAGATTA AATCAGAACG CAGAAGCGGT CTGATAAAAC  1250
AGAATTTGCC TGGCGGCAGT AGCGCGGTGG TCCCACCTGA CCCCATGCCG  1300
AACTCAGAAG TGAAACGCCG TAGCGCCGAT GGTAGTGTGG GGTCTCCCCA  1350
TGCGAGAGTA GGGAACTGCC AGGCATCAAA TAAAACGAAA GGCTCAGTCG  1400
AAAGACTGGG CCTTTCGTTT TATCTGTTGT TTGTCGGTGA ACGCTCTCCT  1450
GAGTAGGACA AATCCGCCGG GAGCGGATTT GAACGTTGCG AAGCAACGGC  1500
CCGGAGGGTG GCGGGCAGGA CGCCCGCCAT AAACTGCCAG GCATCAAATT  1550
AAGCAGAAGG CCATCCTGAC GGATGGCCTT TTTGCGTTTC TACAAACTCT  1600
TCCTGTCGTC ATATCTACAA GCCATCCCCC CACAGATACG GTAAACTAGC  1650
CTCGTTTTTG CATCAGGAAA GCAGCTGTTT TGGCGGATGA GAGAAGATTT  1700
TCAGCCTGAT ACAGATTAAA TCAGAACGCA GAAGCGGTCT GATAAACAG  1750
AATTTGCCTG GCGGCAGTAG CGCGGTGGTC CCACCTGACC CCATGCCGAA  1800
CTCAGAAGTG AAACGCCGTA GCGCCGATGG TAGTGTGGGG TCTCCCCATG  1850
CGAGAGTAGG GAACTGCCAG GCATCAAATA AAACGAAAGG CTCAGTCGAA  1900
AGACTGGGCC TTTCGTTTTA TCTGTTGTTT GTCGGTGAAC GCTCTCCTGA  1950
GTAGGACAAA TCCGCCGGGA GCGGATTTGA ACGTTGCGAA GCAACGGCCC  2000
GGAGGGTGGC GGGCAGGACG CCCGCCATAA ACTGCCAGGC ATCAAATTAA  2050
GCAGAAGGCC ATCCTGACGG ATGGCCTTTT TGCGTTTCTA CAAACTCTTC  2100
CTGTCGTCAT ATCTACAAGC CATCCCCCCA CAGATACGGT AAACTAGCCT  2150
CGTTTTTGCA TCAGGAAAGC AGTCGGGCAG CGTTGGGTCC TGGCCACGGG  2200
TGCGCATGAT CGTGCTCCTG TCGTTGAGGA CCCGGCTAGG CTGGCGGGGT  2250
TGCCTTACTG GTTAGCAGAA TGAATCACCG ATACGCGAGC GAACGTGAAG  2300
CGACTGCTGC TGCAAAACGT CTGCGACCTG AGCAACAACA TGAATGGTCT  2350
TCGGTTTCCG TGTTTCGTAA AGTCTGGAAA CGCGGAAGTC AGCGCCCTGC  2400
ACCATTATGT TCCGGATCTG CATCGCAGGA TGCTGCTGGC TACCCTGTGG  2450
AACACCTACA TCTGTATTAA CGAAGCGCTG GCATTGACCC TGAGTGATTT  2500
TTCTCTGGTC CCGCCGCATC CATACCGCCA GTTGTTTACC CTCACAACGT  2550
TCCAGTAACC GGGCATGTTC ATCATCAGTA ACCCGTATCG TGAGCATCCT  2600
CTCTCGTTTC ATCGGTATCA TTACCCCCAT GAACAGAAAT TCCCCCTTAC  2650
ACGGAGGCAT CAAGTGACCA AACAGGAAAA AACCGCCCTT AACATGGCCC  2700
GCTTTATCAG AAGCCAGACA TTAACGCTTC TGGAGAAACT CAACGAGCTG  2750
```

-continued

```
GACGCGGATG AACAGGCAGA CATCTGTGAA TCGCTTCACG ACCACGCTGA 2800
TGAGCTTTAC CGCAGCTGCC TCGCGCGTTT CGGTGATGAC GGTGAAAACC 2850
TCTGACACAT GCAGCTCCCG GAGACGGTCA CAGCTTGTCT GTAAGCGGAT 2900
GCCGGGAGCA GACAAGCCCG TCAGGGCGCG TCAGCGGGTG TTGGCGGGTG 2950
TCGGGGCGCA GCCATGACCC AGTCACGTAG CGATAGCGGA GTGTATACTG 3000
GCTTAACTAT GCGGCATCAG AGCAGATTGT ACTGAGAGTG CACCATATGC 3050
GGTGTGAAAT ACCGCACAGA TGCGTAAGGA GAAAATACCG CATCAGGCGC 3100
TCTTCCGCTT CCTCGCTCAC TGACTCGCTG CGCTCGGTCG TTCGGCTGCG 3150
GCGAGCGGTA TCAGCTCACT CAAAGGCGGT AATACGGTTA TCCACAGAAT 3200
CAGGGGATAA CGCAGGAAAG AACATGTGAG CAAAAGGCCA GCAAAAGGCC 3250
AGGAACCGTA AAAAGGCCGC GTTGCTGGCG TTTTTCCATA GGCTCCGCCC 3300
CCCTGACGAG CATCACAAAA ATCGACGCTC AAGTCAGAGG TGGCGAAACC 3350
CGACAGGACT ATAAAGATAC CAGGCGTTTC CCCCTGGAAG CTCCCTCGTG 3400
CGCTCTCCTG TTCCGACCCT GCCGCTTACC GGATACCTGT CCGCCTTTCT 3450
CCCTTCGGGA AGCGTGGCGC TTTCTCAATG CTCACGCTGT AGGTATCTCA 3500
GTTCGGTGTA GGTCGTTCGC TCCAAGCTGG GCTGTGTGCA CGAACCCCCC 3550
GTTCAGCCCG ACCGCTGCGC CTTATCCGGT AACTATCGTC TTGAGTCCAA 3600
CCCGGTAAGA CACGACTTAT CGCCACTGGC AGCAGCCACT GGTAACAGGA 3650
TTAGCAGAGC GAGGTATGTA GGCGGTGCTA CAGAGTTCTT GAAGTGGTGG 3700
CCTAACTACG GCTACACTAG AAGGACAGTA TTTGGTATCT GCGCTCTGCT 3750
GAAGCCAGTT ACCTTCGGAA AAAGAGTTGG TAGCTCTTGA TCCGGCAAAC 3800
AAACCACCGC TGGTAGCGGT GGTTTTTTTG TTTGCAAGCA GCAGATTACG 3850
CGCAGAAAAA AAGGATCTCA AGAAGATCCT TTGATCTTTT CTACGGGGTC 3900
TGACGCTCAG TGGAACGAAA ACTCACGTTA AGGGATTTTG GTCATGAGAT 3950
TATCAAAAAG GATCTTCACC TAGATCCTTT TAAATTAAAA ATGAAGTTTT 4000
AAATCAATCT AAAGTATATA TGAGTAAACT TGGTCTGACA GTTACCAATG 4050
CTTAATCAGT GAGGCACCTA TCTCAGCGAT CTGTCTATTT CGTTCATCCA 4100
TAGTTGCCTG ACTCCCCGTC GTGTAGATAA CTACGATACG GGAGGGCTTA 4150
CCATCTGGCC CCAGTGCTGC AATGATACCG CGAGACCCAC GCTCACCGGC 4200
TCCAGATTTA TCAGCAATAA ACCAGCCAGC CGGAAGGGCC GAGCGCAGAA 4250
GTGGTCCTGC AACTTTATCC GCCTCCATCC AGTCTATTAA TTGTTGCCGG 4300
GAAGCTAGAG TAAGTAGTTC GCCAGTTAAT AGTTTGCGCA ACGTTGTTGC 4350
CATTGCTGCA GGCATCGTGG TGTCACGCTC GTCGTTTGGT ATGGCTTCAT 4400
TCAGCTCCGG TTCCCAACGA TCAAGGCGAG TTACATGATC CCCCATGTTG 4450
TGCAAAAAAG CGGTTAGCTC CTTCGGTCCT CCGATCGTTG TCAGAAGTAA 4500
GTTGGCCGCA GTGTTATCAC TCATGGTTAT GGCAGCACTG CATAATTCTC 4550
TTACTGTCAT GCCATCCGTA AGATGCTTTT CTGTGACTGG TGAGTACTCA 4600
ACCAAGTCAT TCTGAGAATA GTGTATGCGG CGACCGAGTT GCTCTTGCCC 4650
GGCGTCAACA CGGGATAATA CCGCGCCACA TAGCAGAACT TTAAAAGTGC 4700
TCATCATTGG AAAACGTTCT TCGGGGCGAA AACTCTCAAG GATCTTACCG 4750
CTGTTGAGAT CCAGTTCGAT GTAACCCACT CGTGCACCCA ACTGATCTTC 4800
```

```
AGCATCTTTT   ACTTTCACCA   GCGTTTCTGG   GTGAGCAAAA   ACAGGAAGGC   4850

AAAATGCCGC   AAAAAAGGGA   ATAAGGGCGA   CACGGAAATG   TTGAATACTC   4900

ATACTCTTCC   TTTTTCAATA   TTATTGAAGC   ATTTATCAGG   GTTATTGTCT   4950

CATGAGCGGA   TACATATTTG   AATGTATTTA   GAAAATAAA    CAAATAGGGG   5000

TTCCGCGCAC   ATTTCCCCGA   AAAGTGCCAC   CTGACGTCTA   AGAAACCATT   5050

ATTATCATGA   CATTAACCTA   TAAAAATAGG   CGTATCACGA   GGCCCTTTCG   5100

TCTTCAAGAA   5110
```

( 2 ) INFORMATION FOR SEQ ID NO:10:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCM-P1198

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: Intermediate T7 φ10 promoter mutant (-8T to G)
            located between nucleotides 198 and 220 and in front of
            a promoterless chloramphicol acetyl transferase (CAT)
            gene.
        ( B ) LOCATION: 198 to 220
        ( C ) IDENTIFICATION METHOD: The clone was constructed from
            pKK232-8 and the inserted "promoter" was sequenced.
        ( D ) OTHER INFORMATION: The mutant T7 promoter between
            positions 198 and 220 is weakly recognized by T7 RNA
            polymerase; consequently, CAT can be expressed from the
            plasmid.

( x ) PUBLICATION INFORMATION:
        ( A ) AUTHORS: Ikeda, R.A., Chang, L.L., and Warshamana, G.S.
        ( B ) TITLE: Selection and Characterization of a Mutant T7
            RNA Polymerase that Recognizes an Expanded Range
            of T7-like Promoters
        ( C ) JOURNAL: Biochemistry
        ( D ) VOLUME: 32
        ( E ) ISSUE: 35
        ( F ) PAGES: 9115-9124
        ( G ) DATE: Sept. 7, 1993
        ( H ) DOCUMENT NUMBER:
        ( I ) FILING DATE:
        ( J ) PUBLICATION DATE:
        ( H ) DOCUMENT NUMBER:
        ( I ) FILING DATE:
        ( J ) PUBLICATION DATE:
        ( K ) RELEVANT RESIDUES IN SEQ ID NO: 1 to 5110

( i x ) SEQUENCE DESCRIPTION: SEQ ID NO:10:

```
TTCCCAGGCA  TCAAATAAAA  CGAAAGGCTC  AGTCGAAAGA  CTGGGCCTTT   50
CGTTTTATCT  GTTGTTTGTC  GGTGAACGCT  CTCCTGAGTA  GGACAAATCC  100
GCCGGGAGCG  GATTTGAACG  TTGCGAAGCA  ACGGCCCGGA  GGGTGGCGGG  150
CAGGACGCCC  GCCATAAACT  GCCAGGGAAT  TCCCCTAGTA  CTGAAATTAA  200
                                    T7 Promoter Positions    *
                                                            -15

TACGACGCAC  TATAGGGAGA  AAGCTTGAGT  AGGACAAATC  CGCCGAGCTT  250
    *          *           *    *
  -10        -5          +1   +5

CGACGAGATT  TTCAGGAGCT  AAGGAAGCTA  AAATGGAGAA  AAAATCACT   300
GGATATACCA  CCGTTGATAT  ATCCCAATCG  CATCGTAAAG  AACATTTTGA  350
GGCATTTCAG  TCAGTTGCTC  AATGTACCTA  TAACCAGACC  GTTCAGCTGG  400
ATATTACGGC  CTTTTAAAG   ACCGTAAAGA  AAAATAAGCA  CAAGTTTTAT  450
CCGGCCTTTA  TTCACATTCT  TGCCCGCCTG  ATGAATGCTC  ATCCGGAATT  500
CCGTATGGCA  ATGAAAGACG  GTGAGCTGGT  GATATGGGAT  AGTGTTCACC  550
CTTGTTACAC  CGTTTCCAT   GAGCAAACTG  AAACGTTTTC  ATCGCTCTGG  600
AGTGAATACC  ACGACGATTT  CCGGCAGTTT  CTACACATAT  ATTCGCAAGA  650
TGTGGCGTGT  TACGGTGAAA  ACCTGGCCTA  TTTCCCTAAA  GGGTTTATTG  700
AGAATATGTT  TTTCGTCTCA  GCCAATCCCT  GGGTGAGTTT  CACCAGTTTT  750
GATTTAAACG  TGGCCAATAT  GGACAACTTC  TTCGCCCCCG  TTTTCACCAT  800
GGGCAAATAT  TATACGCAAG  GCGACAAGGT  GCTGATGCCG  CTGGCGATTC  850
AGGTTCATCA  TGCCGTCTGT  GATGGCTTCC  ATGTCGGCAG  AATGCTTAAT  900
GAATTACAAC  AGTACTGCGA  TGAGTGGCAG  GGCGGGGCGT  AATTTTTTA   950
AGGCAGTTAT  TGGTGCCCTT  AAACGCCTGG  TGCTACGCCT  GAATAAGTGA  1000
TAATAAGCGG  ATGAATGGCA  GAAATTCGTC  GAGGCGGCAC  CTCGCTAACG  1050
GATTCACCAC  TCCAAGAATT  GGAGCCAATC  AATTCTTGCG  GAGAACTGTG  1100
AATGCGCAAA  CCAACCCTTG  GCAGAACATA  TCCATCGCGT  CCGCCATCTC  1150
CAGCAGCCGC  ACGCGGCGCA  TCTCGGCTGT  TTTGGCGGAT  GAGAGAAGAT  1200
TTTCAGCCTG  ATACAGATTA  AATCAGAACG  CAGAAGCGGT  CTGATAAAAC  1250
AGAATTTGCC  TGGCGGCAGT  AGCGCGGTGG  TCCCACCTGA  CCCCATGCCG  1300
AACTCAGAAG  TGAAACGCCG  TAGCGCCGAT  GGTAGTGTGG  GGTCTCCCCA  1350
TGCGAGAGTA  GGGAACTGCC  AGGCATCAAA  TAAAACGAAA  GGCTCAGTCG  1400
AAAGACTGGG  CCTTTCGTTT  TATCTGTTGT  TTGTCGGTGA  ACGCTCTCCT  1450
GAGTAGGACA  AATCCGCCGG  GAGCGGATTT  GAACGTTGCG  AAGCAACGGC  1500
CCGGAGGGTG  GCGGGCAGGA  CGCCCGCCAT  AAACTGCCAG  CATCAAATT   1550
AAGCAGAAGG  CCATCCTGAC  GGATGGCCTT  TTTGCGTTTC  TACAAACTCT  1600
TCCTGTCGTC  ATATCTACAA  GCCATCCCCC  CACAGATACG  GTAAACTAGC  1650
CTCGTTTTTG  CATCAGGAAA  GCAGCTGTTT  TGGCGGATGA  GAAGATTT    1700
TCAGCCTGAT  ACAGATTAAA  TCAGAACGCA  GAAGCGGTCT  GATAAAACAG  1750
AATTTGCCTG  GCGGCAGTAG  CGCGGTGGTC  CCACCTGACC  CCATGCCGAA  1800
CTCAGAAGTG  AAACGCCGTA  GCGCCGATGG  TAGTGTGGGG  TCTCCCCATG  1850
CGAGAGTAGG  GAACTGCCAG  GCATCAAATA  AAACGAAAGG  CTCAGTCGAA  1900
```

| | | | | | |
|---|---|---|---|---|---|
| AGACTGGGCC | TTTCGTTTTA | TCTGTTGTTT | GTCGGTGAAC | GCTCTCCTGA | 1950 |
| GTAGGACAAA | TCCGCCGGGA | GCGGATTTGA | ACGTTGCGAA | GCAACGGCCC | 2000 |
| GGAGGGTGGC | GGGCAGGACG | CCCGCCATAA | ACTGCCAGGC | ATCAAATTAA | 2050 |
| GCAGAAGGCC | ATCCTGACGG | ATGGCCTTTT | TGCGTTTCTA | CAAACTCTTC | 2100 |
| CTGTCGTCAT | ATCTACAAGC | CATCCCCCCA | CAGATACGGT | AAACTAGCCT | 2150 |
| CGTTTTTGCA | TCAGGAAAGC | AGTCGGGCAG | CGTTGGGTCC | TGGCCACGGG | 2200 |
| TGCGCATGAT | CGTGCTCCTG | TCGTTGAGGA | CCCGGCTAGG | CTGGCGGGGT | 2250 |
| TGCCTTACTG | GTTAGCAGAA | TGAATCACCG | ATACGCGAGC | GAACGTGAAG | 2300 |
| CGACTGCTGC | TGCAAAACGT | CTGCGACCTG | AGCAACAACA | TGAATGGTCT | 2350 |
| TCGGTTTCCG | TGTTTCGTAA | AGTCTGGAAA | CGCGGAAGTC | AGCGCCCTGC | 2400 |
| ACCATTATGT | TCCGGATCTG | CATCGCAGGA | TGCTGCTGGC | TACCCTGTGG | 2450 |
| AACACCTACA | TCTGTATTAA | CGAAGCGCTG | GCATTGACCC | TGAGTGATTT | 2500 |
| TTCTCTGGTC | CCGCCGCATC | CATACCGCCA | GTTGTTTACC | CTCACAACGT | 2550 |
| TCCAGTAACC | GGGCATGTTC | ATCATCAGTA | ACCCGTATCG | TGAGCATCCT | 2600 |
| CTCTCGTTTC | ATCGGTATCA | TTACCCCCAT | GAACAGAAAT | TCCCCCTTAC | 2650 |
| ACGGAGGCAT | CAAGTGACCA | AACAGGAAAA | AACCGCCCTT | AACATGGCCC | 2700 |
| GCTTTATCAG | AAGCCAGACA | TTAACGCTTC | TGGAGAAACT | CAACGAGCTG | 2750 |
| GACGCGGATG | AACAGGCAGA | CATCTGTGAA | TCGCTTCACG | ACCACGCTGA | 2800 |
| TGAGCTTTAC | CGCAGCTGCC | TCGCGCGTTT | CGGTGATGAC | GGTGAAAACC | 2850 |
| TCTGACACAT | GCAGCTCCCG | GAGACGGTCA | CAGCTTGTCT | GTAAGCGGAT | 2900 |
| GCCGGGAGCA | GACAAGCCCG | TCAGGGCGCG | TCAGCGGGTG | TTGGCGGGTG | 2950 |
| TCGGGGCGCA | GCCATGACCC | AGTCACGTAG | CGATAGCGGA | GTGTATACTG | 3000 |
| GCTTAACTAT | GCGGCATCAG | AGCAGATTGT | ACTGAGAGTG | CACCATATGC | 3050 |
| GGTGTGAAAT | ACCGCACAGA | TGCGTAAGGA | GAAAATACCG | CATCAGGCGC | 3100 |
| TCTTCCGCTT | CCTCGCTCAC | TGACTCGCTG | CGCTCGGTCG | TTCGGCTGCG | 3150 |
| GCGAGCGGTA | TCAGCTCACT | CAAAGGCGGT | AATACGGTTA | TCCACAGAAT | 3200 |
| CAGGGGATAA | CGCAGGAAAG | AACATGTGAG | CAAAAGGCCA | GCAAAAGGCC | 3250 |
| AGGAACCGTA | AAAAGGCCGC | GTTGCTGGCG | TTTTTCCATA | GGCTCCGCCC | 3300 |
| CCCTGACGAG | CATCACAAAA | ATCGACGCTC | AAGTCAGAGG | TGGCGAAACC | 3350 |
| CGACAGGACT | ATAAAGATAC | CAGGCGTTTC | CCCCTGGAAG | CTCCCTCGTG | 3400 |
| CGCTCTCCTG | TTCCGACCCT | GCCGCTTACC | GGATACCTGT | CCGCCTTTCT | 3450 |
| CCCTTCGGGA | AGCGTGGCGC | TTTCTCAATG | CTCACGCTGT | AGGTATCTCA | 3500 |
| GTTCGGTGTA | GGTCGTTCGC | TCCAAGCTGG | GCTGTGTGCA | CGAACCCCCC | 3550 |
| GTTCAGCCCG | ACCGCTGCGC | CTTATCCGGT | AACTATCGTC | TTGAGTCCAA | 3600 |
| CCCGGTAAGA | CACGACTTAT | CGCCACTGGC | AGCAGCCACT | GGTAACAGGA | 3650 |
| TTAGCAGAGC | GAGGTATGTA | GGCGGTGCTA | CAGAGTTCTT | GAAGTGGTGG | 3700 |
| CCTAACTACG | GCTACACTAG | AAGGACAGTA | TTTGGTATCT | GCGCTCTGCT | 3750 |
| GAAGCCAGTT | ACCTTCGGAA | AAAGAGTTGG | TAGCTCTTGA | TCCGGCAAAC | 3800 |
| AAACCACCGC | TGGTAGCGGT | GGTTTTTTTG | TTTGCAAGCA | GCAGATTACG | 3850 |
| CGCAGAAAAA | AAGGATCTCA | AGAAGATCCT | TTGATCTTTT | CTACGGGGTC | 3900 |
| TGACGCTCAG | TGGAACGAAA | ACTCACGTTA | AGGGATTTTG | GTCATGAGAT | 3950 |

```
TATCAAAAAG  GATCTTCACC  TAGATCCTTT  TAAATTAAAA  ATGAAGTTTT  4000
AAATCAATCT  AAAGTATATA  TGAGTAAACT  TGGTCTGACA  GTTACCAATG  4050
CTTAATCAGT  GAGGCACCTA  TCTCAGCGAT  CTGTCTATTT  CGTTCATCCA  4100
TAGTTGCCTG  ACTCCCGTC   GTGTAGATAA  CTACGATACG  GGAGGGCTTA  4150
CCATCTGGCC  CCAGTGCTGC  AATGATACCG  CGAGACCCAC  GCTCACCGGC  4200
TCCAGATTTA  TCAGCAATAA  ACCAGCCAGC  CGGAAGGGCC  GAGCGCAGAA  4250
GTGGTCCTGC  AACTTTATCC  GCCTCCATCC  AGTCTATTAA  TTGTTGCCGG  4300
GAAGCTAGAG  TAAGTAGTTC  GCCAGTTAAT  AGTTTGCGCA  ACGTTGTTGC  4350
CATTGCTGCA  GGCATCGTGG  TGTCACGCTC  GTCGTTTGGT  ATGGCTTCAT  4400
TCAGCTCCGG  TTCCCAACGA  TCAAGGCGAG  TTACATGATC  CCCCATGTTG  4450
TGCAAAAAAG  CGGTTAGCTC  CTTCGGTCCT  CCGATCGTTG  TCAGAAGTAA  4500
GTTGGCCGCA  GTGTTATCAC  TCATGGTTAT  GGCAGCACTG  CATAATTCTC  4550
TTACTGTCAT  GCCATCCGTA  AGATGCTTTT  CTGTGACTGG  TGAGTACTCA  4600
ACCAAGTCAT  TCTGAGAATA  GTGTATGCGG  CGACCGAGTT  GCTCTTGCCC  4650
GGCGTCAACA  CGGGATAATA  CCGCGCCACA  TAGCAGAACT  TTAAAAGTGC  4700
TCATCATTGG  AAAACGTTCT  TCGGGGCGAA  AACTCTCAAG  GATCTTACCG  4750
CTGTTGAGAT  CCAGTTCGAT  GTAACCCACT  CGTGCACCCA  ACTGATCTTC  4800
AGCATCTTTT  ACTTTCACCA  GCGTTTCTGG  GTGAGCAAAA  ACAGGAAGGC  4850
AAAATGCCGC  AAAAAAGGGA  ATAAGGGCGA  CACGGAAATG  TTGAATACTC  4900
ATACTCTTCC  TTTTTCAATA  TTATTGAAGC  ATTTATCAGG  GTTATTGTCT  4950
CATGAGCGGA  TACATATTTG  AATGTATTTA  GAAAAATAAA  CAAATAGGGG  5000
TTCCGCGCAC  ATTTCCCCGA  AAAGTGCCAC  CTGACGTCTA  AGAAACCATT  5050
ATTATCATGA  CATTAACCTA  TAAAAATAGG  CGTATCACGA  GGCCCTTTCG  5100
TCTTCAAGAA  5110
```

( 2 ) INFORMATION FOR SEQ ID NO:11:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCM-T286

( v i i i ) POSITION IN GENOME:
        ( A ) CHROMOSOME/SEGMENT: Not applicable
        ( B ) MAP POSITION: Not applicable (C) UNITS: Not applicable (ix) FEATURE:
    (A) NAME/KEY: Inactive T7 φ10 promoter mutant (-8T to A)
    located between nucleotides 198 and 220 and in front of
    a promoterless chloramphicol acetyl transferase (CAT)
    gene.
    (B) LOCATION: 198 to 220
    (C) IDENTIFICATION METHOD: The clone was constructed from
    pKK232-8 and the inserted "promoter" was sequenced.
    (D) OTHER INFORMATION: If the mutant T7 promoter between
    positions 198 and 220 is recognizable by T7 RNA
    polymerase or a mutant T7 RNA polymerase, CAT can be
    expressed from the plasmid.

(x) PUBLICATION INFORMATION:
    (A) AUTHORS: Ikeda, R.A., Chang, L.L., and Warshamana, G.S.
    (B) TITLE: Selection and Characterization of a Mutant T7
    RNA Polymerase that Recognizes an Expanded Range
    of T7-like Promoters
    (C) JOURNAL: Biochemistry
    (D) VOLUME: 32
    (E) ISSUE: 35
    (F) PAGES: 9115-9124
    (G) DATE: Sept. 7, 1993
    (H) DOCUMENT NUMBER:
    (I) FILING DATE:
    (J) PUBLICATION DATE:
    (H) DOCUMENT NUMBER:
    (I) FILING DATE:
    (J) PUBLICATION DATE:
    (K) RELEVANT RESIDUES IN SEQ ID NO: 1 to 5110

(ix) SEQUENCE DESCRIPTION: SEQ ID NO:11:

```
TTCCCAGGCA TCAAATAAAA CGAAAGGCTC AGTCGAAAGA CTGGGCCTTT   50
CGTTTTATCT GTTGTTTGTC GGTGAACGCT CTCCTGAGTA GGACAAATCC  100
GCCGGGAGCG GATTTGAACG TTGCGAAGCA ACGGCCCGGA GGGTGGCGGG  150
CAGGACGCCC GCCATAAACT GCCAGGGAAT TCCCCTAGTA CTGAAATTAA  200
                                 T7 Promoter Positions    *
                                                         -15
TACGACACAC TATAGGGAGA AAGCTTGAGT AGGACAAATC CGCCGAGCTT  250
  *     *    *    *
 -10   -5   +1   +5
CGACGAGATT TTCAGGAGCT AAGGAAGCTA AATGGAGAA  AAAAATCACT  300
GGATATACCA CCGTTGATAT ATCCCAATCG CATCGTAAAG AACATTTTGA  350
GGCATTTCAG TCAGTTGCTC AATGTACCTA TAACCAGACC GTTCAGCTGG  400
ATATTACGGC CTTTTAAAG  ACCGTAAAGA AAAATAAGCA CAAGTTTTAT  450
CCGGCCTTTA TTCACATTCT TGCCCGCCTG ATGAATGCTC ATCCGGAATT  500
CCGTATGGCA ATGAAAGACG GTGAGCTGGT GATATGGGAT AGTGTTCACC  550
CTTGTTACAC CGTTTTCCAT GAGCAAACTG AAACGTTTTC ATCGCTCTGG  600
AGTGAATACC ACGACGATTT CCGGCAGTTT CTACACATAT ATTCGCAAGA  650
TGTGGCGTGT TACGGTGAAA ACCTGGCCTA TTTCCCTAAA GGGTTTATTG  700
AGAATATGTT TTTCGTCTCA GCCAATCCCT GGGTGAGTTT CACCAGTTTT  750
GATTTAAACG TGGCCAATAT GGACAACTTC TTCGCCCCCG TTTTCACCAT  800
GGGCAAATAT TATACGCAAG GCGACAAGGT GCTGATGCCG CTGGCGATTC  850
AGGTTCATCA TGCCGTCTGT GATGGCTTCC ATGTCGGCAG AATGCTTAAT  900
GAATTACAAC AGTACTGCGA TGAGTGGCAG GGCGGGGCGT AATTTTTTA   950
AGGCAGTTAT TGGTGCCCTT AAACGCCTGG TGCTACGCCT GAATAAGTGA 1000
TAATAAGCGG ATGAATGGCA GAAATTCGTC GAGGCGGCAC CTCGCTAACG 1050
GATTCACCAC TCCAAGAATT GGAGCCAATC AATTCTTGCG GAGAACTGTG 1100
```

| | | | | |
|---|---|---|---|---|
| AATGCGCAAA | CCAACCCTTG | GCAGAACATA | TCCATCGCGT | CCGCCATCTC 1150 |
| CAGCAGCCGC | ACGCGGCGCA | TCTCGGCTGT | TTTGGCGGAT | GAGAGAAGAT 1200 |
| TTTCAGCCTG | ATACAGATTA | AATCAGAACG | CAGAAGCGGT | CTGATAAAAC 1250 |
| AGAATTTGCC | TGGCGGCAGT | AGCGCGGTGG | TCCCACCTGA | CCCCATGCCG 1300 |
| AACTCAGAAG | TGAAACGCCG | TAGCGCCGAT | GGTAGTGTGG | GGTCTCCCCA 1350 |
| TGCGAGAGTA | GGGAACTGCC | AGGCATCAAA | TAAAACGAAA | GGCTCAGTCG 1400 |
| AAAGACTGGG | CCTTTCGTTT | TATCTGTTGT | TTGTCGGTGA | ACGCTCTCCT 1450 |
| GAGTAGGACA | AATCCGCCGG | GAGCGGATTT | GAACGTTGCG | AAGCAACGGC 1500 |
| CCGGAGGGTG | GCGGGCAGGA | CGCCCGCCAT | AAACTGCCAG | GCATCAAATT 1550 |
| AAGCAGAAGG | CCATCCTGAC | GGATGGCCTT | TTTGCGTTTC | TACAAACTCT 1600 |
| TCCTGTCGTC | ATATCTACAA | GCCATCCCCC | CACAGATACG | GTAAACTAGC 1650 |
| CTCGTTTTTG | CATCAGGAAA | GCAGCTGTTT | TGGCGGATGA | GAGAAGATTT 1700 |
| TCAGCCTGAT | ACAGATTAAA | TCAGAACGCA | GAAGCGGTCT | GATAAAACAG 1750 |
| AATTTGCCTG | GCGGCAGTAG | CGCGGTGGTC | CCACCTGACC | CCATGCCGAA 1800 |
| CTCAGAAGTG | AAACGCCGTA | GCGCCGATGG | TAGTGTGGGG | TCTCCCCATG 1850 |
| CGAGAGTAGG | GAACTGCCAG | GCATCAAATA | AAACGAAAGG | CTCAGTCGAA 1900 |
| AGACTGGGCC | TTTCGTTTTA | TCTGTTGTTT | GTCGGTGAAC | GCTCTCCTGA 1950 |
| GTAGGACAAA | TCCGCCGGGA | GCGGATTTGA | ACGTTGCGAA | GCAACGGCCC 2000 |
| GGAGGGTGGC | GGGCAGGACG | CCCGCCATAA | ACTGCCAGGC | ATCAAATTAA 2050 |
| GCAGAAGGCC | ATCCTGACGG | ATGGCCTTTT | TGCGTTTCTA | CAAACTCTTC 2100 |
| CTGTCGTCAT | ATCTACAAGC | CATCCCCCCA | CAGATACGGT | AAACTAGCCT 2150 |
| CGTTTTGCA | TCAGGAAAGC | AGTCGGGCAG | CGTTGGGTCC | TGGCCACGGG 2200 |
| TGCGCATGAT | CGTGCTCCTG | TCGTTGAGGA | CCCGGCTAGG | CTGGCGGGGT 2250 |
| TGCCTTACTG | GTTAGCAGAA | TGAATCACCG | ATACGCGAGC | GAACGTGAAG 2300 |
| CGACTGCTGC | TGCAAAACGT | CTGCGACCTG | AGCAACAACA | TGAATGGTCT 2350 |
| TCGGTTTCCG | TGTTTCGTAA | AGTCTGGAAA | CGCGGAAGTC | AGCGCCCTGC 2400 |
| ACCATTATGT | TCCGGATCTG | CATCGCAGGA | TGCTGCTGGC | TACCCTGTGG 2450 |
| AACACCTACA | TCTGTATTAA | CGAAGCGCTG | GCATTGACCC | TGAGTGATTT 2500 |
| TTCTCTGGTC | CCGCCGCATC | CATACCGCCA | GTTGTTTACC | CTCACAACGT 2550 |
| TCCAGTAACC | GGGCATGTTC | ATCATCAGTA | ACCCGTATCG | TGAGCATCCT 2600 |
| CTCTCGTTTC | ATCGGTATCA | TTACCCCCAT | GAACAGAAAT | TCCCCCTTAC 2650 |
| ACGGAGGCAT | CAAGTGACCA | AACAGGAAAA | AACCGCCCTT | AACATGGCCC 2700 |
| GCTTTATCAG | AAGCCAGACA | TTAACGCTTC | TGGAGAAACT | CAACGAGCTG 2750 |
| GACGCGGATG | AACAGGCAGA | CATCTGTGAA | TCGCTTCACG | ACCACGCTGA 2800 |
| TGAGCTTTAC | CGCAGCTGCC | TCGCGCGTTT | CGGTGATGAC | GGTGAAAACC 2850 |
| TCTGACACAT | GCAGCTCCCG | GAGACGGTCA | CAGCTTGTCT | GTAAGCGGAT 2900 |
| GCCGGGAGCA | GACAAGCCCG | TCAGGGCGCG | TCAGCGGGTG | TTGGCGGGTG 2950 |
| TCGGGGCGCA | GCCATGACCC | AGTCACGTAG | CGATAGCGGA | GTGTATACTG 3000 |
| GCTTAACTAT | GCGGCATCAG | AGCAGATTGT | ACTGAGAGTG | CACCATATGC 3050 |
| GGTGTGAAAT | ACCGCACAGA | TGCGTAAGGA | GAAAATACCG | CATCAGGCGC 3100 |
| TCTTCCGCTT | CCTCGCTCAC | TGACTCGCTG | CGCTCGGTCG | TTCGGCTGCG 3150 |

```
GCGAGCGGTA TCAGCTCACT CAAAGGCGGT AATACGGTTA TCCACAGAAT    3200
CAGGGGATAA CGCAGGAAAG AACATGTGAG CAAAAGGCCA GCAAAAGGCC    3250
AGGAACCGTA AAAAGGCCGC GTTGCTGGCG TTTTTCCATA GGCTCCGCCC    3300
CCCTGACGAG CATCACAAAA ATCGACGCTC AAGTCAGAGG TGGCGAAACC    3350
CGACAGGACT ATAAAGATAC CAGGCGTTTC CCCCTGGAAG CTCCCTCGTG    3400
CGCTCTCCTG TTCCGACCCT GCCGCTTACC GGATACCTGT CCGCCTTTCT    3450
CCCTTCGGGA AGCGTGGCGC TTTCTCAATG CTCACGCTGT AGGTATCTCA    3500
GTTCGGTGTA GGTCGTTCGC TCCAAGCTGG GCTGTGTGCA CGAACCCCCC    3550
GTTCAGCCCG ACCGCTGCGC CTTATCCGGT AACTATCGTC TTGAGTCCAA    3600
CCCGGTAAGA CACGACTTAT CGCCACTGGC AGCAGCCACT GGTAACAGGA    3650
TTAGCAGAGC GAGGTATGTA GGCGGTGCTA CAGAGTTCTT GAAGTGGTGG    3700
CCTAACTACG GCTACACTAG AAGGACAGTA TTTGGTATCT GCGCTCTGCT    3750
GAAGCCAGTT ACCTTCGGAA AAAGAGTTGG TAGCTCTTGA TCCGGCAAAC    3800
AAACCACCGC TGGTAGCGGT GGTTTTTTTG TTTGCAAGCA GCAGATTACG    3850
CGCAGAAAAA AAGGATCTCA AGAAGATCCT TTGATCTTTT CTACGGGGTC    3900
TGACGCTCAG TGGAACGAAA ACTCACGTTA AGGGATTTTG GTCATGAGAT    3950
TATCAAAAAG GATCTTCACC TAGATCCTTT TAAATTAAAA ATGAAGTTTT    4000
AAATCAATCT AAAGTATATA TGAGTAAACT TGGTCTGACA GTTACCAATG    4050
CTTAATCAGT GAGGCACCTA TCTCAGCGAT CTGTCTATTT CGTTCATCCA    4100
TAGTTGCCTG ACTCCCCGTC GTGTAGATAA CTACGATACG GGAGGGCTTA    4150
CCATCTGGCC CCAGTGCTGC AATGATACCG CGAGACCCAC GCTCACCGGC    4200
TCCAGATTTA TCAGCAATAA ACCAGCCAGC CGGAAGGGCC GAGCGCAGAA    4250
GTGGTCCTGC AACTTTATCC GCCTCCATCC AGTCTATTAA TTGTTGCCGG    4300
GAAGCTAGAG TAAGTAGTTC GCCAGTTAAT AGTTTGCGCA ACGTTGTTGC    4350
CATTGCTGCA GGCATCGTGG TGTCACGCTC GTCGTTTGGT ATGGCTTCAT    4400
TCAGCTCCGG TTCCCAACGA TCAAGGCGAG TTACATGATC CCCCATGTTG    4450
TGCAAAAAAG CGGTTAGCTC CTTCGGTCCT CCGATCGTTG TCAGAAGTAA    4500
GTTGGCCGCA GTGTTATCAC TCATGGTTAT GGCAGCACTG CATAATTCTC    4550
TTACTGTCAT GCCATCCGTA AGATGCTTTT CTGTGACTGG TGAGTACTCA    4600
ACCAAGTCAT TCTGAGAATA GTGTATGCGG CGACCGAGTT GCTCTTGCCC    4650
GGCGTCAACA CGGGATAATA CCGCGCCACA TAGCAGAACT TTAAAAGTGC    4700
TCATCATTGG AAAACGTTCT TCGGGGCGAA AACTCTCAAG GATCTTACCG    4750
CTGTTGAGAT CCAGTTCGAT GTAACCCACT CGTGCACCCA ACTGATCTTC    4800
AGCATCTTTT ACTTTCACCA GCGTTTCTGG GTGAGCAAAA ACAGGAAGGC    4850
AAAATGCCGC AAAAAAGGGA ATAAGGGCGA CACGGAAATG TTGAATACTC    4900
ATACTCTTCC TTTTTCAATA TTATTGAAGC ATTTATCAGG GTTATTGTCT    4950
CATGAGCGGA TACATATTTG AATGTATTTA GAAAAATAAA CAAATAGGGG    5000
TTCCGCGCAC ATTTCCCCGA AAAGTGCCAC CTGACGTCTA AGAAACCATT    5050
ATTATCATGA CATTAACCTA TAAAAATAGG CGTATCACGA GGCCCTTTCG    5100
TCTTCAAGAA                                               5110
```

( 2 ) INFORMATION FOR SEQ ID NO:12:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCM-B64

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: Intermediate T7 φ10 promoter mutant (-8T to C)
            located between nucleotides 198 and 220 and in front of
            a promoterless cloramphicol acetyl transferase (CAT)
            gene.
        ( B ) LOCATION: 198 to 220
        ( C ) IDENTIFICATION METHOD: The clone was constructed from
            pKK232-8 and the inserted "promoter"was sequenced.
        ( D ) OTHER INFORMATION: The mutant T7 promoter between
            positions 198 and 220 is weakly recognized by T7 RNA
            polymerase; consequently, CAT can be expressed from the
            plasmid.

( x ) PUBLICATION INFORMATION:
        ( A ) AUTHORS: Ikeda, R.A., Chang, L.L., and Warshamana, G.S.
        ( B ) TITLE: Selection and Characterization of a Mutant T7
            RNA Polymerase that Recognizes an Expanded Range
            of T7-like Promoters
        ( C ) JOURNAL: Biochemistry
        ( D ) VOLUME: 32
        ( E ) ISSUE: 35
        ( F ) PAGES: 9115-9124
        ( G ) DATE: Sept. 7, 1993
        ( H ) DOCUMENT NUMBER:
        ( I ) FILING DATE:
        ( J ) PUBLICATION DATE:
        ( H ) DOCUMENT NUMBER:
        ( I ) FILING DATE:
        ( J ) PUBLICATION DATE:
        ( K ) RELEVANT RESIDUES IN SEQ ID NO: 1 to 5110

( i x ) SEQUENCE DESCRIPTION: SEQ ID NO:12:

```
TTCCCAGGCA  TCAAATAAAA  CGAAAGGCTC  AGTCGAAAGA  CTGGGCCTTT   50

CGTTTTATCT  GTTGTTTGTC  GGTGAACGCT  CTCCTGAGTA  GGACAAATCC  100

GCCGGGAGCG  GATTTGAACG  TTGCGAAGCA  ACGGCCCGGA  GGGTGGCGGG  150

CAGGACGCCC  GCCATAAACT  GCCAGGGAAT  TCCCCTGAAT  TCGAATTAA   200
                              T7  Promoter  Positions      *
                                                         -15

TACGACCCAC  TATAGGGAGA  AAGCTTGAGT  AGGACAAATC  CGCCGAGCTT  250
    *           *           *           *
  -10         -5          +1         +5
```

```
CGACGAGATT  TTCAGGAGCT  AAGGAAGCTA  AAATGGAGAA  AAAAATCACT   300
GGATATACCA  CCGTTGATAT  ATCCCAATCG  CATCGTAAAG  AACATTTTGA   350
GGCATTTCAG  TCAGTTGCTC  AATGTACCTA  TAACCAGACC  GTTCAGCTGG   400
ATATTACGGC  CTTTTTAAAG  ACCGTAAAGA  AAAATAAGCA  CAAGTTTTAT   450
CCGGCCTTTA  TTCACATTCT  TGCCCGCCTG  ATGAATGCTC  ATCCGGAATT   500
CCGTATGGCA  ATGAAAGACG  GTGAGCTGGT  GATATGGGAT  AGTGTTCACC   550
CTTGTTACAC  CGTTTTCCAT  GAGCAAACTG  AAACGTTTTC  ATCGCTCTGG   600
AGTGAATACC  ACGACGATTT  CCGGCAGTTT  CTACACATAT  ATTCGCAAGA   650
TGTGGCGTGT  TACGGTGAAA  ACCTGGCCTA  TTTCCCTAAA  GGGTTTATTG   700
AGAATATGTT  TTTCGTCTCA  GCCAATCCCT  GGGTGAGTTT  CACCAGTTTT   750
GATTTAAACG  TGGCCAATAT  GGACAACTTC  TTCGCCCCCG  TTTTCACCAT   800
GGGCAAATAT  TATACGCAAG  GCGACAAGGT  GCTGATGCCG  CTGGCGATTC   850
AGGTTCATCA  TGCCGTCTGT  GATGGCTTCC  ATGTCGGCAG  AATGCTTAAT   900
GAATTACAAC  AGTACTGCGA  TGAGTGGCAG  GGCGGGGCGT  AATTTTTTTA   950
AGGCAGTTAT  TGGTGCCCTT  AAACGCCTGG  TGCTACGCCT  GAATAAGTGA  1000
TAATAAGCGG  ATGAATGGCA  GAAATTCGTC  GAGGCGGCAC  CTCGCTAACG  1050
GATTCACCAC  TCCAAGAATT  GGAGCCAATC  AATTCTTGCG  GAGAACTGTG  1100
AATGCGCAAA  CCAACCCTTG  GCAGAACATA  TCCATCGCGT  CCGCCATCTC  1150
CAGCAGCCGC  ACGCGGCGCA  TCTCGGCTGT  TTTGGCGGAT  GAGAGAAGAT  1200
TTTCAGCCTG  ATACAGATTA  AATCAGAACG  CAGAAGCGGT  CTGATAAAAC  1250
AGAATTTGCC  TGGCGGCAGT  AGCGCGGTGG  TCCCACCTGA  CCCCATGCCG  1300
AACTCAGAAG  TGAAACGCCG  TAGCGCCGAT  GGTAGTGTGG  GGTCTCCCCA  1350
TGCGAGAGTA  GGGAACTGCC  AGGCATCAAA  TAAAACGAAA  GGCTCAGTCG  1400
AAAGACTGGG  CCTTTCGTTT  TATCTGTTGT  TTGTCGGTGA  ACGCTCTCCT  1450
GAGTAGGACA  AATCCGCCGG  GAGCGGATTT  GAACGTTGCG  AAGCAACGGC  1500
CCGGAGGGTG  GCGGGCAGGA  CGCCCGCCAT  AAACTGCCAG  GCATCAAATT  1550
AAGCAGAAGG  CCATCCTGAC  GGATGGCCTT  TTTGCGTTTC  TACAAACTCT  1600
TCCTGTCGTC  ATATCTACAA  GCCATCCCCC  CACAGATACG  GTAAACTAGC  1650
CTCGTTTTTG  CATCAGGAAA  GCAGCTGTTT  TGGCGGATGA  GAAGATTT    1700
TCAGCCTGAT  ACAGATTAAA  TCAGAACGCA  GAAGCGGTCT  GATAAACAG   1750
AATTTGCCTG  GCGGCAGTAG  CGCGGTGGTC  CCACCTGACC  CCATGCCGAA  1800
CTCAGAAGTG  AAACGCCGTA  GCGCCGATGG  TAGTGTGGGG  TCTCCCCATG  1850
CGAGAGTAGG  GAACTGCCAG  GCATCAAATA  AAACGAAAGG  CTCAGTCGAA  1900
AGACTGGGCC  TTTCGTTTTA  TCTGTTGTTT  GTCGGTGAAC  GCTCTCCTGA  1950
GTAGGACAAA  TCCGCCGGGA  GCGGATTTGA  ACGTTGCGAA  GCAACGGCCC  2000
GGAGGGTGGC  GGGCAGGACG  CCCGCCATAA  ACTGCCAGGC  ATCAAATTAA  2050
GCAGAAGGCC  ATCCTGACGG  ATGGCCTTTT  TGCGTTTCTA  CAAACTCTTC  2100
CTGTCGTCAT  ATCTACAAGC  CATCCCCCCA  CAGATACGGT  AAACTAGCCT  2150
CGTTTTTGCA  TCAGGAAAGC  AGTCGGGCAG  CGTTGGGTCC  TGGCCACGGG  2200
TGCGCATGAT  CGTGCTCCTG  TCGTTGAGGA  CCCGGCTAGG  CTGGCGGGGT  2250
TGCCTTACTG  GTTAGCAGAA  TGAATCACCG  ATACGCGAGC  GAACGTGAAG  2300
```

```
CGACTGCTGC TGCAAAACGT CTGCGACCTG AGCAACAACA TGAATGGTCT  2350
TCGGTTTCCG TGTTTCGTAA AGTCTGGAAA CGCGGAAGTC AGCGCCCTGC  2400
ACCATTATGT TCCGGATCTG CATCGCAGGA TGCTGCTGGC TACCCTGTGG  2450
AACACCTACA TCTGTATTAA CGAAGCGCTG GCATTGACCC TGAGTGATTT  2500
TTCTCTGGTC CCGCCGCATC CATACCGCCA GTTGTTTACC CTCACAACGT  2550
TCCAGTAACC GGGCATGTTC ATCATCAGTA ACCCGTATCG TGAGCATCCT  2600
CTCTCGTTTC ATCGGTATCA TTACCCCCAT GAACAGAAAT TCCCCCTTAC  2650
ACGGAGGCAT CAAGTGACCA AACAGGAAAA AACCGCCCTT AACATGGCCC  2700
GCTTTATCAG AAGCCAGACA TTAACGCTTC TGGAGAAACT CAACGAGCTG  2750
GACGCGGATG AACAGGCAGA CATCTGTGAA TCGCTTCACG ACCACGCTGA  2800
TGAGCTTTAC CGCAGCTGCC TCGCGCGTTT CGGTGATGAC GGTGAAAACC  2850
TCTGACACAT GCAGCTCCCG GAGACGGTCA CAGCTTGTCT GTAAGCGGAT  2900
GCCGGGAGCA GACAAGCCCG TCAGGGCGCG TCAGCGGGTG TTGGCGGGTG  2950
TCGGGGCGCA GCCATGACCC AGTCACGTAG CGATAGCGGA GTGTATACTG  3000
GCTTAACTAT GCGGCATCAG AGCAGATTGT ACTGAGAGTG CACCATATGC  3050
GGTGTGAAAT ACCGCACAGA TGCGTAAGGA GAAAATACCG CATCAGGCGC  3100
TCTTCCGCTT CCTCGCTCAC TGACTCGCTG CGCTCGGTCG TTCGGCTGCG  3150
GCGAGCGGTA TCAGCTCACT CAAAGGCGGT AATACGGTTA TCCACAGAAT  3200
CAGGGGATAA CGCAGGAAAG AACATGTGAG CAAAAGGCCA GCAAAAGGCC  3250
AGGAACCGTA AAAAGGCCGC GTTGCTGGCG TTTTTCCATA GGCTCCGCCC  3300
CCCTGACGAG CATCACAAAA ATCGACGCTC AAGTCAGAGG TGGCGAAACC  3350
CGACAGGACT ATAAAGATAC CAGGCGTTTC CCCCTGGAAG CTCCCTCGTG  3400
CGCTCTCCTG TTCCGACCCT GCCGCTTACC GGATACCTGT CCGCCTTTCT  3450
CCCTTCGGGA AGCGTGGCGC TTTCTCAATG CTCACGCTGT AGGTATCTCA  3500
GTTCGGTGTA GGTCGTTCGC TCCAAGCTGG GCTGTGTGCA CGAACCCCCC  3550
GTTCAGCCCG ACCGCTGCGC CTTATCCGGT AACTATCGTC TTGAGTCCAA  3600
CCCGGTAAGA CACGACTTAT CGCCACTGGC AGCAGCCACT GGTAACAGGA  3650
TTAGCAGAGC GAGGTATGTA GGCGGTGCTA CAGAGTTCTT GAAGTGGTGG  3700
CCTAACTACG GCTACACTAG AAGGACAGTA TTTGGTATCT GCGCTCTGCT  3750
GAAGCCAGTT ACCTTCGGAA AAAGAGTTGG TAGCTCTTGA TCCGGCAAAC  3800
AAACCACCGC TGGTAGCGGT GGTTTTTTTG TTTGCAAGCA GCAGATTACG  3850
CGCAGAAAAA AAGGATCTCA AGAAGATCCT TTGATCTTTT CTACGGGGTC  3900
TGACGCTCAG TGGAACGAAA ACTCACGTTA AGGGATTTTG GTCATGAGAT  3950
TATCAAAAAG GATCTTCACC TAGATCCTTT TAAATTAAAA ATGAAGTTTT  4000
AAATCAATCT AAAGTATATA TGAGTAAACT TGGTCTGACA GTTACCAATG  4050
CTTAATCAGT GAGGCACCTA TCTCAGCGAT CTGTCTATTT CGTTCATCCA  4100
TAGTTGCCTG ACTCCCCGTC GTGTAGATAA CTACGATACG GGAGGGCTTA  4150
CCATCTGGCC CCAGTGCTGC AATGATACCG CGAGACCCAC GCTCACCGGC  4200
TCCAGATTTA TCAGCAATAA ACCAGCCAGC CGGAAGGGCC GAGCGCAGAA  4250
GTGGTCCTGC AACTTTATCC GCCTCCATCC AGTCTATTAA TTGTTGCCGG  4300
GAAGCTAGAG TAAGTAGTTC GCCAGTTAAT AGTTTGCGCA ACGTTGTTGC  4350
```

-continued

```
CATTGCTGCA GGCATCGTGG TGTCACGCTC GTCGTTTGGT ATGGCTTCAT 4400
TCAGCTCCGG TTCCCAACGA TCAAGGCGAG TTACATGATC CCCCATGTTG 4450
TGCAAAAAAG CGGTTAGCTC CTTCGGTCCT CCGATCGTTG TCAGAAGTAA 4500
GTTGGCCGCA GTGTTATCAC TCATGGTTAT GGCAGCACTG CATAATTCTC 4550
TTACTGTCAT GCCATCCGTA AGATGCTTTT CTGTGACTGG TGAGTACTCA 4600
ACCAAGTCAT TCTGAGAATA GTGTATGCGG CGACCGAGTT GCTCTTGCCC 4650
GGCGTCAACA CGGGATAATA CCGCGCCACA TAGCAGAACT TTAAAAGTGC 4700
TCATCATTGG AAAACGTTCT TCGGGGCGAA AACTCTCAAG GATCTTACCG 4750
CTGTTGAGAT CCAGTTCGAT GTAACCCACT CGTGCACCCA ACTGATCTTC 4800
AGCATCTTTT ACTTTCACCA GCGTTTCTGG GTGAGCAAAA ACAGGAAGGC 4850
AAAATGCCGC AAAAAAGGGA ATAAGGGCGA CACGGAAATG TTGAATACTC 4900
ATACTCTTCC TTTTTCAATA TTATTGAAGC ATTTATCAGG GTTATTGTCT 4950
CATGAGCGGA TACATATTTG AATGTATTTA GAAAAATAAA CAAATAGGGG 5000
TTCCGCGCAC ATTTCCCCGA AAAGTGCCAC CTGACGTCTA AGAAACCATT 5050
ATTATCATGA CATTAACCTA TAAAAATAGG CGTATCACGA GGCCCTTTCG 5100
TCTTCAAGAA 5110
```

( 2 ) INFORMATION FOR SEQ ID NO:13:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCM-P1208

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: Inactive T7 φ10 promoter mutant (-7C to G)
            located between nucleotides 198 and 220 and in front of
            a promoterless chloramphicol acetyl transferase (CAT)
            gene.
        ( B ) LOCATION: 198 to 220
        ( C ) IDENTIFICATION METHOD: The clone was constructed from
            pKK232-8 and the inserted "promoter" was sequenced.
        ( D ) OTHER INFORMATION: If the mutant T7 promoter between
            positions 198 and 220 is recognizable by T7 RNA
            polymerase or a mutant T7 RNA polymerase, CAT can be
            expressed from the plasmid.

( x ) PUBLICATION INFORMATION:

-continued (A) AUTHORS: Ikeda, R.A., Chang, L.L., and Warshamana, G.S.
(B) TITLE: Selection and Characterization of a Mutant T7
    RNA Polymerase that Recognizes an Expanded Range
    of T7-like Promoters
(C) JOURNAL: Biochemistry
(D) VOLUME: 32
(E) ISSUE: 35
(F) PAGES: 9115-9124
(G) DATE: Sept. 7, 1993
(H) DOCUMENT NUMBER:
(I) FILING DATE:
(J) PUBLICATION DATE:
(H) DOCUMENT NUMBER:
(I) FILING DATE:
(J) PUBLICATION DATE:
(K) RELEVANT RESIDUES IN SEQ ID NO: 1 to 5110

(ix) SEQUENCE DESCRIPTION: SEQ ID NO:13:

```
TTCCCAGGCA  TCAAATAAAA  CGAAAGGCTC  AGTCGAAAGA  CTGGGCCTTT   50

CGTTTTATCT  GTTGTTTGTC  GGTGAACGCT  CTCCTGAGTA  GGACAAATCC  100

GCCGGGAGCG  GATTTGAACG  TTGCGAAGCA  ACGGCCCGGA  GGGTGGCGGG  150

CAGGACGCCC  GCCATAAACT  GCCAGGGAAT  TCCCTAGTA   CTGAAATTAA  200
                                   T7 Promoter Positions   *
                                                          -15

TACGACTGAC  TATAGGGAGA  AAGCTTGAGT  AGGACAAATC  CGCCGAGCTT  250
    *    *     *    *
   -10   -5   +1   +5

CGACGAGATT  TTCAGGAGCT  AAGGAAGCTA  AAATGGAGAA  AAAAATCACT  300

GGATATACCA  CCGTTGATAT  ATCCCAATCG  CATCGTAAAG  AACATTTTGA  350

GGCATTTCAG  TCAGTTGCTC  AATGTACCTA  TAACCAGACC  GTTCAGCTGG  400

ATATTACGGC  CTTTTTAAAG  ACCGTAAAGA  AAAATAAGCA  CAAGTTTTAT  450

CCGGCCTTTA  TTCACATTCT  TGCCCGCCTG  ATGAATGCTC  ATCCGGAATT  500

CCGTATGGCA  ATGAAAGACG  GTGAGCTGGT  GATATGGGAT  AGTGTTCACC  550

CTTGTTACAC  CGTTTTCCAT  GAGCAAACTG  AAACGTTTTC  ATCGCTCTGG  600

AGTGAATACC  ACGACGATTT  CCGGCAGTTT  CTACACATAT  ATTCGCAAGA  650

TGTGGCGTGT  TACGGTGAAA  ACCTGGCCTA  TTTCCCTAAA  GGGTTTATTG  700

AGAATATGTT  TTTCGTCTCA  GCCAATCCCT  GGGTGAGTTT  CACCAGTTTT  750

GATTTAAACG  TGGCCAATAT  GGACAACTTC  TTCGCCCCCG  TTTTCACCAT  800

GGGCAAATAT  TATACGCAAG  GCGACAAGGT  GCTGATGCCG  CTGGCGATTC  850

AGGTTCATCA  TGCCGTCTGT  GATGGCTTCC  ATGTCGGCAG  AATGCTTAAT  900

GAATTACAAC  AGTACTGCGA  TGAGTGGCAG  GGCGGGGCGT  AATTTTTTA   950

AGGCAGTTAT  TGGTGCCCTT  AAACGCCTGG  TGCTACGCCT  GAATAAGTGA  1000

TAATAAGCGG  ATGAATGGCA  GAAATTCGTC  GAGGCGGCAC  CTCGCTAACG  1050

GATTCACCAC  TCCAAGAATT  GGAGCCAATC  AATTCTTGCG  GAGAACTGTG  1100

AATGCGCAAA  CCAACCCTTG  GCAGAACATA  TCCATCGCGT  CCGCCATCTC  1150

CAGCAGCCGC  ACGCGGCGCA  TCTCGGCTGT  TTTGGCGGAT  GAGAGAAGAT  1200

TTTCAGCCTG  ATACAGATTA  AATCAGAACG  CAGAAGCGGT  CTGATAAAAC  1250

AGAATTTGCC  TGGCGGCAGT  AGCGCGGTGG  TCCCACCTGA  CCCCATGCCG  1300

AACTCAGAAG  TGAAACGCCG  TAGCGCCGAT  GGTAGTGTGG  GGTCTCCCCA  1350

TGCGAGAGTA  GGGAACTGCC  AGGCATCAAA  TAAAACGAAA  GGCTCAGTCG  1400

AAAGACTGGG  CCTTTCGTTT  TATCTGTTGT  TTGTCGGTGA  ACGCTCTCCT  1450

GAGTAGGACA  AATCCGCCGG  GAGCGGATTT  GAACGTTGCG  AAGCAACGGC  1500
```

```
CCGGAGGGTG  GCGGGCAGGA  CGCCCGCCAT  AAACTGCCAG  GCATCAAATT  1550
AAGCAGAAGG  CCATCCTGAC  GGATGGCCTT  TTTGCGTTTC  TACAAACTCT  1600
TCCTGTCGTC  ATATCTACAA  GCCATCCCCC  CACAGATACG  GTAAACTAGC  1650
CTCGTTTTTG  CATCAGGAAA  GCAGCTGTTT  TGGCGGATGA  GAGAAGATTT  1700
TCAGCCTGAT  ACAGATTAAA  TCAGAACGCA  GAAGCGGTCT  GATAAACAG   1750
AATTTGCCTG  GCGGCAGTAG  CGCGGTGGTC  CCACCTGACC  CCATGCCGAA  1800
CTCAGAAGTG  AAACGCCGTA  GCGCCGATGG  TAGTGTGGGG  TCTCCCCATG  1850
CGAGAGTAGG  GAACTGCCAG  GCATCAAATA  AAACGAAAGG  CTCAGTCGAA  1900
AGACTGGGCC  TTTCGTTTTA  TCTGTTGTTT  GTCGGTGAAC  GCTCTCCTGA  1950
GTAGGACAAA  TCCGCCGGGA  GCGGATTTGA  ACGTTGCGAA  GCAACGGCCC  2000
GGAGGGTGGC  GGGCAGGACG  CCCGCCATAA  ACTGCCAGGC  ATCAAATTAA  2050
GCAGAAGGCC  ATCCTGACGG  ATGGCCTTTT  TGCGTTTCTA  CAAACTCTTC  2100
CTGTCGTCAT  ATCTACAAGC  CATCCCCCCA  CAGATACGGT  AAACTAGCCT  2150
CGTTTTTGCA  TCAGGAAAGC  AGTCGGGCAG  CGTTGGGTCC  TGGCCACGGG  2200
TGCGCATGAT  CGTGCTCCTG  TCGTTGAGGA  CCCGGCTAGG  CTGGCGGGGT  2250
TGCCTTACTG  GTTAGCAGAA  TGAATCACCG  ATACGCGAGC  GAACGTGAAG  2300
CGACTGCTGC  TGCAAAACGT  CTGCGACCTG  AGCAACAACA  TGAATGGTCT  2350
TCGGTTTCCG  TGTTTCGTAA  AGTCTGGAAA  CGCGGAAGTC  AGCGCCCTGC  2400
ACCATTATGT  TCCGGATCTG  CATCGCAGGA  TGCTGCTGGC  TACCCTGTGG  2450
AACACCTACA  TCTGTATTAA  CGAAGCGCTG  GCATTGACCC  TGAGTGATTT  2500
TTCTCTGGTC  CCGCCGCATC  CATACCGCCA  GTTGTTTACC  CTCACAACGT  2550
TCCAGTAACC  GGGCATGTTC  ATCATCAGTA  ACCCGTATCG  TGAGCATCCT  2600
CTCTCGTTTC  ATCGGTATCA  TTACCCCCAT  GAACAGAAAT  TCCCCCTTAC  2650
ACGGAGGCAT  CAAGTGACCA  AACAGGAAAA  AACCGCCCTT  AACATGGCCC  2700
GCTTTATCAG  AAGCCAGACA  TTAACGCTTC  TGGAGAAACT  CAACGAGCTG  2750
GACGCGGATG  AACAGGCAGA  CATCTGTGAA  TCGCTTCACG  ACCACGCTGA  2800
TGAGCTTTAC  CGCAGCTGCC  TCGCGCGTTT  CGGTGATGAC  GGTGAAAACC  2850
TCTGACACAT  GCAGCTCCCG  GAGACGGTCA  CAGCTTGTCT  GTAAGCGGAT  2900
GCCGGGAGCA  GACAAGCCCG  TCAGGGCGCG  TCAGCGGGTG  TTGGCGGGTG  2950
TCGGGGCGCA  GCCATGACCC  AGTCACGTAG  CGATAGCGGA  GTGTATACTG  3000
GCTTAACTAT  GCGGCATCAG  AGCAGATTGT  ACTGAGAGTG  CACCATATGC  3050
GGTGTGAAAT  ACCGCACAGA  TGCGTAAGGA  GAAAATACCG  CATCAGGCGC  3100
TCTTCCGCTT  CCTCGCTCAC  TGACTCGCTG  CGCTCGGTCG  TTCGGCTGCG  3150
GCGAGCGGTA  TCAGCTCACT  CAAAGGCGGT  AATACGGTTA  TCCACAGAAT  3200
CAGGGGATAA  CGCAGGAAAG  AACATGTGAG  CAAAAGGCCA  GCAAAAGGCC  3250
AGGAACCGTA  AAAAGGCCGC  GTTGCTGGCG  TTTTTCCATA  GGCTCCGCCC  3300
CCCTGACGAG  CATCACAAAA  ATCGACGCTC  AAGTCAGAGG  TGGCGAAACC  3350
CGACAGGACT  ATAAAGATAC  CAGGCGTTTC  CCCCTGGAAG  CTCCCTCGTG  3400
CGCTCTCCTG  TTCCGACCCT  GCCGCTTACC  GGATACCTGT  CCGCCTTTCT  3450
CCCTTCGGGA  AGCGTGGCGC  TTTCTCAATG  CTCACGCTGT  AGGTATCTCA  3500
GTTCGGTGTA  GGTCGTTCGC  TCCAAGCTGG  GCTGTGTGCA  CGAACCCCCC  3550
```

```
GTTCAGCCCG ACCGCTGCGC CTTATCCGGT AACTATCGTC TTGAGTCCAA    3600
CCCGGTAAGA CACGACTTAT CGCCACTGGC AGCAGCCACT GGTAACAGGA    3650
TTAGCAGAGC GAGGTATGTA GGCGGTGCTA CAGAGTTCTT GAAGTGGTGG    3700
CCTAACTACG GCTACACTAG AAGGACAGTA TTTGGTATCT GCGCTCTGCT    3750
GAAGCCAGTT ACCTTCGGAA AAAGAGTTGG TAGCTCTTGA TCCGGCAAAC    3800
AAACCACCGC TGGTAGCGGT GGTTTTTTTG TTTGCAAGCA GCAGATTACG    3850
CGCAGAAAAA AAGGATCTCA AGAAGATCCT TTGATCTTTT CTACGGGGTC    3900
TGACGCTCAG TGGAACGAAA ACTCACGTTA AGGGATTTTG GTCATGAGAT    3950
TATCAAAAAG GATCTTCACC TAGATCCTTT TAAATTAAAA ATGAAGTTTT    4000
AAATCAATCT AAAGTATATA TGAGTAAACT TGGTCTGACA GTTACCAATG    4050
CTTAATCAGT GAGGCACCTA TCTCAGCGAT CTGTCTATTT CGTTCATCCA    4100
TAGTTGCCTG ACTCCCGTC  GTGTAGATAA CTACGATACG GAGGGCTTA    4150
CCATCTGGCC CCAGTGCTGC AATGATACCG CGAGACCCAC GCTCACCGGC    4200
TCCAGATTTA TCAGCAATAA ACCAGCCAGC CGGAAGGGCC GAGCGCAGAA    4250
GTGGTCCTGC AACTTTATCC GCCTCCATCC AGTCTATTAA TTGTTGCCGG    4300
GAAGCTAGAG TAAGTAGTTC GCCAGTTAAT AGTTTGCGCA ACGTTGTTGC    4350
CATTGCTGCA GGCATCGTGG TGTCACGCTC GTCGTTTGGT ATGGCTTCAT    4400
TCAGCTCCGG TTCCCAACGA TCAAGGCGAG TTACATGATC CCCCATGTTG    4450
TGCAAAAAAG CGGTTAGCTC CTTCGGTCCT CCGATCGTTG TCAGAAGTAA    4500
GTTGGCCGCA GTGTTATCAC TCATGGTTAT GGCAGCACTG CATAATTCTC    4550
TTACTGTCAT GCCATCCGTA AGATGCTTTT CTGTGACTGG TGAGTACTCA    4600
ACCAAGTCAT TCTGAGAATA GTGTATGCGG CGACCGAGTT GCTCTTGCCC    4650
GGCGTCAACA CGGGATAATA CCGCGCCACA TAGCAGAACT TTAAAAGTGC    4700
TCATCATTGG AAAACGTTCT TCGGGGCGAA AACTCTCAAG GATCTTACCG    4750
CTGTTGAGAT CCAGTTCGAT GTAACCCACT CGTGCACCCA ACTGATCTTC    4800
AGCATCTTTT ACTTTCACCA GCGTTTCTGG GTGAGCAAAA ACAGGAAGGC    4850
AAAATGCCGC AAAAAAGGGA ATAAGGGCGA CACGGAAATG TTGAATACTC    4900
ATACTCTTCC TTTTTCAATA TTATTGAAGC ATTTATCAGG GTTATTGTCT    4950
CATGAGCGGA TACATATTTG AATGTATTTA GAAAAATAAA CAAATAGGGG    5000
TTCCGCGCAC ATTTCCCCGA AAAGTGCCAC CTGACGTCTA AGAAACCATT    5050
ATTATCATGA CATTAACCTA TAAAAATAGG CGTATCACGA GGCCCTTTCG    5100
TCTTCAAGAA    5110
```

(2) INFORMATION FOR SEQ ID NO:14:

(i) SEQUENCE CHARACTERISTICS:
        (A) LENGTH: 5110 base pairs
        (B) TYPE: nucleic acid
        (C) STRANDEDNESS: double
        (D) TOPOLOGY: circular (ii) MOLECULE TYPE: other nucleic acid (iii) HYPOTHETICAL: No (iv) ANTI-SENSE: No (v) FRAGMENT TYPE: Not applicable (vi) ORIGINAL SOURCE:
  (A) ORGANISM: Not applicable
  (B) STRAIN: Not applicable
  (C) INDIVIDUAL ISOLATE: Not applicable
  (D) DEVELOPMENTAL STAGE: Not applicable
  (E) HAPLOTYPE: Not applicable
  (F) TISSUE TYPE: Not applicable
  (G) CELL TYPE: Not applicable
  (H) ORGANELLE: Not applicable (vii) IMMEDIATE SOURCE:
  (A) LIBRARY: Not applicable
  (B) CLONE: pCM-P1031

(viii) POSITION IN GENOME:
  (A) CHROMOSOME/SEGMENT: Not applicable
  (B) MAP POSITION: Not applicable
  (C) UNITS: Not applicable (ix) FEATURE:
  (A) NAME/KEY: Inactive T7 φ10 promoter mutant (-7C to A)
      located between nucleotides 198 and 220 and in front of
      a pomoterless chloramphicol acetyl transferase (CAT)
      gene.
  (B) LOCATION: 198 to 220
  (C) IDENTIFICATION METHOD: The clone was constructed from
      pKK232-8 and the inserted "promoter" was sequenced.
  (D) OTHER INFORMATION: If the mutant T7 promoter between
      positions 198 and 220 is recognizable by T7 RNA
      polymerase or a mutant T7 RNA polymerase, CAT can be
      expressed from the plasmid.

(x) PUBLICATION INFORMATION:
  (A) AUTHORS: Ikeda, R.A., Chang, L.L., and Warshamana, G.S.
  (B) TITLE: Selection and Characterization of a Mutant T7
      RNA Polymerase that Recognizes an Expanded Range
      of T7-like Promoters
  (C) JOURNAL: Biochemistry
  (D) VOLUME: 32
  (E) ISSUE: 35
  (F) PAGES: 9115-9124
  (G) DATE: Sept. 7, 1993
  (H) DOCUMENT NUMBER:
  (I) FILING DATE:
  (J) PUBLICATION DATE:
  (H) DOCUMENT NUMBER:
  (I) FILING DATE:
  (J) PUBLICATION DATE:
  (K) RELEVANT RESIDUES IN SEQ ID NO: 1 to 5110

(ix) SEQUENCE DESCRIPTION: SEQ ID NO:14:

```
TTCCCAGGCA  TCAAATAAAA  CGAAAGGCTC  AGTCGAAAGA  CTGGGCCTTT   50
CGTTTTATCT  GTTGTTTGTC  GGTGAACGCT  CTCCTGAGTA  GGACAAATCC  100
GCCGGGAGCG  GATTTGAACG  TTGCGAAGCA  ACGGCCCGGA  GGGTGGCGGG  150
CAGGACGCCC  GCCATAAACT  GCCAGGGAAT  TCCCCTAGTA  CTGAAATTAA  200
                              T7 Promoter Positions
                                                        -15
TACGACTAAC  TATAGGGAGA  AAGCTTGAGT  AGGACAAATC  CGCCGAGCTT  250
   -10   -5    +1   +5
CGACGAGATT  TTCAGGAGCT  AAGGAAGCTA  AATGGAGAA   AAAAATCACT  300
GGATATACCA  CCGTTGATAT  ATCCCAATCG  CATCGTAAAG  AACATTTTGA  350
GGCATTTCAG  TCAGTTGCTC  AATGTACCTA  TAACCAGACC  GTTCAGCTGG  400
ATATTACGGC  CTTTTTAAAG  ACCGTAAAGA  AAAATAAGCA  CAAGTTTTAT  450
CCGGCCTTTA  TTCACATTCT  TGCCCGCCTG  ATGAATGCTC  ATCCGGAATT  500
CCGTATGGCA  ATGAAAGACG  GTGAGCTGGT  GATATGGGAT  AGTGTTCACC  550
CTTGTTACAC  CGTTTTCCAT  GAGCAAACTG  AAACGTTTTC  ATCGCTCTGG  600
AGTGAATACC  ACGACGATTT  CCGGCAGTTT  CTACACATAT  ATTCGCAAGA  650
```

| | | | | |
|---|---|---|---|---|
| TGTGGCGTGT | TACGGTGAAA | ACCTGGCCTA | TTTCCCTAAA | GGGTTTATTG 700 |
| AGAATATGTT | TTTCGTCTCA | GCCAATCCCT | GGGTGAGTTT | CACCAGTTTT 750 |
| GATTTAAACG | TGGCCAATAT | GGACAACTTC | TTCGCCCCCG | TTTTCACCAT 800 |
| GGGCAAATAT | TATACGCAAG | GCGACAAGGT | GCTGATGCCG | CTGGCGATTC 850 |
| AGGTTCATCA | TGCCGTCTGT | GATGGCTTCC | ATGTCGGCAG | AATGCTTAAT 900 |
| GAATTACAAC | AGTACTGCGA | TGAGTGGCAG | GCGGGGCGT | AATTTTTTA 950 |
| AGGCAGTTAT | TGGTGCCCTT | AAACGCCTGG | TGCTACGCCT | GAATAAGTGA 1000 |
| TAATAAGCGG | ATGAATGGCA | GAAATTCGTC | GAGGCGGCAC | CTCGCTAACG 1050 |
| GATTCACCAC | TCCAAGAATT | GGAGCCAATC | AATTCTTGCG | GAGAACTGTG 1100 |
| AATGCGCAAA | CCAACCCTTG | GCAGAACATA | TCCATCGCGT | CCGCCATCTC 1150 |
| CAGCAGCCGC | ACGCGGCGCA | TCTCGGCTGT | TTTGGCGGAT | GAGAGAAGAT 1200 |
| TTTCAGCCTG | ATACAGATTA | AATCAGAACG | CAGAAGCGGT | CTGATAAAAC 1250 |
| AGAATTTGCC | TGGCGGCAGT | AGCGCGGTGG | TCCCACCTGA | CCCCATGCCG 1300 |
| AACTCAGAAG | TGAAACGCCG | TAGCGCCGAT | GGTAGTGTGG | GGTCTCCCCA 1350 |
| TGCGAGAGTA | GGGAACTGCC | AGGCATCAAA | TAAAACGAAA | GGCTCAGTCG 1400 |
| AAAGACTGGG | CCTTTCGTTT | TATCTGTTGT | TTGTCGGTGA | ACGCTCTCCT 1450 |
| GAGTAGGACA | AATCCGCCGG | GAGCGGATTT | GAACGTTGCG | AAGCAACGGC 1500 |
| CCGGAGGGTG | GCGGGCAGGA | CGCCCGCCAT | AAACTGCCAG | GCATCAAATT 1550 |
| AAGCAGAAGG | CCATCCTGAC | GGATGGCCTT | TTTGCGTTTC | TACAAACTCT 1600 |
| TCCTGTCGTC | ATATCTACAA | GCCATCCCCC | CACAGATACG | GTAAACTAGC 1650 |
| CTCGTTTTTG | CATCAGGAAA | GCAGCTGTTT | TGGCGGATGA | GAGAAGATTT 1700 |
| TCAGCCTGAT | ACAGATTAAA | TCAGAACGCA | GAAGCGGTCT | GATAAAACAG 1750 |
| AATTTGCCTG | GCGGCAGTAG | CGCGGTGGTC | CCACCTGACC | CCATGCCGAA 1800 |
| CTCAGAAGTG | AAACGCCGTA | GCGCCGATGG | TAGTGTGGGG | TCTCCCCATG 1850 |
| CGAGAGTAGG | GAACTGCCAG | GCATCAAATA | AAACGAAAGG | CTCAGTCGAA 1900 |
| AGACTGGGCC | TTTCGTTTTA | TCTGTTGTTT | GTCGGTGAAC | GCTCTCCTGA 1950 |
| GTAGGACAAA | TCCGCCGGGA | GCGGATTTGA | ACGTTGCGAA | GCAACGGCCC 2000 |
| GGAGGGTGGC | GGGCAGGACG | CCCGCCATAA | ACTGCCAGGC | ATCAAATTAA 2050 |
| GCAGAAGGCC | ATCCTGACGG | ATGGCCTTTT | TGCGTTTCTA | CAAACTCTTC 2100 |
| CTGTCGTCAT | ATCTACAAGC | CATCCCCCCA | CAGATACGGT | AAACTAGCCT 2150 |
| CGTTTTGCA | TCAGGAAAGC | AGTCGGGCAG | CGTTGGGTCC | TGGCCACGGG 2200 |
| TGCGCATGAT | CGTGCTCCTG | TCGTTGAGGA | CCCGGCTAGG | CTGGCGGGGT 2250 |
| TGCCTTACTG | GTTAGCAGAA | TGAATCACCG | ATACGCGAGC | GAACGTGAAG 2300 |
| CGACTGCTGC | TGCAAAACGT | CTGCGACCTG | AGCAACAACA | TGAATGGTCT 2350 |
| TCGGTTTCCG | TGTTTCGTAA | AGTCTGGAAA | CGCGGAAGTC | AGCGCCCTGC 2400 |
| ACCATTATGT | TCCGGATCTG | CATCGCAGGA | TGCTGCTGGC | TACCCTGTGG 2450 |
| AACACCTACA | TCTGTATTAA | CGAAGCGCTG | GCATTGACCC | TGAGTGATTT 2500 |
| TTCTCTGGTC | CGCCGCATC | CATACCGCCA | GTTGTTTACC | CTCACAACGT 2550 |
| TCCAGTAACC | GGGCATGTTC | ATCATCAGTA | ACCCGTATCG | TGAGCATCCT 2600 |
| CTCTCGTTTC | ATCGGTATCA | TTACCCCCAT | GAACAGAAAT | TCCCCCTTAC 2650 |
| ACGGAGGCAT | CAAGTGACCA | AACAGGAAAA | AACCGCCCTT | AACATGGCCC 2700 |

```
GCTTTATCAG AAGCCAGACA TTAACGCTTC TGGAGAAACT CAACGAGCTG 2750
GACGCGGATG AACAGGCAGA CATCTGTGAA TCGCTTCACG ACCACGCTGA 2800
TGAGCTTTAC CGCAGCTGCC TCGCGCGTTT CGGTGATGAC GGTGAAAACC 2850
TCTGACACAT GCAGCTCCCG GAGACGGTCA CAGCTTGTCT GTAAGCGGAT 2900
GCCGGGAGCA GACAAGCCCG TCAGGGCGCG TCAGCGGGTG TTGGCGGGTG 2950
TCGGGGCGCA GCCATGACCC AGTCACGTAG CGATAGCGGA GTGTATACTG 3000
GCTTAACTAT GCGGCATCAG AGCAGATTGT ACTGAGAGTG CACCATATGC 3050
GGTGTGAAAT ACCGCACAGA TGCGTAAGGA GAAATACCG CATCAGGCGC 3100
TCTTCCGCTT CCTCGCTCAC TGACTCGCTG CGCTCGGTCG TTCGGCTGCG 3150
GCGAGCGGTA TCAGCTCACT CAAAGGCGGT AATACGGTTA TCCACAGAAT 3200
CAGGGGATAA CGCAGGAAAG AACATGTGAG CAAAAGGCCA GCAAAAGGCC 3250
AGGAACCGTA AAAAGGCCGC GTTGCTGGCG TTTTTCCATA GGCTCCGCCC 3300
CCCTGACGAG CATCACAAAA ATCGACGCTC AAGTCAGAGG TGGCGAAACC 3350
CGACAGGACT ATAAAGATAC CAGGCGTTTC CCCCTGGAAG CTCCCTCGTG 3400
CGCTCTCCTG TTCCGACCCT GCCGCTTACC GGATACCTGT CCGCCTTTCT 3450
CCCTTCGGGA AGCGTGGCGC TTTCTCAATG CTCACGCTGT AGGTATCTCA 3500
GTTCGGTGTA GGTCGTTCGC TCCAAGCTGG GCTGTGTGCA CGAACCCCCC 3550
GTTCAGCCCG ACCGCTGCGC CTTATCCGGT AACTATCGTC TTGAGTCCAA 3600
CCCGGTAAGA CACGACTTAT CGCCACTGGC AGCAGCCACT GGTAACAGGA 3650
TTAGCAGAGC GAGGTATGTA GGCGGTGCTA CAGAGTTCTT GAAGTGGTGG 3700
CCTAACTACG GCTACACTAG AAGGACAGTA TTTGGTATCT GCGCTCTGCT 3750
GAAGCCAGTT ACCTTCGGAA AAAGAGTTGG TAGCTCTTGA TCCGGCAAAC 3800
AAACCACCGC TGGTAGCGGT GGTTTTTTTG TTTGCAAGCA GCAGATTACG 3850
CGCAGAAAAA AAGGATCTCA AGAAGATCCT TTGATCTTTT CTACGGGGTC 3900
TGACGCTCAG TGGAACGAAA ACTCACGTTA AGGGATTTTG GTCATGAGAT 3950
TATCAAAAAG GATCTTCACC TAGATCCTTT TAAATTAAAA ATGAAGTTTT 4000
AAATCAATCT AAAGTATATA TGAGTAAACT TGGTCTGACA GTTACCAATG 4050
CTTAATCAGT GAGGCACCTA TCTCAGCGAT CTGTCTATTT CGTTCATCCA 4100
TAGTTGCCTG ACTCCCCGTC GTGTAGATAA CTACGATACG GGAGGGCTTA 4150
CCATCTGGCC CCAGTGCTGC AATGATACCG CGAGACCCAC GCTCACCGGC 4200
TCCAGATTTA TCAGCAATAA ACCAGCCAGC CGGAAGGGCC GAGCGCAGAA 4250
GTGGTCCTGC AACTTTATCC GCCTCCATCC AGTCTATTAA TTGTTGCCGG 4300
GAAGCTAGAG TAAGTAGTTC GCCAGTTAAT AGTTTGCGCA ACGTTGTTGC 4350
CATTGCTGCA GGCATCGTGG TGTCACGCTC GTCGTTTGGT ATGGCTTCAT 4400
TCAGCTCCGG TTCCCAACGA TCAAGGCGAG TTACATGATC CCCCATGTTG 4450
TGCAAAAAAG CGGTTAGCTC CTTCGGTCCT CCGATCGTTG TCAGAAGTAA 4500
GTTGGCCGCA GTGTTATCAC TCATGGTTAT GGCAGCACTG CATAATTCTC 4550
TTACTGTCAT GCCATCCGTA AGATGCTTTT CTGTGACTGG TGAGTACTCA 4600
ACCAAGTCAT TCTGAGAATA GTGTATGCGG CGACCGAGTT GCTCTTGCCC 4650
GGCGTCAACA CGGGATAATA CCGCGCCACA TAGCAGAACT TTAAAAGTGC 4700
TCATCATTGG AAAACGTTCT TCGGGGCGAA AACTCTCAAG GATCTTACCG 4750
```

```
CTGTTGAGAT  CCAGTTCGAT  GTAACCCACT  CGTGCACCCA  ACTGATCTTC  4800

AGCATCTTTT  ACTTTCACCA  GCGTTTCTGG  GTGAGCAAAA  ACAGGAAGGC  4850

AAAATGCCGC  AAAAAAGGGA  ATAAGGGCGA  CACGGAAATG  TTGAATACTC  4900

ATACTCTTCC  TTTTTCAATA  TTATTGAAGC  ATTTATCAGG  GTTATTGTCT  4950

CATGAGCGGA  TACATATTTG  AATGTATTTA  GAAAAATAAA  CAAATAGGGG  5000

TTCCGCGCAC  ATTTCCCCGA  AAAGTGCCAC  CTGACGTCTA  AGAAACCATT  5050

ATTATCATGA  CATTAACCTA  TAAAAATAGG  CGTATCACGA  GGCCCTTTCG  5100

TCTTCAAGAA  5110
```

( 2 ) INFORMATION FOR SEQ ID NO:15:

( i ) SEQUENCE CHARACTERISTICS:
        ( A ) LENGTH: 5110 base pairs
        ( B ) TYPE: nucleic acid
        ( C ) STRANDEDNESS: double
        ( D ) TOPOLOGY: circular ( i i ) MOLECULE TYPE: other nucleic acid ( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Not applicable
        ( B ) STRAIN: Not applicable
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Not applicable
        ( H ) ORGANELLE: Not applicable ( v i i ) IMMEDIATE SOURCE:
        ( A ) LIBRARY: Not applicable
        ( B ) CLONE: pCM-T221

( v i i i ) POSITION IN GENOME:
        ( A ) CHROMOSOME/SEGMENT: Not applicable
        ( B ) MAP POSITION: Not applicable
        ( C ) UNITS: Not applicable ( i x ) FEATURE:
        ( A ) NAME/KEY: Intermediate T7 φ10 promoter mutant (-6A to G)
            located between nucleotides 198 and 220 and in front of
            a promoterless chloramphicol acetyl transferase (CAT)
            gene.
        ( B ) LOCATION: 198 to 220
        ( C ) IDENTIFICATION METHOD: The clone was constructed from
            pKK232-8 and the inserted "promoter"was sequenced.
        ( D ) OTHER INFORMATION: The mutant T7 promoter between
            positions 198 and 220 is weakly recognized by T7 RNA
            polymerase; consequently, CAT can be expressed from the
            plasmid.

( x ) PUBLICATION INFORMATION:
        ( A ) AUTHORS: Ikeda, R.A., Chang, L.L., and Warshamana, G.S.
        ( B ) TITLE: Selection and Characterization of a Mutant T7
            RNA Polymerase that Recognizes an Expanded Range
            of T7-like Promoters
        ( C ) JOURNAL: Biochemistry
        ( D ) VOLUME: 32
        ( E ) ISSUE: 35
        ( F ) PAGES: 9115-9124
        ( G ) DATE: Sept. 7, 1993
        ( H ) DOCUMENT NUMBER:
        ( I ) FILING DATE:
        ( J ) PUBLICATION DATE:
        ( H ) DOCUMENT NUMBER:
        ( I ) FILING DATE:
        ( J ) PUBLICATION DATE:
        ( K ) RELEVANT RESIDUES IN SEQ ID NO: 1 to 5110

( i x ) SEQUENCE DESCRIPTION: SEQ ID NO:15:

```
TTCCCAGGCA TCAAATAAAA CGAAAGGCTC AGTCGAAAGA CTGGGCCTTT    50
CGTTTTATCT GTTGTTTGTC GGTGAACGCT CTCCTGAGTA GGACAAATCC   100
GCCGGGAGCG GATTTGAACG TTGCGAAGCA ACGGCCCGGA GGGTGGCGGG   150
CAGGACGCCC GCCATAAACT GCCAGGGAAT TCCCTAGTA CTGAAATTAA    200
```
T7 Promoter Positions
−15

```
TACGACTCGC TATAGGGAGA AAGCTTGAGT AGGACAAATC CGCCGAGCTT   250
```
−10  −5  +1  +5

```
CGACGAGATT TTCAGGAGCT AAGGAAGCTA AATGGAGAA AAAAATCACT    300
GGATATACCA CCGTTGATAT ATCCCAATCG CATCGTAAAG AACATTTTGA   350
GGCATTTCAG TCAGTTGCTC AATGTACCTA TAACCAGACC GTTCAGCTGG   400
ATATTACGGC CTTTTAAAG ACCGTAAAGA AAAATAAGCA CAAGTTTTAT    450
CCGGCCTTTA TTCACATTCT TGCCCGCCTG ATGAATGCTC ATCCGGAATT   500
CCGTATGGCA ATGAAAGACG GTGAGCTGGT GATATGGGAT AGTGTTCACC   550
CTTGTTACAC CGTTTTCCAT GAGCAAACTG AAACGTTTTC ATCGCTCTGG   600
AGTGAATACC ACGACGATTT CCGGCAGTTT CTACACATAT ATTCGCAAGA   650
TGTGGCGTGT TACGGTGAAA ACCTGGCCTA TTTCCCTAAA GGGTTTATTG   700
AGAATATGTT TTTCGTCTCA GCCAATCCCT GGGTGAGTTT CACCAGTTTT   750
GATTTAAACG TGGCCAATAT GGACAACTTC TTCGCCCCCG TTTTCACCAT   800
GGGCAAATAT TATACGCAAG GCGACAAGGT GCTGATGCCG CTGGCGATTC   850
AGGTTCATCA TGCCGTCTGT GATGGCTTCC ATGTCGGCAG AATGCTTAAT   900
GAATTACAAC AGTACTGCGA TGAGTGGCAG GGCGGGGCGT AATTTTTTA    950
AGGCAGTTAT TGGTGCCCTT AAACGCCTGG TGCTACGCCT GAATAAGTGA  1000
TAATAAGCGG ATGAATGGCA GAAATTCGTC GAGGCGGCAC CTCGCTAACG  1050
GATTCACCAC TCCAAGAATT GGAGCCAATC AATTCTTGCG GAGAACTGTG  1100
AATGCGCAAA CCAACCCTTG GCAGAACATA TCCATCGCGT CCGCCATCTC  1150
CAGCAGCCGC ACGCGGCGCA TCTCGGCTGT TTTGGCGGAT GAGAGAAGAT  1200
TTTCAGCCTG ATACAGATTA AATCAGAACG CAGAAGCGGT CTGATAAAAC  1250
AGAATTTGCC TGGCGGCAGT AGCGCGGTGG TCCCACCTGA CCCCATGCCG  1300
AACTCAGAAG TGAAACGCCG TAGCGCCGAT GGTAGTGTGG GGTCTCCCCA  1350
TGCGAGAGTA GGGAACTGCC AGGCATCAAA TAAAACGAAA GGCTCAGTCG  1400
AAAGACTGGG CCTTTCGTTT TATCTGTTGT TTGTCGGTGA ACGCTCTCCT  1450
GAGTAGGACA AATCCGCCGG GAGCGGATTT GAACGTTGCG AAGCAACGGC  1500
CCGGAGGGTG GCGGGCAGGA CGCCCGCCAT AAACTGCCAG CATCAAATT   1550
AAGCAGAAGG CCATCCTGAC GGATGGCCTT TTTGCGTTTC TACAAACTCT  1600
TCCTGTCGTC ATATCTACAA GCCATCCCCC CACAGATACG GTAAACTAGC  1650
CTCGTTTTTG CATCAGGAAA GCAGCTGTTT TGGCGGATGA GAAGATTT    1700
TCAGCCTGAT ACAGATTAAA TCAGAACGCA GAAGCGGTCT GATAAACAG   1750
AATTTGCCTG GCGGCAGTAG CGCGGTGGTC CCACCTGACC CCATGCCGAA  1800
CTCAGAAGTG AAACGCCGTA GCGCCGATGG TAGTGTGGGG TCTCCCCATG  1850
CGAGAGTAGG GAACTGCCAG GCATCAAATA AAACGAAAGG CTCAGTCGAA  1900
```

```
AGACTGGGCC TTTCGTTTTA TCTGTTGTTT GTCGGTGAAC GCTCTCCTGA 1950
GTAGGACAAA TCCGCCGGGA GCGGATTTGA ACGTTGCGAA GCAACGGCCC 2000
GGAGGGTGGC GGGCAGGACG CCCGCCATAA ACTGCCAGGC ATCAAATTAA 2050
GCAGAAGGCC ATCCTGACGG ATGGCCTTTT TGCGTTTCTA CAAACTCTTC 2100
CTGTCGTCAT ATCTACAAGC CATCCCCCCA CAGATACGGT AAACTAGCCT 2150
CGTTTTTGCA TCAGGAAAGC AGTCGGGCAG CGTTGGGTCC TGGCCACGGG 2200
TGCGCATGAT CGTGCTCCTG TCGTTGAGGA CCCGGCTAGG CTGGCGGGGT 2250
TGCCTTACTG GTTAGCAGAA TGAATCACCG ATACGCGAGC GAACGTGAAG 2300
CGACTGCTGC TGCAAAACGT CTGCGACCTG AGCAACAACA TGAATGGTCT 2350
TCGGTTTCCG TGTTTCGTAA AGTCTGGAAA CGCGGAAGTC AGCGCCCTGC 2400
ACCATTATGT TCCGGATCTG CATCGCAGGA TGCTGCTGGC TACCCTGTGG 2450
AACACCTACA TCTGTATTAA CGAAGCGCTG GCATTGACCC TGAGTGATTT 2500
TTCTCTGGTC CCGCCGCATC CATACCGCCA GTTGTTTACC CTCACAACGT 2550
TCCAGTAACC GGGCATGTTC ATCATCAGTA ACCCGTATCG TGAGCATCCT 2600
CTCTCGTTTC ATCGGTATCA TTACCCCCAT GAACAGAAAT TCCCCCTTAC 2650
ACGGAGGCAT CAAGTGACCA AACAGGAAAA AACCGCCCTT AACATGGCCC 2700
GCTTTATCAG AAGCCAGACA TTAACGCTTC TGGAGAAACT CAACGAGCTG 2750
GACGCGGATG AACAGGCAGA CATCTGTGAA TCGCTTCACG ACCACGCTGA 2800
TGAGCTTTAC CGCAGCTGCC TCGCGCGTTT CGGTGATGAC GGTGAAAACC 2850
TCTGACACAT GCAGCTCCCG GAGACGGTCA CAGCTTGTCT GTAAGCGGAT 2900
GCCGGGAGCA GACAAGCCCG TCAGGGCGCG TCAGCGGGTG TTGGCGGGTG 2950
TCGGGGCGCA GCCATGACCC AGTCACGTAG CGATAGCGGA GTGTATACTG 3000
GCTTAACTAT GCGGCATCAG AGCAGATTGT ACTGAGAGTG CACCATATGC 3050
GGTGTGAAAT ACCGCACAGA TGCGTAAGGA GAAAATACCG CATCAGGCGC 3100
TCTTCCGCTT CCTCGCTCAC TGACTCGCTG CGCTCGGTCG TTCGGCTGCG 3150
GCGAGCGGTA TCAGCTCACT CAAAGGCGGT AATACGGTTA TCCACAGAAT 3200
CAGGGGATAA CGCAGGAAAG AACATGTGAG CAAAAGGCCA GCAAAAGGCC 3250
AGGAACCGTA AAAAGGCCGC GTTGCTGGCG TTTTTCCATA GGCTCCGCCC 3300
CCCTGACGAG CATCACAAAA ATCGACGCTC AAGTCAGAGG TGGCGAAACC 3350
CGACAGGACT ATAAAGATAC CAGGCGTTTC CCCCTGGAAG CTCCCTCGTG 3400
CGCTCTCCTG TTCCGACCCT GCCGCTTACC GGATACCTGT CCGCCTTTCT 3450
CCCTTCGGGA AGCGTGGCGC TTTCTCAATG CTCACGCTGT AGGTATCTCA 3500
GTTCGGTGTA GGTCGTTCGC TCCAAGCTGG GCTGTGTGCA CGAACCCCCC 3550
GTTCAGCCCG ACCGCTGCGC CTTATCCGGT AACTATCGTC TTGAGTCCAA 3600
CCCGGTAAGA CACGACTTAT CGCCACTGGC AGCAGCCACT GGTAACAGGA 3650
TTAGCAGAGC GAGGTATGTA GGCGGTGCTA CAGAGTTCTT GAAGTGGTGG 3700
CCTAACTACG GCTACACTAG AAGGACAGTA TTTGGTATCT GCGCTCTGCT 3750
GAAGCCAGTT ACCTTCGGAA AAAGAGTTGG TAGCTCTTGA TCCGGCAAAC 3800
AAACCACCGC TGGTAGCGGT GGTTTTTTTG TTTGCAAGCA GCAGATTACG 3850
CGCAGAAAAA AAGGATCTCA AGAAGATCCT TTGATCTTTT CTACGGGGTC 3900
TGACGCTCAG TGGAACGAAA ACTCACGTTA AGGGATTTTG GTCATGAGAT 3950
```

| | | | | |
|---|---|---|---|---|
| TATCAAAAAG | GATCTTCACC | TAGATCCTTT | TAAATTAAAA | ATGAAGTTTT 4000 |
| AAATCAATCT | AAAGTATATA | TGAGTAAACT | TGGTCTGACA | GTTACCAATG 4050 |
| CTTAATCAGT | GAGGCACCTA | TCTCAGCGAT | CTGTCTATTT | CGTTCATCCA 4100 |
| TAGTTGCCTG | ACTCCCCGTC | GTGTAGATAA | CTACGATACG | GAGGGCTTA 4150 |
| CCATCTGGCC | CCAGTGCTGC | AATGATACCG | CGAGACCCAC | GCTCACCGGC 4200 |
| TCCAGATTTA | TCAGCAATAA | ACCAGCCAGC | CGGAAGGGCC | GAGCGCAGAA 4250 |
| GTGGTCCTGC | AACTTTATCC | GCCTCCATCC | AGTCTATTAA | TTGTTGCCGG 4300 |
| GAAGCTAGAG | TAAGTAGTTC | GCCAGTTAAT | AGTTTGCGCA | ACGTTGTTGC 4350 |
| CATTGCTGCA | GGCATCGTGG | TGTCACGCTC | GTCGTTTGGT | ATGGCTTCAT 4400 |
| TCAGCTCCGG | TTCCCAACGA | TCAAGGCGAG | TTACATGATC | CCCCATGTTG 4450 |
| TGCAAAAAAG | CGGTTAGCTC | CTTCGGTCCT | CCGATCGTTG | TCAGAAGTAA 4500 |
| GTTGGCCGCA | GTGTTATCAC | TCATGGTTAT | GGCAGCACTG | CATAATTCTC 4550 |
| TTACTGTCAT | GCCATCCGTA | AGATGCTTTT | CTGTGACTGG | TGAGTACTCA 4600 |
| ACCAAGTCAT | TCTGAGAATA | GTGTATGCGG | CGACCGAGTT | GCTCTTGCCC 4650 |
| GGCGTCAACA | CGGGATAATA | CCGCGCCACA | TAGCAGAACT | TTAAAAGTGC 4700 |
| TCATCATTGG | AAAACGTTCT | TCGGGGCGAA | AACTCTCAAG | GATCTTACCG 4750 |
| CTGTTGAGAT | CCAGTTCGAT | GTAACCCACT | CGTGCACCCA | ACTGATCTTC 4800 |
| AGCATCTTTT | ACTTTCACCA | GCGTTTCTGG | GTGAGCAAAA | ACAGGAAGGC 4850 |
| AAAATGCCGC | AAAAAAGGGA | ATAAGGGCGA | CACGGAAATG | TTGAATACTC 4900 |
| ATACTCTTCC | TTTTTCAATA | TTATTGAAGC | ATTTATCAGG | GTTATTGTCT 4950 |
| CATGAGCGGA | TACATATTTG | AATGTATTTA | GAAAAATAAA | CAAATAGGGG 5000 |
| TTCCGCGCAC | ATTTCCCCGA | AAAGTGCCAC | CTGACGTCTA | AGAAACCATT 5050 |
| ATTATCATGA | CATTAACCTA | TAAAAATAGG | CGTATCACGA | GGCCCTTTCG 5100 |
| TCTTCAAGAA 5110 | | | | |

(2) INFORMATION FOR SEQ ID NO:16:

(i) SEQUENCE CHARACTERISTICS:
  (A) LENGTH: 23 Base pairs
  (B) TYPE: Nucleic Acid
  (C) STRANDEDNESS: Double
  (D) TOPOLOGY: Linear (ii) MOLECULE TYPE: Other nucleic acid
  (A) DESCRIPTION: Consensus sequence of a T7 RNA
   polymerase promoter (iii) HYPOTHETICAL: No (iv) ANTI-SENSE: No (v) FRAGMENT TYPE: Not applicable (vi) ORIGINAL SOURCE:
  (A) ORGANISM: Bacteriophage T7
  (B) STRAIN: Wild-type
  (C) INDIVIDUAL ISOLATE: Not applicable
  (D) DEVELOPMENTAL STAGE: Not applicable
  (E) HAPLOTYPE: Not applicable
  (F) TISSUE TYPE: Not applicable
  (G) CELL TYPE: Not applicable
  (H) ORGANELLE: Not applicable (vii) IMMEDIATE SOURCE:
  (A) LIBRARY: Not applicable
  (B) CLONE: Not Applicable (v i i i) POSITION IN GENOME:
        (A) CHROMOSOME/SEGMENT: Not applicable
        (B) MAP POSITION: Not applicable
        (C) UNITS: Not applicable (i x) FEATURE:
        (A) NAME/KEY: Consensus T7 RNA polymerase promoter
        (B) LOCATION: 1 to 23
        (C) IDENTIFICATION METHOD: Sequence comparison of the 17
            different T7 promoters.
        (D) OTHER INFORMATION: The consensus sequence recognized
            by T7 RNA polymerase.

(x) PUBLICATION INFORMATION:
        (A) AUTHORS: Dunn, J. J., and Studier, F. W.
        (B) TITLE: Complete nucleotide sequence of bacteriophage
            T7 DNA and the locations of T7 genetic elements.
        (C) JOURNAL: Journal of Molecular Biology
        (D) VOLUME: 166
        (E) ISSUE:
        (F) PAGES: 477-535
        (G) DATE:
        (H) DOCUMENT NUMBER:
        (I) FILING DATE:
        (J) PUBLICATION DATE:
        (K) RELEVANT RESIDUES IN SEQ ID NO: 1 to 23

(i x) SEQUENCE DESCRIPTION: SEQ ID NO:16:

TAATACGACT CACTATAGGG AGA 23

(2) INFORMATION FOR SEQ ID NO:17:

(i) SEQUENCE CHARACTERISTICS:
        (A) LENGTH: 50 Bases
        (B) TYPE: Nucleic Acid
        (C) STRANDEDNESS: Single Stranded
        (D) TOPOLOGY: Linear (i i) MOLECULE TYPE: Other nucleic acid
        (A) DESCRIPTION:Synthetic deoxyoligonucleotide used
            in the construction of pCAT-10-1.This oligo is
            designated WT.

(i i i) HYPOTHETICAL: No (i v) ANTI-SENSE: No (v) FRAGMENT TYPE: Not applicable (v i) ORIGINAL SOURCE:
        (A) ORGANISM: Not applicable
        (B) STRAIN: Not applicable
        (C) INDIVIDUAL ISOLATE: Not applicable
        (D) DEVELOPMENTAL STAGE: Not applicable
        (E) HAPLOTYPE: Not applicable
        (F) TISSUE TYPE: Not applicable
        (G) CELL TYPE: Not applicable
        (H) ORGANELLE: Not applicable (v i i) IMMEDIATE SOURCE:
        (A) LIBRARY: Not applicable
        (B) CLONE: Not applicable (v i i i) POSITION IN GENOME:
        (A) CHROMOSOME/SEGMENT: Not applicable
        (B) MAP POSITION: Not applicable
        (C) UNITS: Not applicable (i x) FEATURE:
        (A) NAME/KEY: Synthetic deoxyoligonucleotide used in the
            construction of pCAT-10-1.This oligo is designated WT.
        (B) LOCATION: 1 to 50
        (C) IDENTIFICATION METHOD: Synthesized
        (D) OTHER INFORMATION: The oligo contains a consensus T7
            RNA polymerase promoter.

(x) PUBLICATION INFORMATION:
        (A) AUTHORS: Ikeda, R.A., Ligman, C.M., and Warshamana, G.S.
        (B) TITLE: T7 promoter contacts essential for promoter
            activity in vivo (C) JOURNAL: Nucleic Acids Research
(D) VOLUME: 20
(E) ISSUE: 20
(F) PAGES: 2517-2524
(G) DATE: May 25, 1992
(H) DOCUMENT NUMBER:
(I) FILING DATE:
(J) PUBLICATION DATE:
(K) RELEVANT RESIDUES IN SEQ ID NO: 1 to 50

(ix) SEQUENCE DESCRIPTION: SEQ ID NO:17:

CTGAATTCGA AATTAATACG ACTCACTATA GGGAGAAAGC TTGGTACCAG 50

(2) INFORMATION FOR SEQ ID NO:18:

(i) SEQUENCE CHARACTERISTICS:
(A) LENGTH: 50 Bases
(B) TYPE: Nucleic Acid
(C) STRANDEDNESS: Single Stranded
(D) TOPOLOGY: Linear (ii) MOLECULE TYPE: Other nucleic acid
(A) DESCRIPTION:Synthetic deoxyoligonucleotide used
in the construction of pCM-B#pyright (c) 1990, Microsoft Corp
designated B.

(iii) HYPOTHETICAL: No (iv) ANTI-SENSE: No (v) FRAGMENT TYPE: Not applicable (vi) ORIGINAL SOURCE:
(A) ORGANISM: Not applicable
(B) STRAIN: Not applicable
(C) INDIVIDUAL ISOLATE: Not applicable
(D) DEVELOPMENTAL STAGE: Not applicable
(E) HAPLOTYPE: Not applicable
(F) TISSUE TYPE: Not applicable
(G) CELL TYPE: Not applicable
(H) ORGANELLE: Not applicable (vii) IMMEDIATE SOURCE:
(A) LIBRARY: Not applicable
(B) CLONE: Not applicable (viii) POSITION IN GENOME:
(A) CHROMOSOME/SEGMENT: Not applicable
(B) MAP POSITION: Not applicable
(C) UNITS: Not applicable (ix) FEATURE:
(A) NAME/KEY: Synthetic deoxyoligonucleotide used in the
construction of pCM-B#pyright (c) 1990, Microsoft Corp
(B) LOCATION: 1 to 50
(C) IDENTIFICATION METHOD: Synthesized
(D) OTHER INFORMATION: The oligo contains a randomly
mutagenized T7 RNA polymerase promoter. The bases listed
in lower cases have a 96.1% probability of being the base
listed and a 3.9% probability of being one of the other
three possibile bases.

(x) PUBLICATION INFORMATION:
(A) AUTHORS: Ikeda, R.A., Ligman, C.M., and Warshamana, G.S.
(B) TITLE: T7 promoter contacts essential for promoter
activity in vivo
(C) JOURNAL: Nucleic Acids Research
(D) VOLUME: 20
(E) ISSUE: 20
(F) PAGES: 2517-2524
(G) DATE: May 25, 1992
(H) DOCUMENT NUMBER:
(I) FILING DATE:
(J) PUBLICATION DATE:
(K) RELEVANT RESIDUES IN SEQ ID NO: 1 to 50

(ix) SEQUENCE DESCRIPTION: SEQ ID NO:18:

CTGAATTCGa aattaatacg actcactata gggagaAAGC TTGGTACCAG 50

( 2 ) INFORMATION FOR SEQ ID NO:19:

( i ) SEQUENCE CHARACTERISTICS:
            ( A ) LENGTH: 50 Bases
            ( B ) TYPE: Nucleic Acid
            ( C ) STRANDEDNESS: Single Stranded
            ( D ) TOPOLOGY: Linear ( i i ) MOLECULE TYPE: Other nucleic acid
           ( A ) DESCRIPTION: Synthetic deoxyoligonucleotide used
                in the construction of pCM-T#pyright (c) 1990, Microsoft Corp
                designated T.

( i i i ) HYPOTHETICAL: No ( i v ) ANTI-SENSE: No ( v ) FRAGMENT TYPE: Not applicable ( v i ) ORIGINAL SOURCE:
           ( A ) ORGANISM: Not applicable
           ( B ) STRAIN: Not applicable
           ( C ) INDIVIDUAL ISOLATE: Not applicable
           ( D ) DEVELOPMENTAL STAGE: Not applicable
           ( E ) HAPLOTYPE: Not applicable
           ( F ) TISSUE TYPE: Not applicable
           ( G ) CELL TYPE: Not applicable
           ( H ) ORGANELLE: Not applicable ( v i i ) IMMEDIATE SOURCE:
           ( A ) LIBRARY: Not applicable
           ( B ) CLONE: Not applicable ( v i i i ) POSITION IN GENOME:
           ( A ) CHROMOSOME/SEGMENT: Not applicable
           ( B ) MAP POSITION: Not applicable
           ( C ) UNITS: Not applicable ( i x ) FEATURE:
           ( A ) NAME/KEY: Synthetic deoxyoligonucleotide used in the
                construction of pCM-T#pyright (c) 1990, Microsoft Corp
           ( B ) LOCATION: 1 to 50
           ( C ) IDENTIFICATION METHOD: Synthesized
           ( D ) OTHER INFORMATION: The oligo contains a randomly
                mutagenized T7 RNA polymerase promoter. The bases listed
                in lower cases have a 96.1% probability of being the base
                listed and a 3.9% probability of being one of the other
                three possible bases.

( x ) PUBLICATION INFORMATION:
           ( A ) AUTHORS: Ikeda, R.A., Ligman, C.M., and Warshamana, G.S.
           ( B ) TITLE: T7 promoter contacts essential for promoter
                activity in vivo
           ( C ) JOURNAL: Nucleic Acids Research
           ( D ) VOLUME: 20
           ( E ) ISSUE: 20
           ( F ) PAGES: 2517-2524
           ( G ) DATE: May 25, 1992
           ( H ) DOCUMENT NUMBER:
           ( I ) FILING DATE:
           ( J ) PUBLICATION DATE:
           ( K ) RELEVANT RESIDUES IN SEQ ID NO: 1 to 50

( i x ) SEQUENCE DESCRIPTION: SEQ ID NO:19:

CTAGTACTga    aattaatacg    actcactata    gggagaAAGC    TTGGTACCAG    50

( 2 ) INFORMATION FOR SEQ ID NO:20:

( i ) SEQUENCE CHARACTERISTICS:
            ( A ) LENGTH: 50 Bases
            ( B ) TYPE: Nucleic Acid
            ( C ) STRANDEDNESS: Single Stranded
            ( D ) TOPOLOGY: Linear ( i i ) MOLECULE TYPE: Other nucleic acid
           ( A ) DESCRIPTION:Synthetic deoxyoligonucleotide used
                in the construction of pCM-P#pyright (c) 1990, Microsoft Corp
                designated P.

(iii) HYPOTHETICAL: No (iv) ANTI-SENSE: No (v) FRAGMENT TYPE: Not applicable (vi) ORIGINAL SOURCE:
  (A) ORGANISM: Not applicable
  (B) STRAIN: Not applicable
  (C) INDIVIDUAL ISOLATE: Not applicable
  (D) DEVELOPMENTAL STAGE: Not applicable
  (E) HAPLOTYPE: Not applicable
  (F) TISSUE TYPE: Not applicable
  (G) CELL TYPE: Not applicable
  (H) ORGANELLE: Not applicable (vii) IMMEDIATE SOURCE:
  (A) LIBRARY: Not applicable
  (B) CLONE: Not applicable (viii) POSITION IN GENOME:
  (A) CHROMOSOME/SEGMENT: Not applicable
  (B) MAP POSITION: Not applicable
  (C) UNITS: Not applicable (ix) FEATURE:
  (A) NAME/KEY: Synthetic deoxyoligonucleotide used in the
       construction of pCM-P#pyright (c) 1990, Microsoft Corp
  (B) LOCATION: 1 to 50
  (C) IDENTIFICATION METHOD: Synthesized
  (D) OTHER INFORMATION: The oligo contains a T7 promoter that
       is randomly mutagenized at promoter positions -9 through
       - 7. The bases listed in lower cases have a 67%
       probability of being the base listed and a 33%
       probability of being one of the other three possible
       bases.

(x) PUBLICATION INFORMATION:
  (A) AUTHORS: Ikeda, R.A., Ligman, C.M., and Warshamana, G.S.
  (B) TITLE: T7 promoter contacts essential for promoter
       activity in vivo
  (C) JOURNAL: Nucleic Acids Research
  (D) VOLUME: 20
  (E) ISSUE: 20
  (F) PAGES: 2517-2524
  (G) DATE: May 25, 1992
  (H) DOCUMENT NUMBER:
  (I) FILING DATE:
  (J) PUBLICATION DATE:
  (K) RELEVANT RESIDUES IN SEQ ID NO: 1 to 50

(ix) SEQUENCE DESCRIPTION: SEQ ID NO:20:

CTAGTACTGA AATTAATACG ActcACTATA GGGAGAAAGC TTGGTACCAG  50

(2) INFORMATION FOR SEQ ID NO:21:

(i) SEQUENCE CHARACTERISTICS:
    (A) LENGTH: 50 Bases
    (B) TYPE: Nucleic Acid
    (C) STRANDEDNESS: Single Stranded
    (D) TOPOLOGY: Linear (ii) MOLECULE TYPE: Other nucleic acid
    (A) DESCRIPTION:Synthetic deoxyoligonucleotide used in
         the construction of pCM-C#pyright (c) 1990, Microsoft Corp
         designated C.

(iii) HYPOTHETICAL: No (iv) ANTI-SENSE: No (v) FRAGMENT TYPE: Not applicable (vi) ORIGINAL SOURCE:
    (A) ORGANISM: Not applicable
    (B) STRAIN: Not applicable
    (C) INDIVIDUAL ISOLATE: Not applicable
    (D) DEVELOPMENTAL STAGE: Not applicable
    (E) HAPLOTYPE: Not applicable
    (F) TISSUE TYPE: Not applicable (G) CELL TYPE: Not applicable
(H) ORGANELLE: Not applicable (vii) IMMEDIATE SOURCE:
    (A) LIBRARY: Not applicable
    (B) CLONE: Not applicable (viii) POSITION IN GENOME:
    (A) CHROMOSOME/SEGMENT: Not applicable
    (B) MAP POSITION: Not applicable
    (C) UNITS: Not applicable (ix) FEATURE:
    (A) NAME/KEY: Synthetic deoxyoligonucleotide used in the
        construction of pCM-C#pyright (c) 1990, Microsoft Corp
    (B) LOCATION: 1 to 50
    (C) IDENTIFICATION METHOD: Synthesized
    (D) OTHER INFORMATION: The oligo contains a T7 RNA
        polymerase promoter that carries an A to C mutation at
        position -10 of the promoter. This base is shown as a
        lower case letter.

(x) PUBLICATION INFORMATION:
    (A) AUTHORS: Ikeda, R.A., Ligman, C.M., and Warshamana, G.S.
    (B) TITLE: T7 promoter contacts essential for promoter
        activity in vivo
    (C) JOURNAL: Nucleic Acids Research
    (D) VOLUME: 20
    (E) ISSUE: 20
    (F) PAGES: 2517-2524
    (G) DATE: May 25, 1992
    (H) DOCUMENT NUMBER:
    (I) FILING DATE:
    (J) PUBLICATION DATE:
    (K) RELEVANT RESIDUES IN SEQ ID NO: 1 to 50

(ix) SEQUENCE DESCRIPTION: SEQ ID NO:21:

```
CTAGTACTGA AATTAATACG cCTCACTATA GGGAGAAAGC TTGGTACCAG   50
```

(2) INFORMATION FOR SEQ ID NO:22:

(i) SEQUENCE CHARACTERISTICS:
        (A) LENGTH: 50 Bases
        (B) TYPE: Nucleic Acid
        (C) STRANDEDNESS: Single Stranded
        (D) TOPOLOGY: Linear (ii) MOLECULE TYPE: Other nucleic acid
        (A) DESCRIPTION:Synthetic deoxyoligonucleotide used
            in the construction of pCM-G#pyright (c) 1990, Microsoft Corp
            designated G.

(iii) HYPOTHETICAL: No (iv) ANTI-SENSE: No (v) FRAGMENT TYPE: Not applicable (vi) ORIGINAL SOURCE:
        (A) ORGANISM: Not applicable
        (B) STRAIN: Not applicable
        (C) INDIVIDUAL ISOLATE: Not applicable
        (D) DEVELOPMENTAL STAGE: Not applicable
        (E) HAPLOTYPE: Not applicable
        (F) TISSUE TYPE: Not applicable
        (G) CELL TYPE: Not applicable
        (H) ORGANELLE: Not applicable (vii) IMMEDIATE SOURCE:
        (A) LIBRARY: Not applicable
        (B) CLONE: Not applicable (viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY: Synthetic deoxyoligonucleotide used in the
            construction of pCM-G#pyright (c) 1990, Microsoft Corp (B) LOCATION: 1 to 50
                    (C) IDENTIFICATION METHOD: Synthesized
                    (D) OTHER INFORMATION: The oligo contains a T7 RNA
                            polymerase promoter that carries an A to G mutation as
                            position -10 of the promoter. This base is shown as a
                            lower case letter.

(x) PUBLICATION INFORMATION:
                    (A) AUTHORS: Ikeda, R.A., Ligman, C.M., and Warshamana, G.S.
                    (B) TITLE: T7 promoter contacts essential for promoter
                            activity in vivo
                    (C) JOURNAL: Nucleic Acids Research
                    (D) VOLUME: 20
                    (E) ISSUE: 20
                    (F) PAGES: 2517-2524
                    (G) DATE: May 25, 1992
                    (H) DOCUMENT NUMBER:
                    (I) FILING DATE:
                    (J) PUBLICATION DATE:
                    (K) RELEVANT RESIDUES IN SEQ ID NO: 1 to 50

(ix) SEQUENCE DESCRIPTION: SEQ ID NO:22:

CTAGTACTGA AATTAATACG gCTCACTATA GGGAGAAAGC TTGGTACCAG    50

(2) INFORMATION FOR SEQ ID NO:23:

(i) SEQUENCE CHARACTERISTICS:
                    (A) LENGTH: 14 Bases
                    (B) TYPE: Nucleic Acid
                    (C) STRANDEDNESS: Single Stranded
                    (D) TOPOLOGY: Linear (ii) MOLECULE TYPE: Other nucleic acid
                    (A) DESCRIPTION: Synthetic deoxyoligonucleotide used
                            in the construction of pCM-X#pyright (c) 1990, Microsoft Corp
                            designated "Primer."

(iii) HYPOTHETICAL: No (iv) ANTI-SENSE: No (v) FRAGMENT TYPE: Not applicable (vi) ORIGINAL SOURCE:
                    (A) ORGANISM: Not applicable
                    (B) STRAIN: Not applicable
                    (C) INDIVIDUAL ISOLATE: Not applicable
                    (D) DEVELOPMENTAL STAGE: Not applicable
                    (E) HAPLOTYPE: Not applicable
                    (F) TISSUE TYPE: Not applicable
                    (G) CELL TYPE: Not applicable
                    (H) ORGANELLE: Not applicable (vii) IMMEDIATE SOURCE:
                    (A) LIBRARY: Not applicable
                    (B) CLONE: Not applicable (viii) POSITION IN GENOME:
                    (A) CHROMOSOME/SEGMENT: Not applicable
                    (B) MAP POSITION: Not applicable
                    (C) UNITS: Not applicable (ix) FEATURE:
                    (A) NAME/KEY: Synthetic deoxyoligonucleotide used in the
                            construction of pCM-X#pyright (c) 1990, Microsoft Corp
                            " Primer."
                    (B) LOCATION: 1 to 14
                    (C) IDENTIFICATION METHOD: Synthesized
                    (D) OTHER INFORMATION: The "Primer"oligo is complementary
                            to the 14 nucleotides at the 3'end of oligos
                            WT, B, T, P, C, and G, and is used for priming the
                            synthesis of a DNA strand complementary to the
                            WT, B, T, P, C, and G oligos.

(x) PUBLICATION INFORMATION:
                    (A) AUTHORS: Ikeda, R.A., Ligman, C.M., and Warshamana, G.S.
                    (B) TITLE: T7 promoter contacts essential for promoter
                            activity in vivo
                    (C) JOURNAL: Nucleic Acids Research
                    (D) VOLUME: 20

(E) ISSUE: 20
(F) PAGES: 2517-2524
(G) DATE: May 25, 1992
(H) DOCUMENT NUMBER:
(I) FILING DATE:
(J) PUBLICATION DATE:
(K) RELEVANT RESIDUES IN SEQ ID NO: 1 to 14

(ix) SEQUENCE DESCRIPTION: SEQ ID NO:23:

CTGGTACCAA GCTT 14

MUTANT T7 RNA POLYMERASE GP1(LYS222) EXHIBITING ALTERED PROMOTER RECOGNITION

STATEMENT OF GOVERNMENT INTEREST

This work was supported by a FIRST grant (AI24905) from the National Institutes of Allergies and Infectious Diseases. Additionally, the major equipment used in this work was part of a Biological Instrumentation Facility that was assembled with support from the National Science Foundation under Grant No. DIR-9011409. The U.S. Government may have certain rights to the invention.

BACKGROUND OF THE INVENTION

1. Field of the Invention

This invention generally relates to the alteration of a first plasmid to produce a T7 RNA polymerase capable of recognizing a T7 promoter on a second plasmid and transcribing a gene that is cloned behind the promoter resulting in changed properties to an *E. coli* in which the two plasmids are harbored. This invention specifically relates to conferring chloramphenicol ("cam") resistance to *E. coli* harboring a pKGP-HA1mut4 plasmid producing the T7 RNA polymerase GP1(lys222) and a pCM-X# plasmid, specifically those selection plasmids listed in Table I and Table II.

2. Prior Art

Bacteriophage T7 RNA polymerase, the product of T7 gene 1, is a protein produced early in T7 infection; it is a single-chain enzyme with a molecular weight close to 100,000. It appears that the basis for the selectivity of the T7 RNA polymerase is the interaction of the RNA polymerase with a relatively large promoter sequence, a sequence large enough that it is unlikely to be found by chance in any unrelated DNA. In the case of T7, the highly conserved promoter sequence appears to consist of approximately 23 continuous base pairs, which includes the start site for the RNA chain. If exact specification of even as few as 15 of these base pairs were required for initiation of chains, chance occurrence of a functional promoter would be expected less than once in a billion nucleotides of DNA.

The RNA polymerase is a simple single subunit enzyme of 883 amino acids (98.6 kDa) that requires no auxiliary factors for accurate transcription, in vitro. T7 RNA polymerase alone is able to recognize its promoters, initiate transcription, elongate the RNA transcript, and terminate transcription [Chamberlin, M. and Ryan, T., *The Enzymes*, 15: 87–108 (1982); Bautz, E. K. F., *RNA Polymerase*, 273–284 (1976); Chamberlin, M. and Ring, J., *J. Biol. Chem.*, 248: 2235–2244 (1973); Chamberlin, M. and Ring, J., *J. Biol. Chem.* 248: 2245–2250 (1973)]. Comparison of the seventeen natural T7 RNA polymerase promoters yields a 23 base pair consensus sequence that includes the site of the initiation of transcription (+1) and extends from −17 to +6, as shown in FIG. 1 [Moffatt, B. A., et al., *J. Mol. Biol*, 173: 265–269 (1984); Dunn, J. J. and Studier, F. W., *J. Mol. Biol.* 166: 477–535 (1983); Studier, F. W. and Dunn, J. J., *Cold Spring Harbor Symp. Quant. Biol.*, 47: 999–1007 (1982); Oakley, J. L., et al., *Biochemistry*, 14: 4684–4691 (1979)]. In vitro studies of promoter dependent T7 RNA polymerase activity have defined the kinetics of transcription [Ikeda, R. A., et al, *J. Biol. Chem.*, 267: 2640–2649 (1992); Martin, B. A. and Coleman, J. E., *Biochemistry*, 26: 2690–2696 (1987)], the stability of the promoter polymerase complex [Muller, D. K., et al., *Biochemistry* 28: 3306–3313 (1989); Shi, Y. et al., *J. Biol. Chem.*, 263: 527–534 (1988); Gunderson, S. I., et al., *Biochemistry*, 26: 1539–1546 (1987); Basu, S. and Maitra, U., *J. Mol. Biol.*, 190: 425–437 (1986); Ikeda, R. A. and Richardson, C. C., *Proc. Natl. Acad. Sci. USA*, 83: 3614–3618 (1986); Smeekens, S. P. and Romano, L. J., *Nucl. Acids Res.*, 14: 2811–2827 (1986)], the contribution of abortive initiation to promoter efficiency [Ikeda, R. A., *J. Biol. Chem.*, 267: 11322–11328 (1992)], and the DNA contacts essential for promoter activity [Ikeda, R. A., et al., *Biochemistry*, 31: 9073–9080 (1992); Ikeda, R. A., et al., *Nucl. Acids Res.*, 20: 2517–2524 (1992)]. The data suggest that the T7 promoter is organized into two domains: an initiation domain from −4 to +5 and a binding domain from −5 to −12 [Chapman, K. A., et al., *Nucl. Acids Res.*, 16: 4511–4524 (1988); Chapman, K. A. and Burgess, R. R., *Nucl. Acids Res.*, 15: 5413–5432 (1987)]. Single base changes in the binding domain of the T7 promoter reduce or eliminate promoter binding, but have little effect on the initiation of transcription. In contrast, single base changes in the initiation domain of the promoter have little effect on promoter binding but reduce the rate of initiation.

We recently described two compatible plasmids that together can be used to determine whether a mutant T7 promoter is active or inactive in vivo [Ikeda, R. A., et al., *Biochemistry*, 31: 9073–9080 (1992); Ikeda, R. A., et al., *Nucl. Acids Res.*, 20: 2517–2524 (1992)]. The first plasmid, pKGP1-1, is a pACYC177 [Chang, A. C. Y. and Cohen, S. N., *J. Bacteriol*, 134: 1141–1156 (1978)] derivative that carries T7 gene 1 (the gene encoding T7 RNA polymerase) ligated to a tac promoter [deBoer, H. A., et al., *Proc. Natl. Acad Sci. USA*, 80: 21–25 (1983); deBoer, H. A., et al., *Promoters, Structure and Function*, 462–481 (1982)], while the second plasmid, pCM-X#, is a pKK232-8 [Brosius, J., and Lupski, J. R., *Methods in Enzymology*, 153: 54–68 (1987); Brosiusm J., and Holy, A., *Proc. Natl. Acad. Sci. USA*, 81: 6929–6933 (1984)] derivative that carries the gene encoding CAT ligated to potential T7 promoters. pCM-X# is the general designation for this family of plasmids derived from pKK232-8. A specific plasmid within this family is designated with a letter and a number in place of X#. The following abbreviations are used throughout this specification: $A_x$, absorbance at the designated wavelength (x) in nm; amp, ampicillin; bla, β-lactamase; BSA, bovine serum albumin; CAT, chloramphenicol acetyl transferase; cam, chloramphenicol; CoA, coenzyme A; DTNB, 5,5′-dithio-bis-(2-nitrobenzoic acid); DTT, dithiothreitol; EDTA, ethylenediamine tetraacetic acid; IPTG, isopropyl-β-D-thiogalactopyranoside; kan, kanamycin; LB, Luria-Bertani (medium); NTP, nucleoside triphosphate; Tris, tris (hydroxymethyl) aminomethane; u, units. *E. coli* harboring these two plasmids are cam resistant if the pCM-X# plasmid carries an active T7 promoter and are cam sensitive if the pCM-X# plasmid carries an inactive T7 promoter. The pCM-X# plasmids that carry T7 promoter point mutants that destroy promoter activity are designated inactive pCM-X# plasmids, while pCM-X# plasmids that carry T7 promoter point mutants with moderate activity or wild-type activity are designated intermediate pCM-X# plasmids and strong pCM-X# plasmids, respectively. Point mutations that were found to inactivate the T7 promoter are a Cytidine ("C") to Adenosine ("A") (plasmid pCM-P1031) or Guanosine ("G") (plasmid pCM- P1208) substitution at −7, a Thymidine ("T") (plasmid pCM-T286) to A substitution at −8, a C to A (plasmid pCM-T270), T (plasmid pCM-P1087) or G (plasmid pCM-P1160) substitution at −9, and a G to T (plasmid pCM-T297) substitution at −11 [Ikeda, R. A., et al., Biochemistry, 31: 9073–9080 (1992); Ikeda, R. A., et al., Nucl. Acids Res., 20: 2517–2524 (1992), both incorporated herein by this reference].

Although much is known about the activity of T7 RNA polymerase and the structure of the T7 promoter, little is known about the structure-function relationships of T7 RNA polymerase itself. Several researchers have noted that limited proteolytic cleavage of T7 RNA polymerase yields a 20 kDa amino-terminal fragment and an 80 kDa carboxyl terminal fragment [Ikeda, R. A. and Richardson, C. C., J. Biol. Chem., 262: 3790–3799 (1987); Davanloo, P., et al., Proc. Natl. Acad. Sci. USA, 81: 2035–2039 (1984)]. The carboxyl terminal fragment can initiate RNA synthesis, but cannot extend the transcript [Muller, D. K., et al., Biochemistry, 28: 3306–3313 (1988)]. It has been suggested that the amino-terminal domain of T7 RNA polymerase contains a nonspecific RNA binding site that stabilizes the T7 transcription complex and allows for processive RNA synthesis. Other structural studies have shown that DNA binding and polymerase activities are separable functions in T7 RNA polymerase. Amino acid insertions into the reading frame of T7 RNA polymerase at residues 640, 648, or 881 inactivate polymerase activity, but do not disrupt promoter binding; while insertions at residues 159, 222, 240, or 242 disrupt DNA binding but do not inactivate polymerase activity [Gross, L., et al., J. Mol. Biol., 228: 488–505 (1992); Patra, D., et al., J. Mol. Biol., 224: 307–318 (1992)]. Finally, replacement of Asn748 of T7 RNA polymerase by the corresponding residue found in T3 RNA polymerase (Asp) alters promoter recognition by the enzyme. The Asp748 T7 RNA polymerase prefers a promoter with C's at positions −11 and −10, the bases normally found in the T3 promoter [Raskin, C. A., et al., J. Mol. Biol., 228: 506–515 (1993); Joho, K. E., et al., J. Mol. Biol., 215: 31–39 (1990); Klement, J. F., et al., J. Mol. Biol., 215:21–29 (1990)].

Further characterization of promoter recognition and utilization by T7 RNA polymerase would be greatly aided by the identification and characterization of mutant T7 RNA polymerase with altered promoter recognition. We report here the use of the compatible plasmids pKGP1-1 and pCM-X# to select a mutant T7 RNA polymerase with an expanded range of promoter recognition and the characterization of the specificity of the mutant enzyme.

BRIEF SUMMARY OF THE INVENTION

The compatible plasmids pKGP1-1 and pCM-X# will confer chloramphenicol resistance to E. coli harboring the two plasmids if the T7 RNA polymerase produced from pKGP1-1 can recognize the T7 promoter carried on pCM-X# and transcribe the CAT gene that is cloned behind the promoter. When E. coli harbor pKGP1-1 and a pCM-X# plasmid that carries a point mutation in the T7 promoter that destroys promoter activity (termed an inactive pCM-X#), the T7 RNA polymerase will not utilize the T7 promoter point mutant, will not produce CAT, and will not induce chloramphenicol resistance. The selection of mutants of T7 RNA polymerase that exhibit altered promoter recognition was pursued by randomly mutagenizing pKGP1-1 with aqueous hydroxylamine, cotransforming E. coli with the mutagenized pKGP1-1 and a mixture of seven different inactive pCM-X# plasmids, and isolating and characterizing the RNA polymerase that was present in those colonies that exhibited chloramphenicol resistance. It was established that E. coli harboring the mutant plasmid pKGP-HA1mut4 and an inactive pCM-X# are chloramphenicol resistant and that the mutation responsible for the expression of CAT from the inactive pCM-X# plasmid is a G to A transition at nucleotide 664 of T7 gene 1 that converts glutamic acid(222) to lysine. Apparently this mutation expands the range of T7 promoter sequences that can be utilized by the enzyme. The mutant T7 RNA polymerase, GP1(lys222), utilizes all seven inactive T7 promoter point mutants more efficiently than wild-type T7 RNA polymerase both in vivo and in vitro. Furthermore, the correlation of in vivo and in vitro promoter utilization suggests that the restoration of chloramphenicol resistance in the cotransformed E. coli results from the ability of GP1(lys222) to initiate transcription from T7 promoter point mutants that are normally inactive.

SUMMARY OF SEQUENCE LISTINGS

Various DNA sequences and protein sequences are referred to throughout this specification. Following is a chart of the sequence listings and their sequence identification number as contained on pages S1–S86. Sequence ID numbers 1 and 2 correspond to the invention disclosed and claimed herein. Sequence ID numbers 3–23 correspond to other DNA sequences which are discussed herein.

| SEQUENCE IDENTITY | SEQUENCE ID NO. |
| --- | --- |
| T7 RNA polymerase GP1(Lys222) (DNA sequence of the mutant RNA polymerase) | 1 |
| T7 RNA polymerase GP1(Lys222) (Protein sequence of the mutant RNA polymerase) | 2 |
| pKK232-8 (DNA sequence) | 3 |
| pCM-X# (DNA sequence) | 4 |
| pCAT10-1 (DNA sequence) | 5 |
| pCM-T297 (DNA sequence) | 6 |
| pCM-P1160 (DNA sequence) | 7 |
| pCM-T270 (DNA sequence) | 8 |
| pCM-P1087 (DNA sequence) | 9 |
| pCM-P1198 (DNA sequence) | 10 |
| pCM-T286 (DNA sequence) | 11 |
| pCM-B64 (DNA sequence) | 12 |
| pCM-P1208 (DNA sequence) | 13 |
| pCM-P1031 (DNA sequence) | 14 |
| pCM-T221 (DNA sequence) | 15 |
| Wild type T7 promoter (DNA sequence) | 16 |
| WT (DNA sequence in Table IV) | 17 |
| B (DNA sequence in Table IV) | 18 |
| T (DNA sequence in Table IV) | 19 |
| P (DNA sequence in Table IV) | 20 |
| C (DNA sequence in Table IV) | 21 |
| G (DNA sequence in Table IV) | 22 |
| Primer (DNA sequence in Table IV) | 23— |

pBR ori, colE1 origin of replication; rrnBT1T2/5S, transcriptional terminators from the *E. coli* 5S rRNA gene; ptac, tac promoter; mut T7 $\phi$10, wild-type or mutant T7 $\phi$10 promoter; T7 gene 1, gene encoding T7 RNA polymerase.

Figure 3:
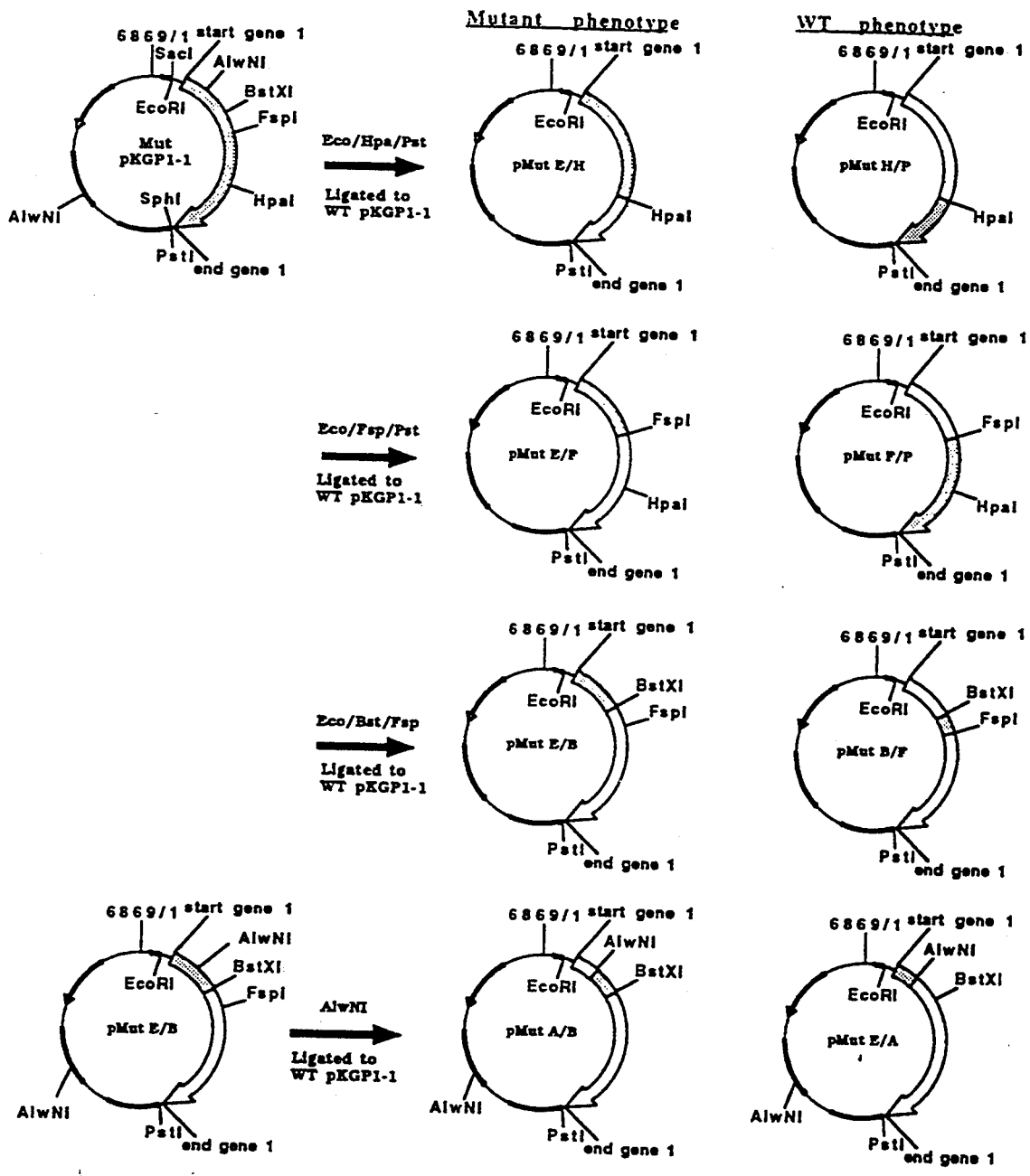

FIG. 3: Localization of the Mutation in pKGP-HA1-mut4. T7 gene 1 restriction fragments from pKGP-HA1mut4 were cloned into the corresponding sites of wild-type pKGP1-1. The restriction enzymes used to generate each set of clones are listed above each arrow. The newly constructed recombinant plasmids are shown on the left side of the arrow, and the T7 gene 1 restriction fragments ligated into wild-type pKGP1-1 are shown as shaded segments on the maps. The clones listed under Mutant Phenotype produced cam resistant *E. coli* in the cotransformation experiments. The clones listed under WT Phenotype produced cam sensitive *E. coli* in the cotransformation experiments.

Figure 4:
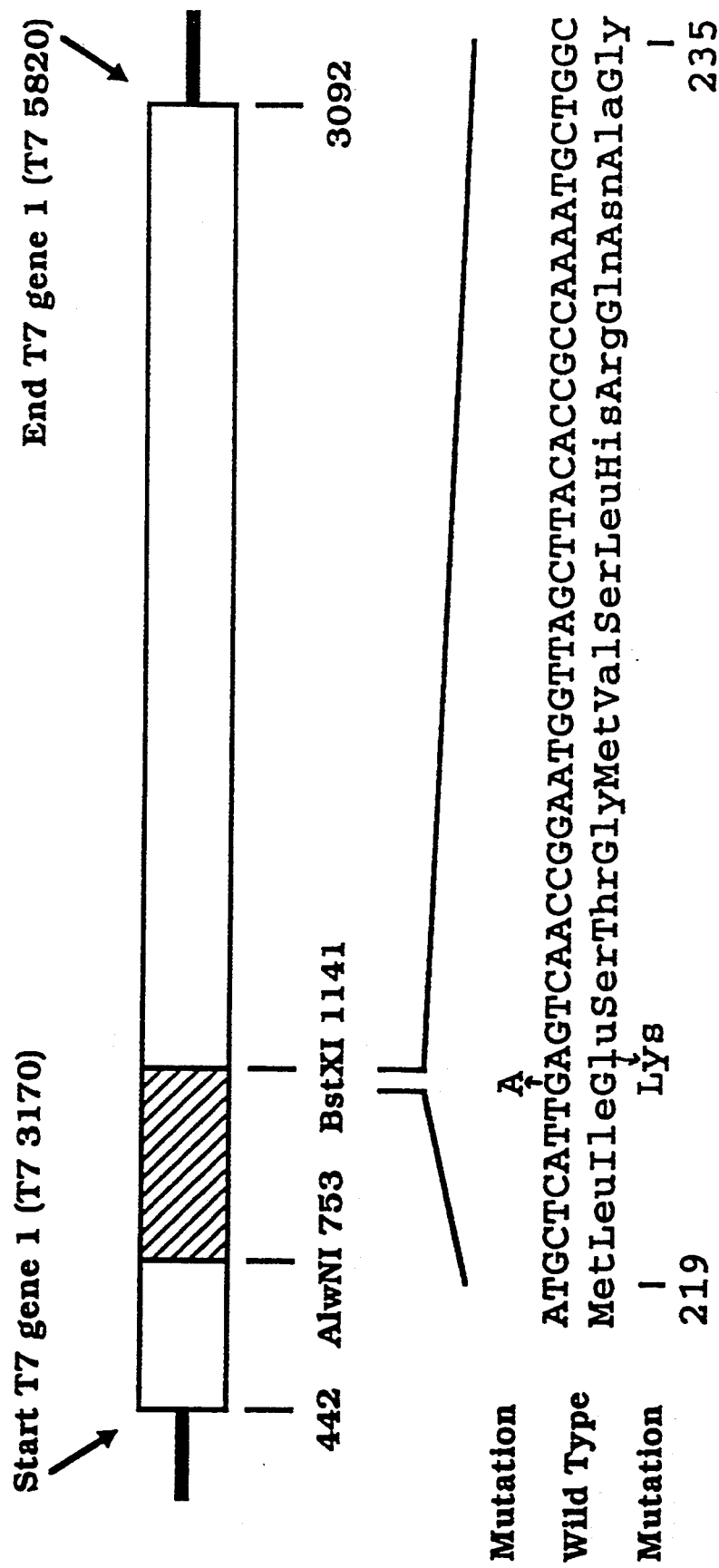

FIG. 4: Sequencing of pMutA/B Reveals a Single Mutation. The location and identity of the mutation in pMutA/B that is responsible for producing cam resistance in the cotransformation experiments is shown. The mutant restriction fragment ligated into the T7 gene 1 region of pMutA/B is shaded. The position of the start and end of T7 gene 1 is listed with respect to T7 (above the map) and with respect to pMutA/B (below the map). The amino acid sequence shown lists the amino acid positions within T7 gene 1.

Figure 5A:
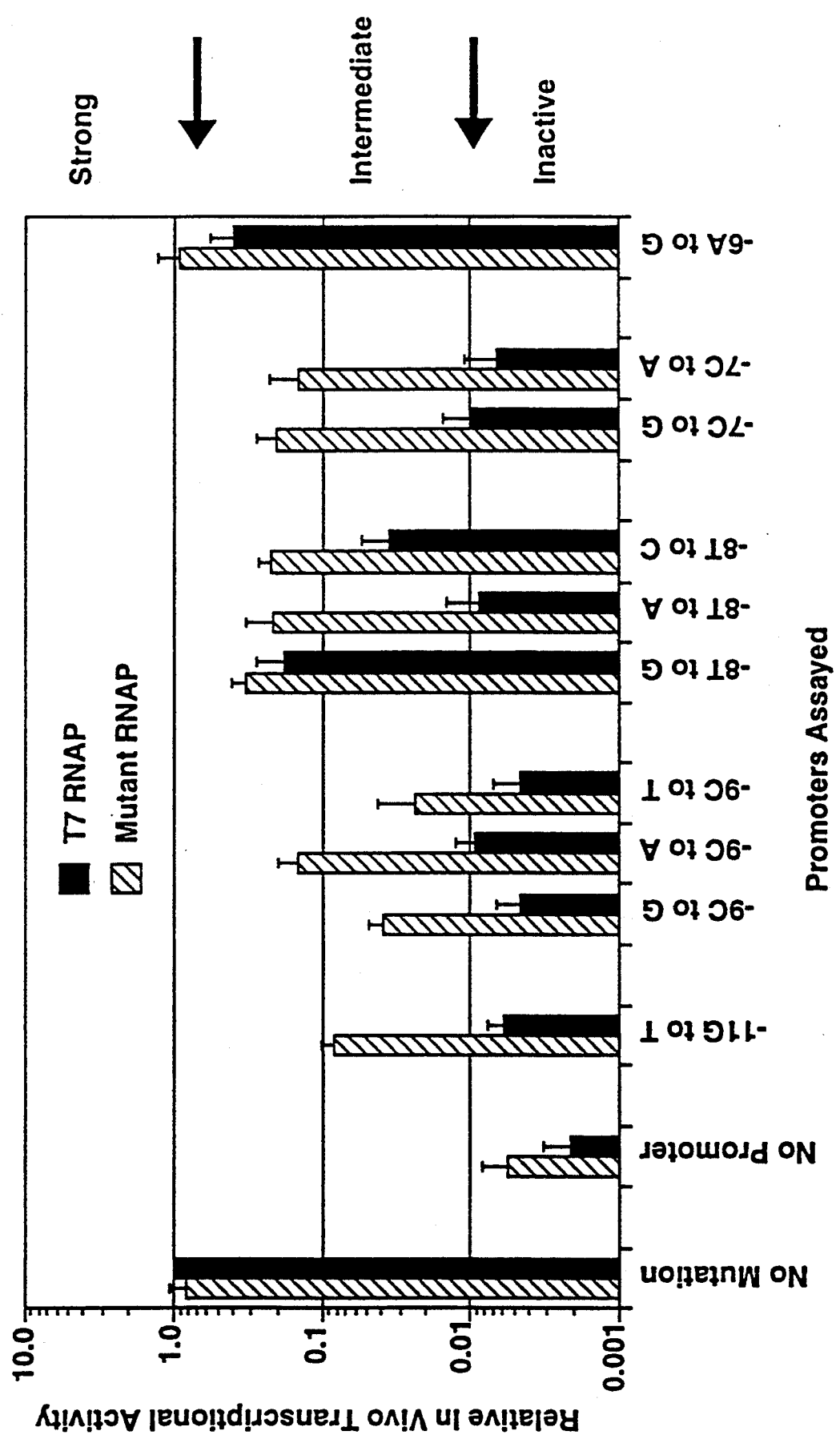
Figure 5B:
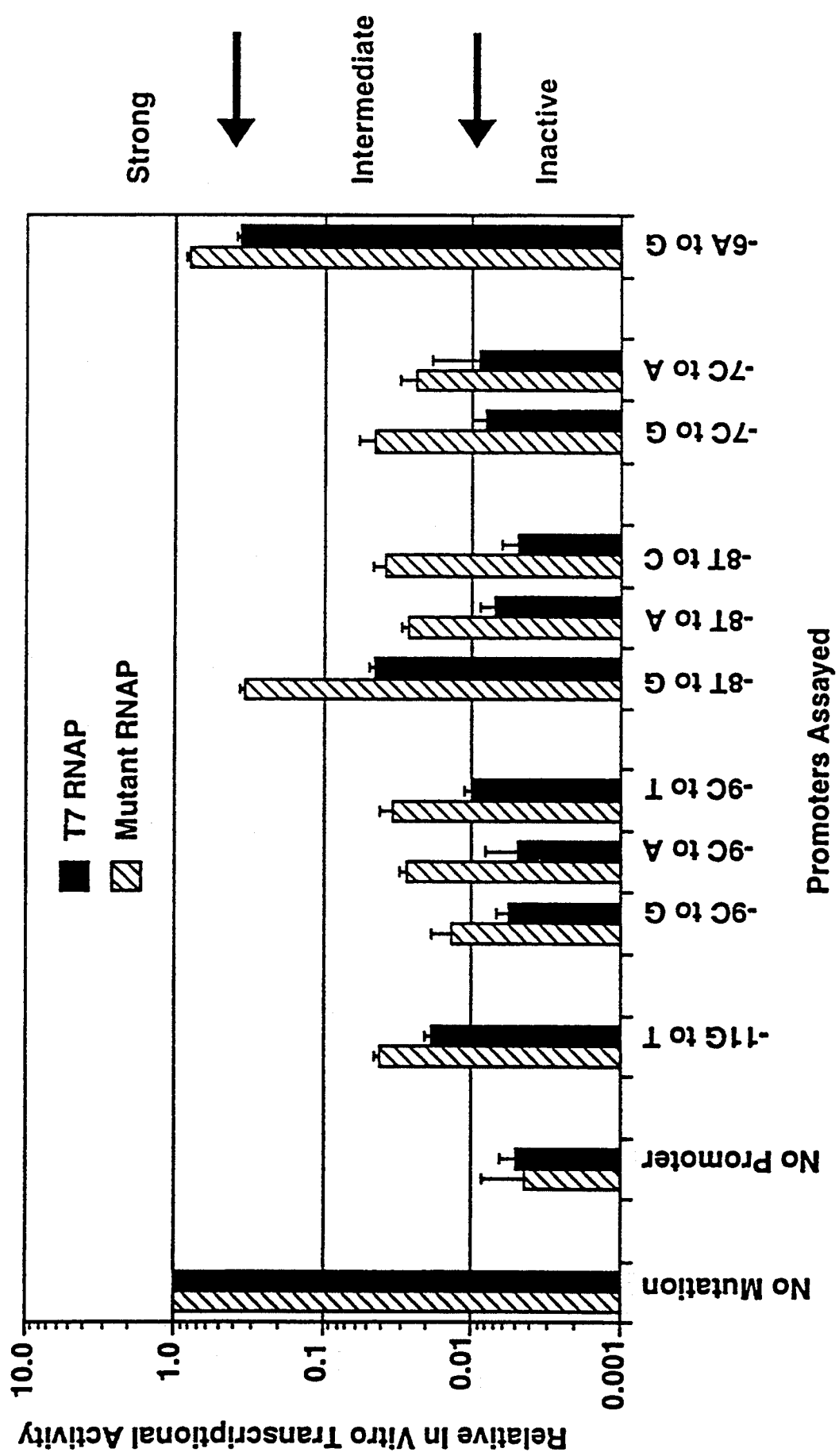

FIGS. 5–5B: Relative In Vitro (FIG. 5B) and In Vivo (FIG. 5A) Utilization of Potential T7 Promoters by GP1(lys222) and Wild-type T7 RNA Polymerase. The promoters are listed on the horizontal axis, and relative activity is represented along the vertical axis. The arrows on the right side of the graphs indicate the approximate activities that differentiate the inactive, intermediate, and strong promoters. The $-8$ T to G mutant is classified as an intermediate promoter, while the $-6$ A to G mutant shows some characteristics of a strong promoter, and the $-8$ T to C mutant shows some characteristics of an inactive promoter. For clarity, only the top halves of the error bars are shown; however, the error bars should extend below the tops of the data columns for a distance equivalent to the value that the error bars extend above the data columns on the logarithmic scale. FIG. 5A: Relative in vivo promoter utilization. The Relative In Vivo Transcriptional Activity (or Promoter Strength) is defined below in the section Methodology. The errors associated with these results were calculated by standard methods for the propagation of errors. No error bar is shown for use of the wild-type promoter by wild-type T7 RNA polymerase since the consensus T7 promoter has been defined to have a relative in vivo activity of 1.00. FIG. 5B: Relative in vitro promoter utilization. The Relative In Vitro Promoter Strength (or Promoter Strength) is defined in the section Methodology. The results are the average of the two time points of at least three different samples, and the error associated with the measurements is the greater of the standard deviation observed. No error bar is shown for use of the wild-type promoter by either wild-type T7 RNA polymerase or GP1(lys222) since the consensus T7 promoter has been defined to have a relative in vitro activity of 1.00.

Figure 6:
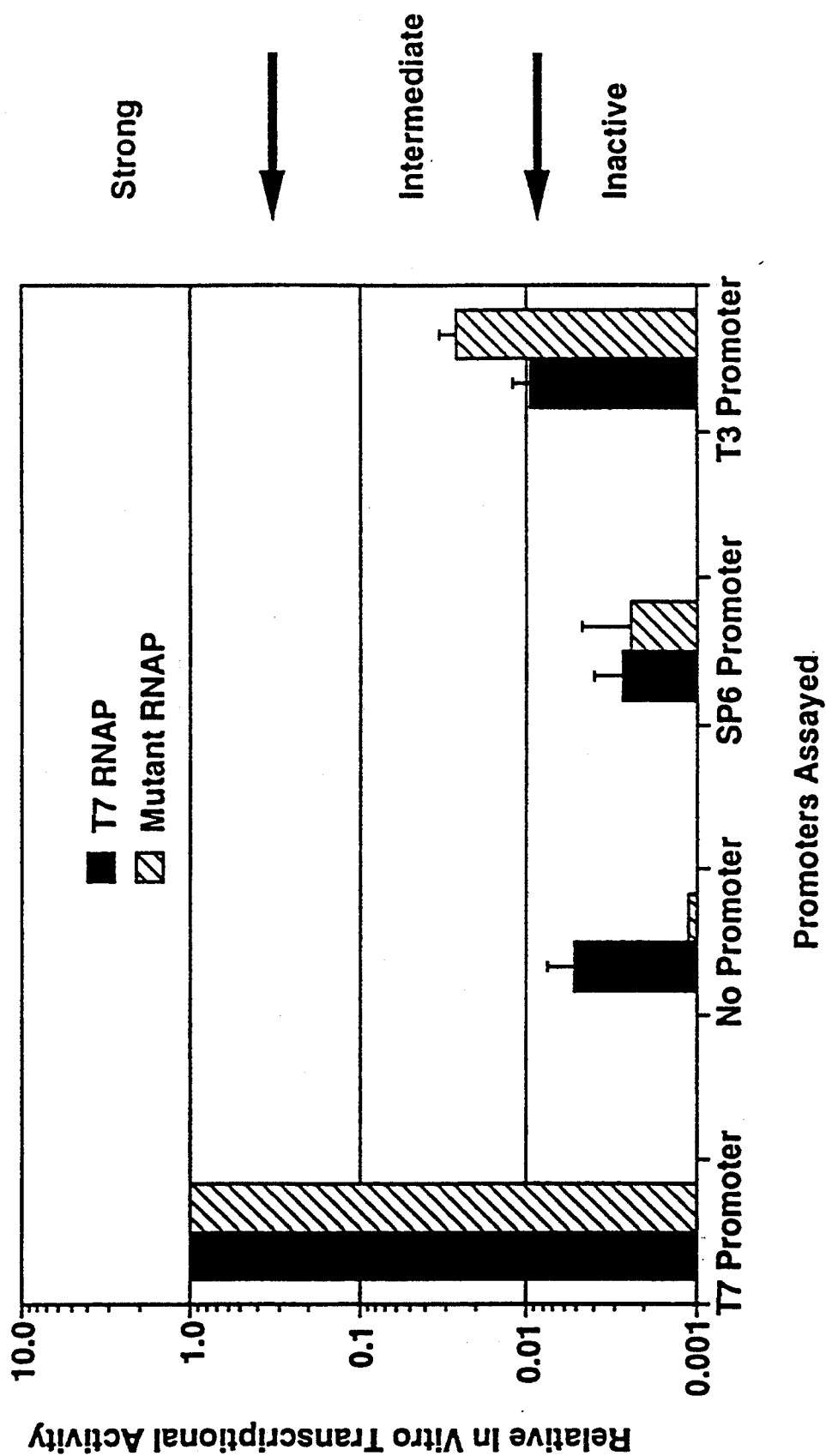

FIG. 6: Relative In Vitro Utilization of Bacteriophage SP6 and T3 Promoters by GP1(lys222) and Wild-type T7 RNA Polymerase. The promoters are listed on the horizontal axis, and relative activity is represented along the vertical axis. The Relative In Vitro Promoter Strength (or Promoter Strength) is defined in the section Methodology. The arrows on the right side of the graph indicate the approximate activities that differentiate the inactive, intermediate, and strong promoters. The results are the average of the two time points of at least three different samples, and the error associated with the measurements is the greater of the standard deviation observed. For clarity, only the top halves of the error bars are shown; however, the error bars should extend below the tops of the data columns for a distance equivalent to the value that the error bars extend above the data columns on logarithmic scale. No error bar is shown for use of the wild-type promoter by either wild-type T7 RNA polymerase of GP1(lys222) since the consensus T7 promoter has been defined to have a relative in vitro activity of 1.00. In these assays the concentration of T7 RNA polymerase was 80 nM while the concentration of GP1(lys222) was 40 nM. All other conditions were as previously described [(Ikeda, R. A., et al., *Biochemistry*, 31: 9073–9080 (1992)].

Figure 7:
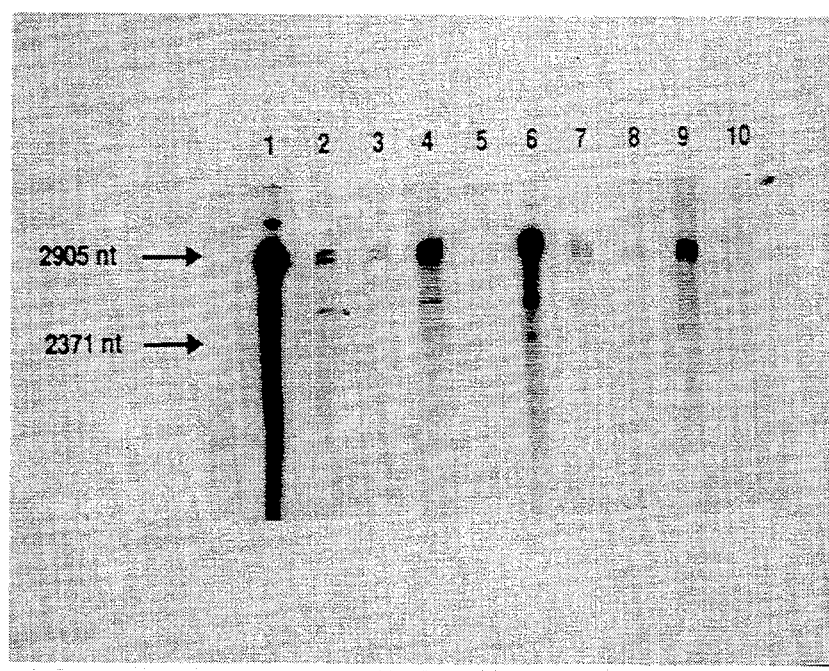

FIG. 7: Comparison of the Run-off Transcripts Synthesized by T7 RNA Polymerase and GP1(lys222). The autoradiograph of a denaturing 5% acrylamide gel shows that the run-off transcripts synthesized by T7 RNA polymerase and GP1(lys222) are identical in length. Lanes 1–5 show the run-off transcripts produced by 40 nM GP1(lys222) in the presence of pCAT10-1/NdeI (0.2 $\mu$l), pCM-P1198/NdeI (2.0 $\mu$l), pCM-T270/NdeI (10.0 $\mu$l), pCM-P1208/NdeI (10.0 $\mu$l), and pLM10/PvuII (10.0 $\mu$l), respectively, while lanes 6–10 show the run-off transcripts produced by 80 nM T7 RNA polymerase in the presence of pCAT10-1/NdeI (0.2 $\mu$l), pCM-1198/NdeI (2.0 $\mu$l), pCM-T270/NdeI (10.0 $\mu$l), pCM-P1208/NdeI (10.0 $\mu$l), and pLM10/PvuII (10.0 $\mu$l), respectively. All other conditions are described in the section Methodology. The volumes in parentheses following each template is the volume of each sample that was loaded on to the gel. Different volumes were loaded on to the gel to try to equalize the amount of run-off transcript in each lane. The transcripts synthesized in the presence of the pCM-X# templates are approximately 2900 nucleotides long while the barely perceptible transcripts synthesized in the presence of the pLM10 templates are approximately 2370 nucleotides long. The run-off doublets seen in lanes 1–4 and 6–9 are produced by a partially effective transcriptional terminator near the ends of the pCM-X# templates.

Figure 8:
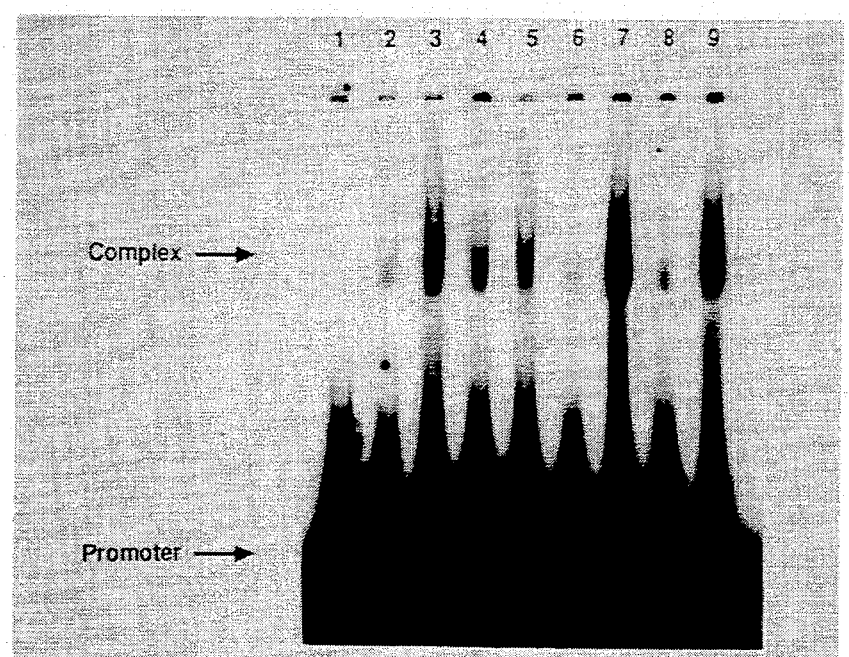

FIG. 8: Binding of a T7 Promoter by Wild-type T7 RNA Polymerase and GP1(lys222). The autoradiograph of a 5% acrylamide gel shows the binding of wild-type T7 RNA polymerase in lanes 6–9 and GP1(lys222) in lanes 2–5 to a $^{32}$P labeled oligonucleotide that carries a T7 promoter. Lane 1-no RNA polymerase, 5 $\mu$M promoter; Lane 2-26.5 nM GP1(lys222), 5 $\mu$M promoter; Lane 3-132.7 nM GP1(lys222), 5 $\mu$M promoter; Lane 4-26.5 nM GP1(lys222), 5 $\mu$M promoter, 3 $\mu$g lambda DNA; Lane 5-132.7 nM GP1(lys222), 5 $\mu$M promoter, 3 $\mu$g lambda DNA; Lane 6-12.9 nM T7 RNA polymerase, 5 $\mu$M promoter, Lane 7-64.7 nM T7 RNA polymerase, 5 $\mu$M promoter; Lane 8-12.9 nM T7 RNA polymerase, 5 $\mu$M promoter, 3 $\mu$g lambda DNA; Lane 9-64.7 nM T7 RNA polymerase, 5 $\mu$M promoter, 3 $\mu$g lambda DNA. Complex=Position of the enzyme/promoter complexes. Promoter=Position of the unbound promoter oligo.

UTILITY STATEMENT

The ability to produce the pKGP-HA1mut4 plasmid and to use the plasmid to produce the mutant T7 RNA polymerase GP1(lys222), which will recognize the T7 promoter carried on an inactive pCM-X# plasmid, to transcribe selectively a specific gene, namely the chloramphenicol acetyl transferase gene, can serve as the basis for altering characteristics of T7 RNA polymerase to give it unique properties, such as restoring chloramphenicol resistance to the *E. coli*. This invention discloses a mutant T7 RNA polymerase, and a means for selecting mutant T7 RNA polymerases, which will utilize inactive T7 promoter point mutants more effectively than wild-type T7 RNA polymerase both in vivo and in vitro.

DETAILED DESCRIPTION OF THE PREFERRED EMBODIMENT

To arrive at the mutant T7 RNA polymerase which recognizes the T7 promoter carried on an inactive pCM-X# plasmid, we devised and carried out the following process:

1. Randomly mutagenize pKGP1-1 plasmids with aqueous hydroxylamine to improve the possibility that a T7 gene 1 mutation would be responsible for the expression of the CAT gene cloned behind the inactive T7 promoter point mutant, and dialyzing the treated plasmids to remove the hydroxylamine.

2. Cotransform *E. coli* with the mutagenized plasmids and a mixture of seven different inactive pCM-X# plasmids and then subjecting the transformed *E. coli* cells to various antibiotics, including chloramphenicol, to isolate cells exhibiting chloramphenicol resistance. *E. coli* cells also were cotransformed with the mutagenized plasmids and pCAT10-1 to use as a comparison.

3. Select a representative pKGP1-1 plasmid, pKGP-HA1mut4, and cotransform *E. coli* with pKGP-HA1-mut4 and pCAT10-1, pKK232-8, or each of the seven different inactive pCM-X# plasmids separately to confirm that a T7 promoter-like sequence must be present on the CAT plasmid for expression of the CAT gene in the presence of pKGP-HA1 mut4.

4. Ligate restriction fragments from pKGP-HA1-mut4 into a wild type pKGP1-1 plasmid to confirm that the mutation responsible for altered promoter specificity is within T7 gene 1. The results suggested that the mutation was located in the amino half of the gene.

5. Ligate the various restriction fragments from the amino half of the pKGP-HA1mut4 plasmid to localize the promoter specificity mutation.

This process confirmed that the T7 gene 1 mutation responsible for altered promoter specificity was located on the 383 bp AlwNI/BstXI restriction fragment. Sequencing of the 383 bp region using an M13mp19 clone of the pKGP-HA1mut4 mutant gene 1 revealed that the only difference between the wild type T7 gene 1 and the mutant gene 1 was a G to A transition at position 664 of T7 gene 1, which changes glutamic acid (222) to lysine (222). The resulting mutant T7 RNA polymerase having the altered promoter specificity is GP1(lys222).

The selection of promoter recognition mutants of T7 RNA polymerase was pursued by randomly mutagenizing pKGP1-1 with aqueous hydroxylamine, cotransforming *E. coli* with the mutagenized pKGP1-1 and a mixture of the seven different inactive pCM-X# plasmids, and isolating and characterizing the RNA polymerase that was present in those colonies that exhibited chloramphenicol resistance. It was established that *E. coli* harboring the mutant plasmid pKGP-HA1mut4 and an inactive pCM-X# are chloramphenicol resistant and that the mutation responsible for the expression of CAT from the inactive pCM-X# plasmid is a G to A transition at nucleotide 664 of T7 gene 1 that converts glutamic acid(222) to lysine (FIGS. 3 and 4).

To determine if the observed growth of the cotransformed *E. coli* in the presence of chloramphenicol reflects the ability of the mutant T7 RNA polymerase to utilize the T7 promoter point mutants found on the pCM-X# plasmids, in vivo and in vitro promoter utilization were measured and compared (FIG. 5). In vivo promoter utilization was determined by measuring the relative abundance of CAT in extracts of *E. coli* that harbored pMutA/B (the variant of pKGP1-1 that carries a single G to A transition at nucleotide 664 of T7 gene 1) and a pCM-X# plasmid, while in vitro promoter utilization was determined by measuring RNA synthesis in the presence of purified RNA polymerase and purified template. Furthermore, the location of the initiation of transcription by GP1(lys222) and T7 RNA polymerase was confirmed by comparing the lengths of the run-off transcripts synthesized by the two enzymes in the presence of linearized pCM-X# and pLM10 templates. Although the absolute magnitudes of in vivo and in vitro promoter utilization differ, the in vivo and in vitro data show the same relative trends. The mutant T7 RNA polymerase, GP1(lys222), utilizes the seven inactive T7 promoter point mutants and three intermediate T7 promoter point mutants more efficiently than wild-type T7 RNA polymerase. The correlation of the in vivo and in vitro data and the observation that GP1(lys222) and T7 RNA polymerase initiate transcription at the same location and synthesize run-off transcripts of identical length suggest that the restoration of chloramphenicol resistance in the cotransformed *E. coli* results from the ability of GP1(lys222) to initiate transcription from T7 promoter point mutants that are normally inactive.

The observed changes in the promoter specificity of GP1(lys222) and the location and identity of the mutation in GP1(lys222) are notable. First, the Glu to Lys substitution at amino acid 222 of T7 RNA polymerase is located near the amino-terminal domain of the enzyme (amino acids 1 to 179) and alters promoter recognition by the mutant RNA polymerase. Similarly, it had been previously reported that a two amino acid insertion at position 222 disrupts DNA binding while preserving polymerase function [Gross et al., *J. Mol. Biol.*, 228: 488–505 (1993)]. Apparently, regions near the amino-terminal domain of T7 RNA polymerase are involved in promoter binding. Second, the Glu to Lys substitution allows GP1(lys222) to utilize all seven of the inactive T7 promoter point mutants. Since the inactive T7 promoter point mutations occur at four different positions in the T7 promoter it is unlikely that the single Glu to Lys substitution results in specific recognition of the seven inactive T7 promoter point mutants. In fact, the observation that GP1(lys222) uses intermediate T7 promoter point mutants more efficiently than wild-type T7 RNA polymerase suggests that the Glu to Lys substitution expands the specificity of the RNA polymerase. Conversely, the inability of GP1(lys222) to utilize an SP6 promoter (FIG. 6), the inability of GP1(lys222) to specifically initiate at a T3 promoter (FIG. 7), and the ability of GP1(lys222) to specifically utilize the inactive T7 promoter point mutant indicates that promoter specificity is not eliminated and that at a minimum GP1(lys222) requires the context of a T7-like promoter.

Mechanistically, the Glu(222) to Lys substitution could reduce the specificity of GP1(lys222) by at least two plausible mechanisms. First, the Lys substitution could cause a global structural change in the RNA polymerase that alters promoter binding, and second, the substitution of a positively charged amino acid side chain for a negatively charged amino acid side chain could stabilize the binding of the small negatively charged RNA initiation products within the transcription complex and increase the efficiency of utilization of a weak promoter. A third plausible mechanism seems, however, to be excluded by the observation that GP1(lys222) binds a T7 promoter less tightly than the wild-type T7 RNA polymerase (FIG. 8). This observation suggests that it is unlikely that the positively charged lysine side chain stabilizes the binding of the RNA polymerase to the negatively charged DNA template and improves the ability of the mutant enzyme to recognize promoter-like sequences.

Mutant T7 RNA polymerases that exhibit altered promoter specificity can be isolated by screening for chloramphenicol resistance in *E. coli* harboring a plasmid that expresses T7 RNA polymerase (pKGP1-1) and a promoter selection vector that carries an inactive T7 promoter point mutant (an inactive pCM-X#). The mutation responsible for the altered promoter specificity of the mutant T7 RNA polymerase can be easily identified, and the effect of the mutation on promoter recognition can be measured. By isolating and characterizing mutations that alter promoter recognition by T7 RNA polymerase it should be possible to identify the regions of the RNA polymerase that can contribute to promoter recognition.

The following methodology provides additional details of the polymerase and processes of this invention. This methodology is not intended to restrict the invention to the methodology and uses described therein. In these examples, the following materials and methodology were used throughout:

1. Cell Strains. *E. coli* DH5 and DH5αF' were obtained from Gibco/BRL, *E. coli* JM101 was obtained from Stratagene, and *E. coli* BL21 was obtained from Novagen.

2. Chemicals. Acrylamide, agarose, ammonium persulfate, buffers, dithiothreitol, N,N,N',N'-tetramethylethylenediamine, N,N'-methylene-bis-acrylamide, and urea were electrophoresis grade. IPTG was molecular biology grade. Media was from Difco. Antibiotics were from Sigma. DTNB and CENTA β-Lactamase Substrate were from Calbiochem. Hydroxylamine was from Sigma. All other chemicals were reagent grade.

3. Enzymes. Restriction endonucleases, Klenow fragment of *E. coli* DNA polymerase I were from New England Biolabs. Calf intestine alkaline phosphatase, Sequenase Version 2.0, T4 polynucleotide kinase, and T4 ligase were purchased from United States Biochemical.

4. Purification. T7 RNA polymerase was purified by standard methods [Ikeda, R. A. et al., *J. Biol. Chem.*, 267: 11322–11328 (1992)], and the mutant T7 RNA polymerase was purified by standard methods [Tabor, S. and Richardson, C. C., *Proc. Natl. Acad. Sci. USA*, 82: 1074–1078 (1985); Ikeda, R. A. and Richardson, C. C., *J. Biol. Chem.*, 262: 3790–3799 (1987)] from *E. coli* BL21 harboring plasmids pMutA/B and pAGR-3R. The T7 RNA polymerase was greater than 98% pure and was estimated to have a specific activity of 43,700 u/mg, while the mutant T7 RNA polymerase was greater than 95% pure and was estimated to have a specific activity of 14,800 u/mg [Chamberlin, M., et al., *Nature*, 228: 227–231 (1970)].

5. Media. LB media consists of 10.0 g of tryptone, 5.0 g of yeast extract, and 10.0 g of NaCl per liter of media; the pH of the media was adjusted to 7.5 with NaOH. SOC media consists of 20 g/l tryptone, 5.0 g/l yeast extract, 0.6 g/l NaCl, 0.5 g/l KCl, 10 mM $MgCl_2$, 10 mM $MgSO_4$, and 20 mM glucose; the pH of the media was adjusted to 7.5 with NaOH.

6. Nucleoside 5'-triphosphates. [2,8-$^3$H]-ATP (25–40 Ci/mmol), [α-$^{35}$S]-dATP (1000–1500 Ci/mmol), [α-$^{32}$P]-UTP (800 Ci/mmol), and [γ-$^{32}$P]-ATP (3000 Ci/mmol) were purchased from Dupont/New England Nuclear Research Products. Ribonucleoside triphosphates were obtained from Pharmacia/LKB. dNTPs and ddNTPs were from United States Biochemicals.

7. Oligodeoxyribonucleotides. Complementary 24 base pair oligonucleotides containing the T7 promoter (5'dATTAATACGACTCACTATAGGACT3' and 3'TAATTATGCTGAGTGATATCCTGA5') were purchased from Genosys Biotechnologies, Inc. M13 Sequencing Primer (−40) was purchased from New England Biolabs. Sequencing primers TEMP −34 (5'dATA GGT ACG ATT TAC3'), 171 (5'dTCA ACT TAA AGC TGG3'), 298 (5'dCCG ACA GCC TTC CAG TTC CTA3'), 365 (5'dCTC TGG CTT CGG TAA3'), and 563 (5'dCTG ACA TGC TCT CTA3') were purchased from Genosys Biotechnologies, Inc. The names of the primers indicate the location with respect to T7 gene 1 (in base pairs) that the primers will anneal. Since ligation of the pKGP-HA1mut4 EcoRI/PstI fragment into the EcoRI and PstI sites of M13mp19 inserts the mutant T7 gene 1 into M13mp19 in counter clockwise direction, the noncoding (with respect to translation) strand of T7 gene 1 is the template for sequencing.

8. Plasmids. Plasmid pKK232-8 was obtained from Pharmacia. The plasmid pKGP1-1 (an expression clone of T7 gene 1) (FIG. 2), the plasmid pCAT10-1 (a selection plasmid carrying the CAT gene cloned under the control of a wild-type T7 promoter), the plasmids pCM-T270, pCM-T286, pCM-T297, pCM-P1031, pCM-P1087, pCM-P1160, and pCM-P1208 (the plasmids carrying CAT genes cloned under the control of T7 promoter point mutants that are normally inactive in the presence of T7 RNA polymerase), and the plasmids pCM-P1198, pCM-B64, and pCM-T221 (the plasmids carrying CAT genes under the control of T7 promoter point mutants with moderate activity) have been previously described [Ikeda, R. A., et al., *Biochemistry*, 31: 9073–9080 (1992); Ikeda, R. A., et al., *Nucl. Acids Res.*, 20: 2517–2524 (1992)] (Table I). Plasmid pSP64, a plasmid carrying an SP6 promoter, was obtained from Promega; plasmid pLM10, a pBR derivative carrying a T3 promoter, was a gift from Dr. William McAllister, State University of New York, Brooklyn; and plasmid pAGR3R, a plasmid carrying the lac i gene, was a gift from Dr. William Jack, New England Biolabs. All plasmids were prepared by standard methods [Sambrook, J., et al., *Molecular Cloning: A Laboratory Manual*, 2ed (1989)]. The identities of the plasmids were confirmed by restriction mapping [Sambrook, J., et al., *Molecular Cloning: A Laboratory Manual*, 2ed (1989)] and by phenotypic analysis, in vivo [Ikeda, R. A., et al., *Biochemistry*, 31: 9073–9080 (1992); Ikeda, R. A., et al., *Nucl.*

*Acids Res.*, 20: 2517-2524 (1992)]. Electrophoretic analysis of the purified plasmids showed that the DNA was at least 95% supercoiled DNA. Little or no linear and/or open circular forms could be detected. For the hydroxylamine mutations and the in vitro RNA polymerase assays, the plasmids were used in their natural state at natural superhelical densities. For examination of run-off transcripts, the plasmids pCAT10-1, pCM-P1198, pCM-T270, and pCM-P1208 were cleaved with NdeI, while the plasmid pLM10 was cleaved with PvuII. Complete cleavage of these plasmids was confirmed by analytical electrophoresis, and the cleaved DNA was purified by phenol extraction and ethanol precipitation. The precipitated DNAs were then redissolved in buffer containing 10 mM Tris-HCl, pH 7.8, and 1 mM EDTA.

METHODOLOGY

1. Mutagenesis of pKGP1-1 with Hydroxylamine. Mutagenesis of pKGP1-1 was performed in a 500 $\mu$l reaction containing 17-25 $\mu$g of pKGP1-1, 0.8M hydroxylamine, and 0.1M potassium phosphate buffer, pH 6.0. The reaction was incubated at 70° C., and at 15, 30, 45, 60, and 75 min 100 $\mu$l samples were removed from the reaction and placed on ice. The samples were then dialyzed extensively against 75 mM $CaCl_2$ at 4° C., and stored at $-20°$ C.

2. Screening for Mutant T7 RNA Polymerases with Altered Promoter Specificity. Competent *E. coli* JM101, 200 $\mu$l, were cotransformed with 4 $\mu$l of the hydroxylamine treated pKGP1-1 (approx. 40 ng) and either 4 $\mu$l of a mixture of all of the inactive pCM-X# plasmids where the concentration of each individual inactive pCM-X# is 4 ng/4 $\mu$l or 40 ng of pCAT10-1. SOC, 0.9 ml, was added to the cells, and the culture was grown at 37° C. for one hour. LB, 1.1 ml, containing 100 $\mu$g/ml amp, 100 $\mu$g/ml kan and 60 $\mu$g/ml cam was then added to the SOC culture, and the cells were grown at 37° C. for an additional 4 hrs. Subsequently, equal volumes of the transformation, 200 $\mu$l, were spread on three different types of LB-agar plates containing either (1) 50 $\mu$g/ml kan and 50 $\mu$g/ml amp, (2) 50 $\mu$g/ml kan, 50 $\mu$g/ml amp, and 30 $\mu$g/ml cam, or (3) 50 $\mu$g/ml kan, 50 $\mu$g/ml amp, and 1.0 mM IPTG. The plates were incubated at 37° C. for 16 hrs, and the number of colonies on each plate was counted if any were present. The *E. coli* JM101 must be positively lac iQ. The absence of a good lac iQ phenotype produces misleading results.

3. Isolation of pKGP1-1 Plasmids Carrying Potential Mutants of T7 RNA Polymerase. Colonies that grew on the kan/amp/cam plates were transferred to 4.0 ml of LB containing 50 $\mu$g/ml kan, 50 $\mu$g/ml amp, and 30 $\mu$g/ml cam and were grown overnight at 37° C. The plasmid DNA was isolated from the overnight cultures and the presence of pKGP1-1 and a pCM-X# plasmid was confirmed by restriction analysis (EcoRI plus PstI, data not shown).

To separate the pKGP1-1 plasmid from the pCM-X# plasmid, the DNA isolated from a cam resistant colony was either run on a low melting agarose gel and the band corresponding to pKGP1-1 was isolated from the gel and used to transform *E. coli* JM101, or the DNA from the resistant colony was digested with PvuII for 5 hours at 37° C. (pKGP1-1 contains no PvuII sites, and the pCM-X# plasmids contains 3 PvuII sites; complete digestion of the pCM-X# plasmid was confirmed by gel analysis), and 3 $\mu$l of the digest was used to transform *E. coli* JM101. In either case the transformed cells were then plated on LB-agar plates containing (1) 50 $\mu$g/ml kan, (2) 50 $\mu$g/ml kan and 50 $\mu$g/ml amp, and (3) 50 $\mu$g/ml amp. The absence of colonies on the kan/amp and amp plates was used to confirm the removal of the pCM-X# plasmids. Colonies from the kan plates were then grown overnight in 4.0 ml of LB containing 50 $\mu$g/ml kan, and the plasmid DNA was isolated; the identity and purity of the isolated pKGP1-1 plasmid was confirmed by restriction analysis (EcoRI plus PstI).

To determine the promoter specificity of the T7 RNA polymerase mutants, *E. coli* JM101 was cotransformed with 2 $\mu$l of the isolated pKGP1-1 DNA and each of the following plasmids: 20-50 ng of each of the inactive pCM-X# plasmids separately, 40 ng of pCAT10-1, and 40 ng of pKK232-8. SOC, 0.9 ml was added to the cells, and the culture was grown at 37° C. for one hour. Equal volumes of the transformations, 200 $\mu$l, were spread on three different types of LB-agar plates containing either (1) 50 $\mu$g/ml kan and 50 $\mu$g/ml amp, (2) 50 $\mu$g/ml kan, 50 $\mu$g/ml amp, and 30 $\mu$g/ml cam., or (3) 50 $\mu$g/ml kan, 50 $\mu$g/ml amp, and 1.0 mM IPTG. The plates were incubated at 37° C. for 16 hrs, and the number of colonies on each plate was counted.

4. Identification of the T7 RNA Polymerase Mutation Responsible for Altered Promoter Specificity. Approximately 100 $\mu$g of the mutant pKGP1-1 were isolated for cloning. The mutant pKGP1-1 was cut with either (1) EcoRI and HpaI, HpaI and PstI; (2) EcoRI and FspI, HpaI and FspI; or (3) EcoRI and BstXI, BstXI and FspI, and the restriction fragments containing the pieces of the potentially mutant T7 gene 1 were isolated on a low melting agarose gel. These "mutant" fragments were then cloned into the corresponding sites of a wild type pKGP1-1 plasmid (FIG. 3). This generated the clones pMutE/H and H/P; pMutE/F and F/P; pMutE/B and B/F. *E. coli* JM101 was then cotransformed with each clone and either a mixture of all seven inactive pCM-X# plasmids or pCM-P1031. The cells were then spread on LB-agar plates containing (1) 50 $\mu$g/ml kan and 50 $\mu$g/ml amp, (2) 50 $\mu$g/ml kan, 50 $\mu$g/ml amp, and 30 $\mu$g/ml cam, or (3) 50 $\mu$g/ml kan, 50 $\mu$g/ml amp, and 1.0 mM IPTG. The plates were incubated at 37° C. for 16 hrs, and the number of colonies on each plate was counted to determine which restriction fragment confers the altered promoter specificity.

A final pair of clones was generated by cleaving wild type pKGP1-1 and the pMutE/B clone with AlwNI, and ligating a wild type restriction fragment to a pMutE/B restriction fragment. The resulting pMutE/A and pMutA/B clones were then used to transform *E. coli* JM101, and the transformed cells were screened as outlined in the preceding paragraph.

To determine the identity of the mutation responsible for the altered promoter specificity of the mutant T7 RNA polymerase, the sequence of the region conferring the mutant phenotype was determined. To facilitate sequencing, the mutant pKGP-HA1 mut4 plasmid was cut with EcoRI and PstI, and the restriction fragment containing T7 gene 1 was ligated into the EcoRI and PstI sites of M13mp19. The clone was confirmed by restriction mapping (data not shown). The mutant region was then sequenced via the protocols recommended by United States Biochemicals using Sequenase Version 2.0 and the sequencing primers TEMP $-34$, 171, 298, 365, 565, and the New England Biolabs M13 Sequencing Primer ($-40$).

5. Preparation of Cell Extracts. Extracts of *E. coli* JM101 harboring either pKGP1-1 and pCM-X# or mutant pKGP1-1 and pCM-X# were prepared [Ikeda, R. A., et al., *Biochemistry*, 31: 9073-9080 (1992)]. Extracts were always prepared immediately prior to use.

6. Measurement of Chloramphenicol Acetyl Transferase Activity. CAT activity can be measured spectrophotometrically by monitoring the increase in $A_{412}$ caused by the accumulation of 5-thio-2-nitrobenzoic acid produced from the reaction of CoA with DTNB [Brosius, J. and Lupski, J. R., *Methods in Enzymology*, 153: 54-68 (1987); Shaw, W. V., *Methods in Enzymology*, 43: 737-775 (1975); and Ikeda, R. A., et al. *Biochemistry*, 31: 9073-9080 (1992)]. One unit of CAT activity is defined as the amount of enzyme necessary to acetylate one nanomole of cam per min.

7. Measurement of β-Lactamase Activity. Bla activity can be measured spectrophotometrically by monitoring the increase in $A_{415}$ caused by the accumulation of CENTA hydrolysis products. [Jones, R. N., et al., *J. Clin. Microbial*, 15: 954-958 (1982); Ikeda, R. A., et al., *Biochemistry*, 31: 9073-9080 (1992)]. One unit of bla activity is defined as the amount of enzyme necessary to hydrolyze one nanomole of CENTA per min.

8. Determination of Relative Promoter Strength In Vivo. To determine relative promoter strength in vivo, the specific CAT activity of a sample was first divided by its specific bla activity to give a relative abundance ratio. The relative abundance ratio was then normalized by division by the relative abundance ratio measured for extracts made from *E. coli* containing a selection plasmid carrying a wild type T7 promoter (pCAT10-1). This defines the relative, in vivo, strength of a wild type T7 promoter as 1.0; therefore, promoters that direct the synthesis of reduced quantities of CAT will have relative strengths less than 1.0 [Ikeda, R. A., et al., *Biochemistry*, 31: 9073-9080 (1992)].

9. Measurement of the Specific Activities of the T7 RNA Polymerases. The specific activities of GP1(lys222) and T7 RNA polymerase were determined by measuring the mount of [2,8-$^3$H]-ATP that is incorporated into DE81 retainable RNA during a 10 min incubation at 37° C. in 50 μl transcription reactions containing 50 mM Tris-HCl, pH 8, 10 mM MgCl$_2$, 1.5 μg T7 DNA, 400 μM of each of the four rNTPs, 2,8-$^3$H]-ATP (66.0 cpm/pmol), 1 mM DTT, 30 μg/ml BSA, and 0.150 or 0.030 μg of RNA polymerase [Ikeda, R. A., and Richardson, C. C., *J. Biol. Chem.*, 262: 3790-3799 (1987)]. One unit of activity is equal to the incorporation of 1 nmole of ATP into RNA in 1 hour [Chamberlin, M., et al., *Nature*, 228: 227-231 (1970)].

In addition the specific activities of GP1(lys222) and T7 RNA polymerase were also determined under other non-standard conditions to provide a direct comparison of the two polymerases activities in different assays. As noted in the text, different DNAs were used (1.5 μg of pCAT10-1 or 1.5 μg of pCAT10-1/NdeI) and different buffer conditions were used (50 mM tris-HCl, pH 8, 10 mM MgCl$_2$, 60 mM NaCl, and 2.5 mM spermidine).

10. Measurement of Promoter Strength In Vitro. Promoter strength in vitro can be determined by measuring the production of RNA from a supercoiled plasmid containing a mutant T7 promoter (pCM-X#) in comparison to the production of RNA from a supercoiled plasmid containing a consensus T7 promoter (pCAT10-1). [Chapman, K. A., et al., *Nucl. Acids Res.*, 16: 4511-4524 (1988); Chapman, K. A., and Burgess, R. R., *Nucl. Acids Res.*, 15: 5413-5432 (1987)]. The relative strength of a promoter on a pCM-X# clone was determined by dividing the amount of RNA synthesized in a reaction containing the pCM-X# clone by the amount of RNA synthesized in a reaction containing pCAT10-1 consensus clone. This procedure defines the activity of pCAT10-1 to be 1.00 [Ikeda, R. A., et al., *Biochemistry*, 31: 9073-9080 (1992)].

11. Confirmation of the Site of Initiation of Transcription. To confirm that GP1(lys222) specifically initiates transcription at the T7 promoter carried on the various pCM-X# plasmids, run-off transcripts were examined. Run-off transcripts were produced in 60 μl reactions containing 50 mM Tris-HCl, pH 7.8, 60 mM NaCl, 2.5 mM spermidine, 10 mM MgCl$_2$, 1 mM dithiothreitol, 125 μM UTP, 400 μM of each of the other three rNTPs, 15 μCi [α-$^{32}$P]-UTP, 30 μg/ml bovine serum albumin, 8 nM promoter/plasmid (Either pCAT10-1/NdeI, pCM-P1198/NdeI, pCM-T270/NdeI, pCM-P1208/NdeI or pLM10/PvuII), and 80 nM T7 RNA polymerase or 40 nM GP1(lys222). The reactions were equilibrated at 37° C., and RNA synthesis was initiated by addition of T7 RNA polymerase. At 60 min the reactions were stopped by the addition of an equal volume of loading buffer (90% formamide, 10 mM Tris-HCl, pH 7.8, 0.1% xylene cyanol, 0.1% bromophenol blue). The samples were heated to 90° C. for 2 min, cooled on ice, and loaded on a 5% acrylamide (30 to 1 acrylamide to bisacrylamide), 50% urea, denaturing gel. The samples were then electrophoresed for 18 hours at 250 V. After electrophoresis the gel was fixed by soaking in an aqueous solution containing 10% methanol and 10% acetic acid. The gel was then dried and visualized by autoradiography.

12. Estimation of Promoter Binding. The ability of T7 RNA polymerase and GP1(lys222) to bind a T7 promoter was determined by a gel-retardation method [Muller, D. K., et al., *Biochemistry*, 27: 5763-5771 (1988)]. The promoter containing oligonucleotide was identical to the one used by Muller et al., but the 25 μl binding reactions contained 10 mM potassium phosphate, pH 7.8, 1 mM EDTA, 20 mM NaCl, 10% glycerol, 5 μM promoter (approx. $3.9 \times 10^7$ cpm) or 2 μM promoter ($1.57 \times 10^7$ cpm), T7 RNA polymerase or GP1(lys222), and in some cases a nonspecific competitor DNA (3 μg of lambda DNA). After a 10 min incubation at 25° C., the samples were loaded onto a pre-electrophoresed 5% acrylamide gel (30 to 1 acrylamide to bisacrylamide) and electrophoresed for 50 min at 12 watts in 45 mM Tris-Borate and 1 mM EDTA. The gel was then fixed by soaking in an aqueous solution of 10% methanol and 10% acetic acid, dried, and visualized by autoradiography. The promoter/polymerase complexes were then cut out of the gel, and the amount of promoter contained in the complexes was measured by liquid scintillation.

SELECTION AND CHARACTERIZATION OF MUTANT T7 RNA POLYMERASE GP1(LYS222)

The methodology described above was carried out to select and characterize a mutant T7 RNA polymerase to reinstate chloramphenicol resistance to *E. coli*. Referring to the appended Figs., the results of carrying out the methodology described above to select and characterize the pKGP-HA1mut4 plasmid to be paired with an inactive pCM-X# plasmid, resulting in chloramphenicol resistance in *E. coli*, are detailed below.

1. Construction of the Promoter Assay Plasmids

A 50 nucleotide, double stranded, DNA fragment containing a wild type T7 Class III promoter or a mutated T7 promoter was synthesized by a combination of chemical and enzymatic methods [Schneider, T. D. and Stormo, G. D., *Nucl. Acids Res.*, 17: 659–674 (1989)]. The primer oligo was annealed to each of the six oligodeoxyribonucleotides, WT, B, T, P, C, and G (Table IV). Large fragment of *E. coli* DNA polymerase I and dNTP's were used to extend the primer and synthesize the DNA strand complementary to the oligonucleotides WT, B, T, P, C and G. The double stranded 50 nucleotide DNA fragments were then cleaved with HindIII and ligated between the HindIII and SmaI restriction sites of pKK232-8. (When the B oligonucleotide was cleaved with HindIII and ligated into pKK232-8 it appears that a single A was lost from the 3' end of the oligonucleotide in most of the pCM-B# clones. This A deletion does not affect the sequence of the promoter and does not affect the behavior of the clones.). The ligation mixtures were transformed into competent *E. coli* DH5, and the transformations were grown on LB plates containing 50 μg/ml ampicillin.

Figure 1:
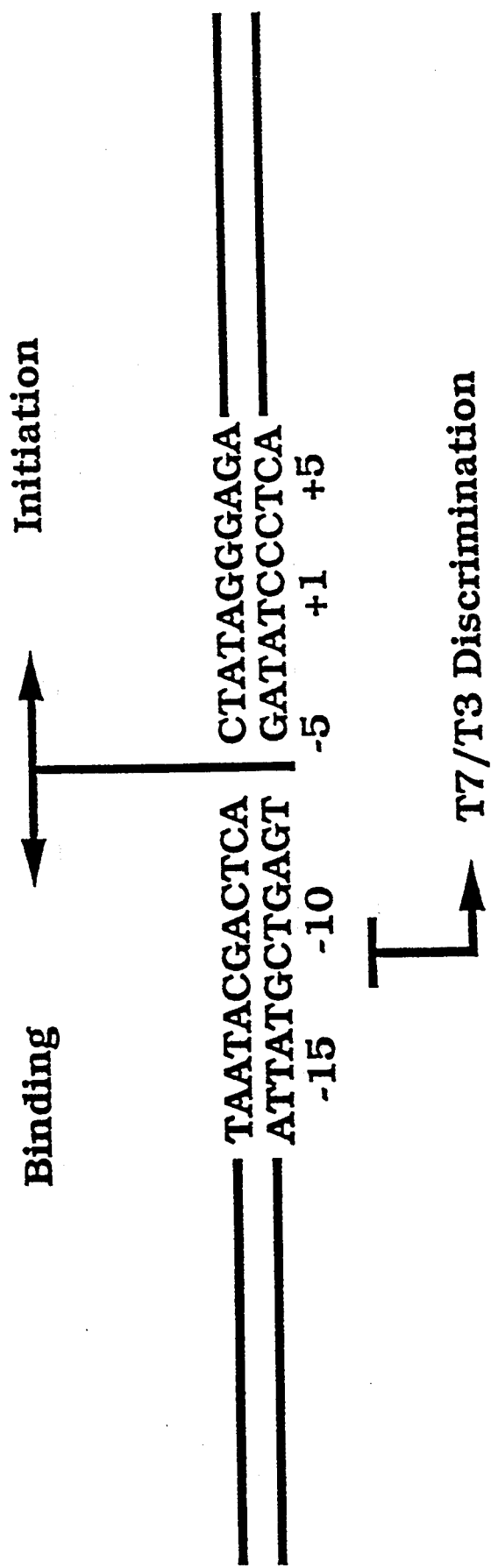
FIG. 1: The Consensus T7 Promoter. The base pairs at −9, −10 and −11 have been implicated in the ability of T7 RNA polymerase to distinguish T7 and T3 promoters.
Figure 2:
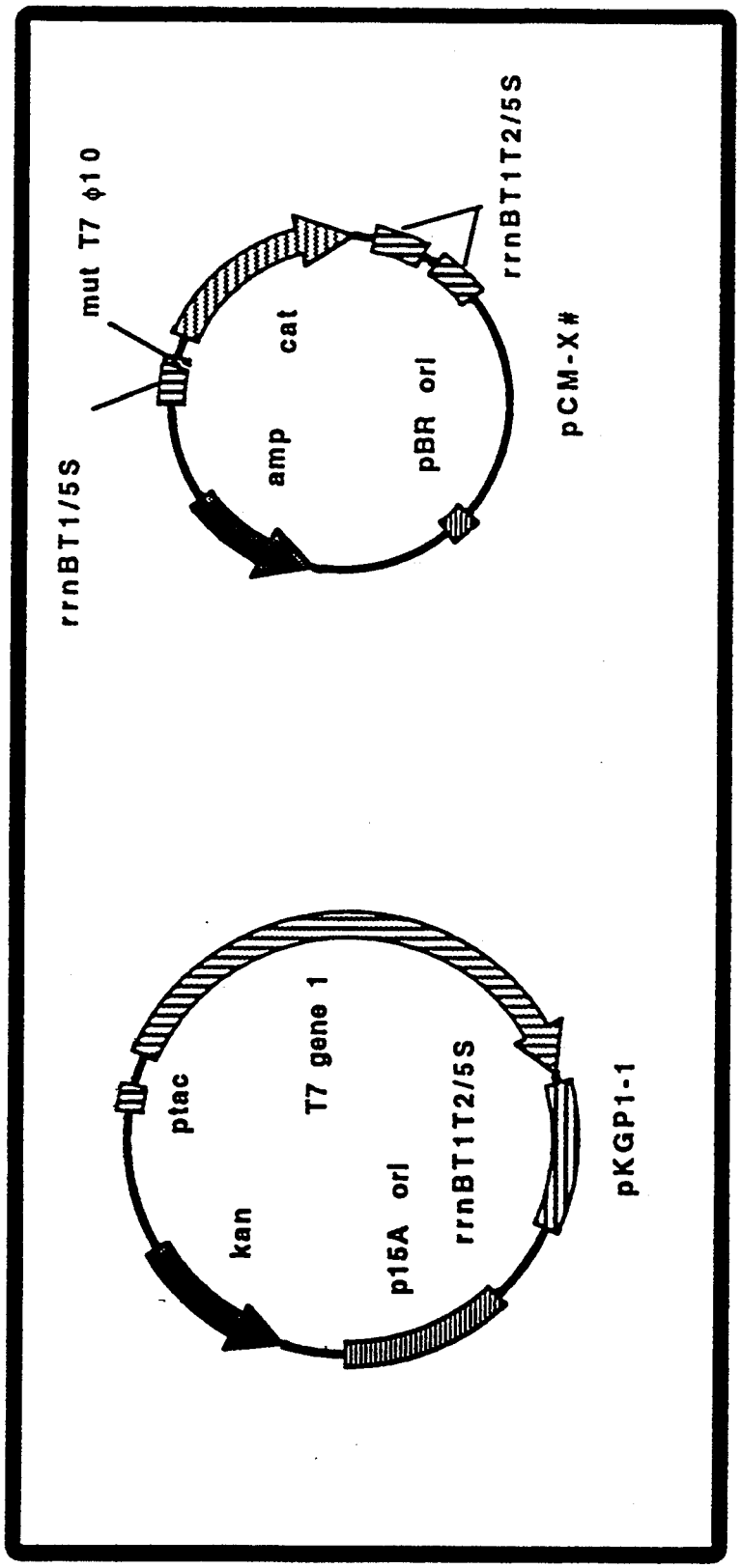
FIG. 2: Plasmids pKGP1-1 and pCM-X#. A schematic representation of the two plasmid selection system. Abbreviations: kan, kanamycin resistance gene; amp, ampicillin resistance gene; cat, chloramphenicol resistance gene; p15A ori, p15A origin of replication.

For the WT oligo, ten independent colonies were chosen, and plasmid DNA was isolated from overnight cultures grown at 37° C. in 4 ml of LB containing 50 μg/ml ampicilin. Insertion of the T7 φ10 promoter into pKK232-8 was confirmed by AseI restriction maps of the plasmids. The cloning places a wild type T7 φ10 promoter just upstream of the promoterless chloramphenicol acetyl transferase gene of pKK232-8. This new plasmid is designated pCAT10-1 (FIG. 2).

For the B, T, P, C, and G oligodeoxyribonucleotides, 400, 350, 329, 10, and 10 independent colonies, respectively, were chosen from the transformations. Plasmid DNA was isolated from each transformant from overnight cultures grown at 37° C. in 4 ml of LB containing 50 μg/ml ampicillin. Insertion of oligo B into pKK232-8 was confirmed by HindIII and PstI restriction maps of the plasmids. Insertion of oligo T was confirmed by ScaI restriction maps, and insertion of oligos P, C, and G were confirmed by ScaI or AseI restriction maps. This restriction mapping identified 252 B clones, 138 T clones, 121 P clones, 8 C clones, and 8 G clones with apparent insertions of the respective oligodeoxyribonucleotides. These clones are designated pCM-B#, pCM-T#, pCM-P#, pCM-C#, and pCM-G#, respectively (FIG. 2), where # is the general designation for the number assigned to the isolated clone. In this specification the entire family of clones is referred to as pCM-X#, where X refers to the B, T, P, C, and G clones, collectively.

2. Construction of pKGP1-1

To screen the promoter assay plasmids for in vivo T7 promoter activity it is necessary to express T7 RNA polymerase in the cell strain used for screening. For this purpose we chose to construct a p15A origin plasmid that expresses T7 RNA polymerase from the tac promoter.

Plasmid pGP1-5 (2.0μg) [Tabor, S. and Richardson, C. C., *Proc. Natl. Acad. Sci USA*, 82: 1074–1078 (1985)] was linearized by cleavage with BglII, and the linearized plasmid DNA was incubated at 37° C. with 0.3 units of Bal31 to delete the lambda $P_L$ promoter from the DNA. Samples (0.4 μg) were removed from the reaction after 5, 10, 20, and 40 minutes of incubation, and the ends of the Bal31-treated DNA were repaired with large fragment of *E. coli* DNA polymerase I in the presence of excess dNTP's. BamHI linkers were ligated to the DNA samples, the ligation mixtures were recut with BamHI, and the BamHI digested DNA was analyzed by gel electrophoresis on a 1% low melting point agarose gel. The 2.8 kilobase fragments from the 10 and 20 min. samples were cut out of the gel, and the fragments were isolated on an Elutip-d column. These 2.8 g kilobase BamHI fragments that contain T7 gene 1 were ligated into the BamHI site of pUC19, and competent *E. coli* DH5α were transformed with the two ligation reactions. The transformations were grown on LB plates containing 50 μg/ml ampicillin, 20 μg/ml X-gal, and 0.5 mM IPTG. Ten white colonies from each of the two ligations were picked for further analysis. Plasmid DNA was isolated from 4.0 ml overnight cultures (37° C. and 50 μg/ml ampicillin in LB) of each of the twenty colonies, and the lengths of the DNA fragments inserted into the pUC vector were analyzed by restriction mapping with AccI, EcoRI, BamHI, BamHI & ScaI, EcoRI, HindIII, and AccI & KpnI. One clone contained an insert with 337 bases removed from the BglII end of the BglII/BamHI fragment of pGP1-5. This clone was designated pGP1-20B, and was chosen for further manipulation.

The 2.5 kilobase EcoRI/HindIII fragment from pGP1-20B was isolated on a 1% low melting point agarose gel and ligated into the EcoRI/HindIII site of plasmid pKK223-3. This places T7 gene 1 immediately downstream of the tac promoter of plasmid pKK223-3. This plasmid was designated pKK-gp1.

Plasmid pKK-gp 1 was cut with NaeI, and BglII linkers were ligated onto the NaeI cleavage sites. The ligation mix was recut with BglII and BglI, and the 4362 base pair BglI/BglII(NaeI) fragment from pKK-gp1 was ligated to the 2892 base pair BamHi/BglI fragment of pACYC177 [Chang, A. C. Y. and Cohen, S. N., *J. Bacteriol.*, 134: 1141–1156 (1978); Rose, R. E., *Nucl. Acids Res.*, 16: 356 (1988)]. This ligates the tac promoter-T7 gene 1 fusion to the p15A origin of pACYC177 and generates a plasmid that also expresses both ampicillin and kanamycin resistance. To inactivate the ampicillin resistance gene, the p15A/gene 1 plasmid was recut with BglI and ScaI, repaired with T4 DNA polymerase and excess dNTP's, and recircularized with T4 DNA ligase. This deletes 360 bases from the middle of the ampicillin resistance gene and produces plasmid pKGP1-1 (FIG. 2). In *E. coli* JM101 plasmid pKGP1-1 efficiently produces active T7 RNA polymerase in the presence of IPTG.

3. Mutagenesis of pKGP1-1 and Selection of Possible Mutants of T7 Gene 1

To improve the possibility that a T7 gene 1 mutation would be responsible for the expression of the CAT gene cloned behind the inactive T7 promoter point mutant, pKGP1-1 was exposed to aqueous hydroxylamine at 70° C. for 15, 30, 45, 60 and 75 min. The treated plasmid samples were then dialyzed to remove the hydroxylamine, and *E. coli* JM101 was transformed with the treated pKGP1-1 and either a mixture of the seven inactive pCM-X# plasmids or pCAT10-1 (Table 1 and FIG. 2). After the transformed cells were allowed to recover in liquid culture in the absence of antibiotics, amp, kan, and cam were added to the liquid media, and the entire culture was incubated for 4 hrs at 37° C. This step amplifies the abundance of those mutants that are cam resistant, and simplifies the isolation of mutants that might occur very infrequently. The transformed cells were then plated on LB-agar containing either (1) 50 μg/ml kan and 50 μg/ml amp (kan/amp), or (2) 50 μg/ml kan, 50 μg/ml amp, and 30 μg/ml cam (kan/amp/cam). It was observed that the pKGP1-1 sample that had been incubated with hydroxylamine for 60 min yielded approximately 200 colonies on the kan/amp and kan/amp/cam plates when cotransformed with pCAT10-1, and 100 colonies on the kan/amp plate and 26 colonies on the kan/amp/cam plate when cotransformed with the mixture of the seven different pCM-X# plasmids that carry the seven inactive T7 promoter point mutants. This suggested that the CAT gene on at least one of the pCM-X# plasmids was expressed in the presence of the hydroxylamine treated pKGP1-1. Due to the early imposition of cam selection the 26 mutant colonies do not reflect the frequency of mutation.

To confirm that the cam resistance observed with *E. coli* harboring inactive pCM-X# plasmids required the presence of a hydroxylamine treated pKGP1-1 plasmid, mutant pKGP1-1 plasmid DNA was isolated from the 26 colonies that grew on the kan/amp/cam plate, and fresh *E. coli* JM101 was cotransformed with the mixture of the seven inactive pCM-X# plasmids and each of the different mutant pKGP1-1 plasmids. All of the isolated mutant pKGP1-1 plasmids allowed *E. coli* to grow on kan/amp/cam plates in the presence of the mixture of inactive pCM-X# plasmids. Since the 26 isolates behaved identically in this assay, one representative isolate (pKGP-HA1mut4) was chosen for further characterization.

*E. coli* JM101 was cotransformed with pKGP-HA1mut4 and pCAT10-1, pKK232-8, or each of the seven different inactive pCM-X# plasmids separately. As shown in Table 2, all seven inactive pCM-X# plasmids and pCAT10-1 allowed *E. coli* to grow on kan/amp/cam plates in the presence of pKGP-HA1mut4, while *E. coli* harboring pKK232-8 and pKGP-HA1mut4 were not resistant to chloramphenicol. This demonstrated that a T7 promoter-like sequence must be present on the CAT plasmid for expression of the CAT gene in the presence of pKGP-HA1mut4.

4. Identification of a Mutation that Alters the Specificity of T7 RNA Polymerase To demonstrate that the mutation(s) that alters the apparent promoter specificity of the T7 RNA polymerase encoded on pKGP-HA1mut4 is within T7 gene 1, restriction fragments from pKGP-HA1mut4 were ligated into a wild type pKGP1-1 plasmid, and the new plasmids were tested for their ability to confer chloramphenicol resistance to *E. coli* harboring the inactive promoter selection plasmid pCM-P1031. The first restriction fragments that were cleaved from pKGP-HA1 mut4 and ligated into wild type pKGP1-1 were the T7 gene 1 EcoRI/HpaI and HpaI/PstI restriction fragments. On pKGP-HA1 mut4 and on pKGP1-1 EcoRI cleaves between the tac promoter and the ATG of gene 1, HpaI cleaves near the middle of gene 1, and PstI cleaves just after the stop codon of gene 1. This allows the amino and carboxyl halves of gene 1 to be independently ligated into a wild type pKGP1-1 and generates the new plasmids pMutE/H and pMutH/P that contain the amino and carboxyl halves of the gene 1 from pKGP-HA1mut4, respectively (FIG. 3).

*E. coli* JM101 was cotransformed with pCM-P1031 (Table I) and either pMutE/H or pMutH/P, and the transformations were spread on kan/amp, kan/amp/IPTG, and kan/amp/cam plates. Only cells containing pMutE/H and pCM-P1031 were able to grow in the presence of chloramphenicol. This confirmed that the mutation responsible for altered promoter specificity was within gene 1 and suggested that the mutation was located in the amino half of the gene.

The same strategy was used to construct and test the plasmids shown in FIG. 3, and altered promoter specificity always segregated with the amino terminal restriction fragment. This allowed us to localize the promoter specificity mutation to the 832 bp EcoRI/BstXI restriction fragment cloned into pMutE/B; however, further localization of the promoter specificity mutation required manipulation of pMutE/B.

The restriction enzyme AlwNI cleaves pMutE/B and pKGP1-1 twice, between the EcoRI and BstXI sites within gene 1 and near the origin of replication of the plasmids. By ligating the two AlwNI fragments of pMutE/B to the two reciprocal AlwNI fragments of pKGP1-1, the clones pMutE/A and pMutA/B are generated (FIG. 3), and the EcoRI/BstXI fragment of pMutE/B is further subdivided. When pMutE/A and pMutA/B were tested for altered promoter specificity, only pMutA/B conferred chloramphenicol resistance to *E. coli* harboring pCM-P1031. In addition, *E. coli* JM101 cotransformed with pMutA/B and pCAT10-1, pKK232-8, or each of the seven different inactive pCM-X# separately showed the same growth characteristics on kan/amp, kan/amp/cam, and kan/amp/IPTG plates as was observed with pKGP-HA1mut4 (data not shown). This suggested that the T7 gene 1 mutation responsible for altered promoter specificity was located on the 383 bp AlwNI/BstXI restriction fragment.

Finally, sequencing of the 383 bp region using an M13mp19 clone of the pKGP-HA1 mut4 mutant gene 1 revealed that the only difference between the wild type T7 gene 1 and the mutant gene 1 was a G to A transition at position 664 of T7 gene 1 (FIG. 4). Since the phenotypic assays done with the mutant gene 1 subclones showed that the mutation affecting the specificity of the mutant T7 RNA polymerase was located between positions 753 and 1143 of pKGP-HA1mut4, the mutation at 1105 of pKGP-HA1mut4 (position 664 in relation to T7 gene 1) that changes glutamic acid 222 to lysine is probably responsible for the altered promoter specificity of the mutant RNA polymerase (GP1(lys222)).

5. The In Vivo and In Vitro Specificity of GP1(lys222)

In previous work with the compatible plasmids pKGP1-1 and pCM-X#, equivalent bacterial growth on kan/amp and kan/amp/cam plates accompanied by no growth on kan/amp/IPTG plates indicated that the pCM-X# plasmid carried a strong T7 promoter [Ikeda, R. A., et al., *Biochemistry*, 31: 9073–9080 (1992); Ikeda, R. A., et al., *Nucl. Acids. Res.*, 20: 2517–2524 (1992)]. With pKGP-HA1mut4 and pMutA/B, the seven inactive pCM-X# plasmids and pCAT10-1 all showed equivalent bacterial growth on kan/amp and kan/amp/cam plates and no growth on kan/amp/IPTG plates (Table 2), but control experiments also showed that *E. coli* JM101 harboring pMutA/B would not grow on amp/IPTG plates (data not shown). Apparently, the lack of growth on kan/amp/IPTG plates is due to the over production of the mutant T7 RNA polymerase and is not an indication of a strong promoter on the pCM-X# selection plasmid. The mutant RNA polymerase may be toxic or the mutant RNA polymerase may utilize cryptic T7-like promoters within the cell that express proteins that kill the host *E. coli*.

Although the toxicity of the overproduced mutant T7 RNA polymerase makes it impossible to judge the efficiency of promoter usage in plating experiments, it does not seem to interfere with the selection of possible promoter recognition mutants of T7 RNA polymerase in the absence of IPTG. However, to estimate how efficiently GP1(lys222) RNA polymerase utilizes point mutants of T7 promoters it is necessary to directly measure promoter activity in vivo and in vitro.

We have previously shown that in vivo usage of the potential T7 promoters carried on the pCM-X# plasmids can be estimated by measuring CAT activity relative to β-lactamase activity in extracts of E. coli harboring pKGP1-1 and pCM-X# plasmid. [Ikeda, R. A., et al., Biochemistry, 31: 9073–9080 (1992); Ikeda, R. A., et al., Nucl. Acids Res., 20: 2517–2524 (1992)]. From these measurements, if in vivo usage of the wild-type T7 promoter (pCAT10-1) by wild-type T7 RNA polymerase (pKGP1-1) is defined as 1.0, then in vivo usage of the inactive T7 promoter point mutants by wild-type T7 RNA polymerase ranges from 0.005±0.003 to 0.01±0.005, and in vivo usage of the three intermediate strength T7 promoter point mutants ranges from 0.04±0.018 to 0.40±0.18 (FIG. 5A). In contrast, while in vivo usage of the wild-type T7 promoter (pCAT10-1) by GP1(lys222) is comparable to usage of the same promoter by wild-type T7 RNA polymerase, in vivo usage of the inactive T7 promoter point mutants by GP1(lys222) ranges from 0.024±0.109 to 0.22±0.12, and in vivo usage of the three intermediate T7 promoter point mutants ranges from 0.22±0.048 to 0.91±0.39 (FIG. 5A). This showed that GP1(lys222) uses the inactive and intermediate T7 promoter point mutants 5 to 25 times and 2 to 6 times more efficiently than wild-type T7 RNA polymerase, respectively (FIG. 5A).

To confirm the in vivo measurements, promoter usage was also measured in vitro. Although T7 RNA polymerase and GP1(lys222) exhibit different absolute activities in these in vitro reactions (Table 3) relative comparisons are informative. If in vitro usage of the wild-type T7 promoter (pCAT10-1) by both T7 RNA polymerase and GP1(lys222) is defined as 1.0, the in vitro usage of the inactive and intermediate T7 promoter point mutants by T7 RNA polymerase ranges from 0.005±0.005 to 0.018±0.005 and 0.005±0.005 to 0.36±0.03 (FIG. 5B), respectively, while the in vitro usage of the inactive and intermediate T7 promoter point mutants by GP1(lys222) ranges from 0.014±0.005 to 0.05±0.01 and 0.04±0.01 to 0.81±0.03, respectively. Although the absolute magnitudes of in vivo and in vitro promoter usage differ, the trends noted for in vivo promoter usage are almost duplicated in the in vitro measurements; however, some differences are noted. For example, while the in vitro data shows that GP1(lys222) uses the intermediate T7 promoter point mutants 2 to 8 times more efficiently than T7 RNA polymerase, the data also shows that the mutant enzyme uses the inactive T7 promoter point mutants only 2 to 6 times more efficiently than the wild-type RNA polymerase. This difference in the in vivo and in vitro data is probably due to the difficulties encountered in measuring the low in vitro usage of the inactive T7 promoter point mutants by T7 RNA polymerase. Since background is difficult to subtract from these measurements, it is likely that in vitro usage of the inactive T7 promoter point mutants by T7 RNA polymerase is overestimated and that the relative increase in the efficiency of in vitro usage of these promoters by GP1(lys222) is underestimated.

6. Utilization of Homologous Phage Promoters

The ability of GP1(lys222) to utilize the seven different T7 promoter point mutants that are not utilized by wild-type T7 RNA polymerase showed that the mutant T7 RNA polymerase is less specific than the wild-type enzyme, but these measurements do not define a limit to the sequence variations accommodated by GP1(lys222). To determine if GP1(lys222) still requires the context of a T7 promoter, transcription from plasmids containing no T7 promoter, an SP6 promoter, or a T3 promoter was measured in vitro. FIG. 6 shows that little or no RNA is produced in the presence of templates carrying no promoter or an SP6 promoter GP1(lys222) and that a T3 promoter is poorly utilized by either wild-type T7 RNA polymerase (activity=0.009±0.003) or GP1(lys222) (activity=0.027±0.008). However, GP1(lys222) uses a T3 promoter more efficiently than wild-type T7 RNA polymerase, and the in vitro utilization of the T3 promoter by GP1(lys222) is comparable to the in vitro utilization of a number of the inactive T7 promoter point mutants. Nevertheless, this result may not actually reflect specific initiation at the T3 promoter of pLM10 since few specific transcripts are seen with GP1(lys222) in the run-off assays shown below. The in vitro activity of GP1(lys222) on pLM 10 may simply reflect nonspecific initiation.

7. Initiation of Transcription Occurs at the Potential T7 Promoters

To show that transcription initiates at the potential T7 promoters on the pCM-X# plasmids run-off transcripts produced by T7 RNA polymerase and GP1(lys222) were compared. A plasmid carrying a wild-type T7 promoter (pCAT10-1), a plasmid carrying an intermediate strength T7 promoter point mutant (pCM-P1198), two plasmids carrying inactive T7 promoter point mutants (pCM-T270 and pCM-P1208), and a plasmid carrying a T3 promoter (pLM10) were linearized by cleaving the plasmids with either NdeI (the pCM-X# plasmids) or PvuII (pLM10). Cleavage of the pCM-X# plasmids with NdeI places the potential T7 promoters 2905 nucleotides from the end of each template, while cleavage of pLM10 with PvuII places the T3 promoter 2371 nucleotides from the end of its template. The linearized plasmids were then used in transcription reactions containing either 80 nM T7 RNA polymerase or 40 nM GP1(lys222). FIG. 7 shows that the lengths of the run-off transcripts produced by T7 RNA polymerase are identical to the lengths of the run-off transcripts produced GP1(lys222). In addition, specific run-off transcripts are easily observed in reactions containing T7-like promoters, while specific run-off transcript are barely detectable in reactions containing a T3 promoter (pLM10/PvuII). The run-off doublets seen in the pCM-X# lanes of FIG. 7 are due to the presence of a sequence near the end of the pCM-X# templates that acts as a terminator of T7 transcription. This would seem to indicate that transcription by GP1(lys222) is promoter dependent and that the promoter must resemble a T7 promoter.

8. Promoter Binding by GP1(lys222)

A two amino acid insertion at position 222 of T7 RNA polymerase has been previously reported to disrupt promoter binding without affecting polymerase function [Gross, L., et al., J. Mol. Biol., 228: 488–505 (1993)]; however, the opposite phenomenon, tighter promoter binding, would be a plausible mechanism that might explain the ability of GP1(lys222) to recognize an expanded range of T7 promoter-like sequences. The positively charged lysine side chain could stabilize the binding of the RNA polymerase to the negatively charged DNA template and improve the ability of the mutant enzyme to recognize promoter-like sequences. To test whether the expanded specificity of GP1(lys222) is due to stabilization of the promoter/enzyme complex, the binding of T7 RNA polymerase and GP1(lys222) to an oligonucleotide containing a T7 promoter was measured by gel retardation. FIG. 8 shows that GP1(lys222) is still capable of forming promoter specific complexes, but that the affinity of the mutant enzyme for a T7 promoter is diminished. The data obtained from two different trials suggests that the promoter binding affinity of GP l(lys222) ($1.4 \times 10^4 M^{-1} \pm 5 \times 10^3 M^{-1}$) is twenty times less than the promoter binding of wild-type T7 RNA polymerase ($2.8 \times 10^5 M^{-1} \pm 2.2 \times 10^5 M^{-1}$). In addition, it is also observed that a GP1(lys222)/T7 promoter complex is more easily disrupted by nonspecific competitor DNA (FIG. 8, lanes 4 and 5) than a wild-type T7 RNA polymerase/T7 promoter complex (FIG. 8, lanes 8 and 9). The susceptibility of GP1(lys222)/promoter complexes to disruption by nonspecific DNA could either be due to the decreased stability of the specific enzyme/promoter complex or to an increased affinity for nonspecific DNA. Whatever the case, the Glu to Lys substitution in GP1(lys222) produces an enzyme with reduced affinity for T7 promoters and an ability to utilize an expanded range of T7 promoter-like sequences.

The above detailed description of the preferred embodiment of this invention is for illustrative purposes and is not meant to limit the spirit or scope of this invention, or its equivalents, as defined in the appended claims.

TABLE I

Selection Plasmids

| Promoter Selection Plasmid | Type of Promoter[a] | Mutation Carried by the Promoter | Phenotypic Promoter Strength[b] |
|---|---|---|---|
| pKK232-8 | None | None | Inactive |
| pCAT10-1 | Wild Type T7 | None | Strong |
| pCM-T297 | Point Mutant | −11G to T | Inactive |
| pCM-P1160 | Point Mutant | −9C to G | Inactive |
| pCM-T270 | Point Mutant | −9C to A | Inactive |
| pCM-P1087 | Point Mutant | −9C to T | Inactive |
| pCM-P1198 | Point Mutant | −8T to G | Intermediate |
| pCM-T286 | Point Mutant | −8T to A | Inactive |
| pCM-B64 | Point Mutant | −8T to C | Intermediate[c] |
| pCM-P1208 | Point Mutant | −7C to G | Inactive |
| pCM-P1031 | Point Mutant | −7C to A | Inactive |
| pCM-T221 | Point Mutant | −6A to G | Intermediate[d] |

[a]Point Mutant indicates that a T7 promoter containing a single point mutation is carried on the selection plasmid.
[b]Phenotypic Promoter Strength is an estimate of in vivo promoter activity as assayed in plating experiments with wild-type T7 RNA polymerase (Ikeda et al. 1992a, Ikeda et al. 1992b).
[c]Classified as intermediate but borders on inactive.
[d]Classified as intermediate but borders on strong.

TABLE II

Phenotypic Characterization of pKGP-HA1mut4

| Promoter Selection Plasmid[a] | Mutation in the T7 Promoter | T7 RNA Polymerase Plasmid | Numbers of Colonies[b] | | |
|---|---|---|---|---|---|
| | | | Kan/Amp | Kan/Amp/Cam | Kan/Amp/IPTG |
| pCAT10-1 | None | pKGP1-1 | 200 | 200 | 0 |
| Mix of all 7 Inactive | All 7 Inactive | pKGP1-1 | 200 | 0 | 200 |
| pKK232-8 | No Promoter | pKGP1-1 | 200 | 0 | 200 |
| pCAT10-1 | None | PKGP-HA1mut4 | 200 | 200 | 0 |
| pKK232-8 | No Promoter | pKGP-HA1mut4 | 200 | 0 | 0 |
| Mix of all 7 Inactive | All 7 Inactive | pKGP-HA1mut4 | 200 | 200 | 0 |
| pCM-T270 | −9C to A | pKGP-HA1mut4 | 200 | 200 | 0 |
| pCM-T286 | −8T to A | pKGP-HA1mut4 | 200 | 200 | 0 |
| pCM-T297 | −11G to T | pKGP-HA1mut4 | 200 | 200 | 0 |
| pCM-P1031 | −7C to A | pKGP-HA1mut4 | 200 | 200 | 0 |
| pCM-P1087 | −9C to T | pKGP-HA1mut4 | 200 | 200 | 0 |
| pCM-P1160 | −9C to G | pKGP-HA1mut4 | 200 | 200 | 0 |
| pCM-P1208 | −7C to G | pKGP-HA1mut4 | 200 | 200 | 0 |

[a]Promoter selection plasmid cotransformed with pKGP1-1
[b]The number of colonies found on the indicated plates.

TABLE III

Assay Conditions Affect the Specific Activities of T7 RNA Polymerase and GP1(lys222)

| Enzyme | DNA | Specific Activity (u/mg) | |
|---|---|---|---|
| | | Buffer A[1] | Buffer B[2] |
| GP1(lys222) | T7 | 14,800 | 26,300 |
| | pCAT10-1 | 2,500 | 1,900 |
| | pCAT10-1/NdeI | 2,200 | 2,600 |
| T7 RNA polymerase | T7 | 43,700 | 6,600 |
| | pCAT10-1 | 18,900 | 5,900 |
| | pCAT10-1/NdeI | 15,100 | 1,600 |

[1]Buffer A-50 mM Tris-HCl, pH 8, 10 mM MgCl$_2$
[2]Buffer B-50 mM Tris-HCl, pH 8, 10 mM MgCl$_2$, 60 mM NaCl, and 2.5 mM spermidine

TABLE IV

Oligodeoxyribonucleotides.

| Designation | Sequence |
|---|---|
| | −17                                              +6 |
| WT | 5'-CTGAATTCGAAATTAATACGACTCACTATAGGGAGAAAGCTTGGTACCAG-3' |
| B | 5'-CTGAATTC*gaaattaatacgactcactatagggaga*AAGCTTGGTACCAG-3' |
| T | 5'-CTAGTACT*gaaattaatacgactcactatagggaga*AAGCTTGGTACCAG-3' |
| P | 5'-CTAGTACTGAAATTAATACGA*ctc*ACTATAGGGAGAAAGCTTGGTACCAG-3' |
| C | 5'-CTAGTACTGAAATTAATACG*c*CTCACTATAGGGAGAAAGCTTGGTACCAG-3' |
| G | 5'-CTAGTACTGAAATTAATACG*g*CTCACTATAGGGAGAAAGCTTGGTACCAG-3' |
| Primer | 5'-CTGGTACCAAGCTT-3' |

Oligonucleotides B, P, C, G, and Primer were purchased from National Biosciences. Oligo T was purchased from New England Biolabs, and Oligo WT was a gift from Dr. Keith McKenney, Center for Advanced Research in Biotechnology. In oligos B and T, the lower case italics are used to designate those bases in the oligonucleotide that are a mixture of 96.1% of the indicated base and 1.3% of each of the other 3 bases. In oligo P, the lower case italics are used to designate those bases in the oligonucleotide that are a mixture of 67.0% of the indicated base and 11% of each of the other 3 bases. The mutation in oligo C is an A to C (lower case italics) point mutation at −10, and the mutation in oligo G is an A to G (lower case italics) point mutation at −10. The primer oligo is complementary to the 3' end of oligos WT, B, P, T, C, and G.

What is claimed is:

1. An isolated and purified mutant T7 RNA polymerase that carries the substitution of lysine for glutamic acid at amino acid 222.

2. The mutant T7 RNA polymerase as claimed in claim 1, having the ability to recognize and utilize point mutations of wild-type T7 promoter sequences.

3. The mutant T7 RNA polymerase as claimed in claim 2, wherein said point mutations of wild-type T7 promoter sequences are selected from the group consisting of all those promoter sequences recognized and utilized by a wild-type T7 RNA polymerase, and the following substitutions of the T7 promoter: cytidine to adenosine at $-7$, cytidine to guanosine at $-7$, thymidine to adenosine at $-8$, cytidine to adenosine at $-9$, cytidine to thymidine at $-9$, cytidine to guanosine at $-9$, and guanosine to thymidine at $-11$.

4. The mutant T7 RNA polymerase as claimed in claim 3, wherein said point mutations of wild-type T7 promoter sequences are selected from the group consisting of the following substitutions of the wild-type T7 promoter: cytidine to adenosine at $-7$, cytidine to guanosine at $-7$, thymidine to adenosine at $-8$, cytidine to adenosine at $-9$, cytidine to thymidine at $-9$, cytidine to guanosine at $-9$, and guanosine to thymidine at $-11$.

* * * * *